(12) United States Patent
Zhang et al.

(10) Patent No.: US 7,790,726 B2
(45) Date of Patent: Sep. 7, 2010

(54) MONOCYCLIC AND BICYCLIC COMPOUNDS AND METHODS OF USE

(75) Inventors: Penglie Zhang, Foster City, CA (US); Andrew M. K. Pennell, San Francisco, CA (US); John J. Kim Wright, Redwood City, CA (US); Lianfa Li, Palo Alto, CA (US); Edward J. Sullivan, San Jose, CA (US); Wei Chen, Fremont, CA (US); Kevin Lloyd Greenman, Burlingame, CA (US)

(73) Assignee: Chemocentryx, Inc., Mountain View, CA (US)

( * ) Notice: Subject to any disclaimer, the term of this patent is extended or adjusted under 35 U.S.C. 154(b) by 151 days.

(21) Appl. No.: 11/504,215

(22) Filed: Aug. 14, 2006

(65) Prior Publication Data

US 2007/0066583 A1 Mar. 22, 2007

Related U.S. Application Data

(60) Provisional application No. 60/709,266, filed on Aug. 16, 2005.

(51) Int. Cl.
*C07D 263/58* (2006.01)
*C07D 413/06* (2006.01)
*A61K 31/496* (2006.01)
*C07D 401/06* (2006.01)
*C07D 498/04* (2006.01)

(52) U.S. Cl. .................. 514/254.02; 544/368; 544/373; 544/236; 544/262; 544/350; 544/49; 544/50; 544/51; 544/52; 544/91; 544/105; 544/353; 544/354; 544/355; 544/356; 544/48; 544/349; 544/369; 544/370; 544/60; 544/121; 544/357; 544/360; 544/362; 546/198; 546/199; 546/201; 546/113; 546/114; 546/115; 546/116; 546/117; 546/118; 546/119; 546/120; 546/153; 546/157; 546/122; 546/123; 546/208; 546/209; 546/210; 546/187; 546/196; 540/575

(58) Field of Classification Search ....................... None
See application file for complete search history.

(56) References Cited

U.S. PATENT DOCUMENTS

| 2004/0034034 A1 | 2/2004 | Blumberg et al. |
| 2005/0075348 A1 | 4/2005 | Harriman et al. |
| 2005/0143372 A1 | 6/2005 | Ghosh et al. |

FOREIGN PATENT DOCUMENTS

WO 03/105853 A1 * 12/2003

OTHER PUBLICATIONS

Onkol et al. Arch. Pharm. Pharm.Med.Chem. vol. 334, p. 17-20 (2001).*
Lozanova et al. Oxidation Communications, vol. 28 (3), p. 740-745 (Sep. 2005).*

* cited by examiner

*Primary Examiner*—Emily Bernhardt
(74) *Attorney, Agent, or Firm*—Townsend and Townsend and Crew LLP

(57) ABSTRACT

Compounds are provided that act as potent antagonists of the CCR1 receptor, and have in vivo anti-inflammatory activity. The compounds are generally monocyclic and bicyclic compounds and are useful in pharmaceutical compositions, methods for the treatment of CCR1-mediated diseases, and as controls in assays for the identification of competitive CCR1 antagonists.

7 Claims, 6 Drawing Sheets

MONOCYCLIC AND BICYCLIC COMPOUNDS AND METHODS OF USE

CROSS-REFERENCES TO RELATED APPLICATIONS

This application claims priority to U.S. Provisional Application No. 60/709,266, filed on Aug. 16, 2005, the content of which is incorporated herein in its entirety for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The present invention provides compounds, pharmaceutical compositions containing one or more of those compounds or their pharmaceutically acceptable salts, which are effective in inhibiting the binding of various chemokines, such as MIP-1α, leukotactin, MPIF-1 and RANTES, to the CCR1 receptor. As antagonists or modulators for the CCR1 receptor, the compounds and compositions have utility in treating inflammatory and immune disorder conditions and diseases.

Human health depends on the body's ability to detect and destroy foreign pathogens that might otherwise take valuable resources from the individual and/or induce illness. The immune system, which comprises leukocytes (white blood cells (WBCs): T and B lymphocytes, monocytes, macrophages granulocytes, NK cell, mast cells, dendritic cell, and immune derived cells (for example, osteoclasts)), lymphoid tissues and lymphoid vessels, is the body's defense system. To combat infection, white blood cells circulate throughout the body to detect pathogens. Once a pathogen is detected, innate immune cells and cytotoxic T cells in particular are recruited to the infection site to destroy the pathogen. Chemokines act as molecular beacons for the recruitment and activation of immune cells, such as lymphocytes, monocytes and granulocytes, identifying sites where pathogens exist.

Despite the immune system's regulation of pathogens, certain inappropriate chemokine signaling can develop and has been attributed to triggering or sustaining inflammatory disorders, such as rheumatoid arthritis, multiple sclerosis and others. For example, in rheumatoid arthritis, unregulated chemokine accumulation in bone joints attracts and activates infiltrating macrophages and T-cells. The activities of these cells induce synovial cell proliferation that leads, at least in part, to inflammation and eventual bone and cartilage loss (see, DeVries, M. E., et al., *Semin Immunol* 11(2):95-104 (1999)). A hallmark of some demyelinating diseases such as multiple sclerosis is the chemokine-mediated monocyte/macrophage and T cell recruitment to the central nervous system (see, Kennedy, et al., *J. Clin. Immunol.* 19(5):273-279 (1999)). Chemokine recruitment of destructive WBCs to transplants has been implicated in their subsequent rejection. See, DeVries, M. E., et al., ibid. Because chemokines play pivotal roles in inflammation and lymphocyte development, the ability to specifically manipulate their activity has enormous impact on ameliorating and halting diseases that currently have no satisfactory treatment. In addition, transplant rejection may be minimized without the generalized and complicating effects of costly immunosuppressive pharmaceuticals.

Chemokines, a group of greater than 40 small peptides (7-10 kD), ligate receptors expressed primarily on WBCs or immune derived cells, and signal through G-protein-coupled signaling cascades to mediate their chemoattractant and chemostimulant functions. Receptors may bind more than one ligand; for example, the receptor CCR1 ligates RANTES (regulated on activation normal T cell expressed), MIP-1α (macrophage inflammatory protein), MPIF-1/CKβ8, and Leukotactin chemokines (among others with lesser affinities). To date, 24 chemokine receptors are known. The sheer number of chemokines, multiple ligand binding receptors, and different receptor profiles on immune cells allow for tightly controlled and specific immune responses. See, Rossi, et al., *Ann. Rev. Immunol.* 18(1):217-242 (2000). Chemokine activity can be controlled through the modulation of their corresponding receptors, treating related inflammatory and immunological diseases and enabling organ and tissue transplants.

The receptor CCR1 and its chemokine ligands, including, for example MIP-1α, MPIF-1/CKβ8, leukotactin and RANTES, represent significant therapeutic targets (see Saeki, et al., *Current Pharmaceutical Design* 9:1201-1208 (2003)) since they have been implicated in rheumatoid arthritis, transplant rejection (see, DeVries, M. E., et al., ibid.), and multiple sclerosis (see, Fischer, et al., *J Neuroimmunol.* 110 (1-2):195-208 (2000); Izikson, et al., *J. Exp. Med.* 192(7): 1075-1080 (2000); and Rottman, et al., *Eur. J. Immunol.* 30(8):2372-2377 (2000). In fact, function-blocking antibodies, modified chemokine receptor ligands and small organic compounds have been discovered, some of which have been successfully demonstrated to prevent or treat some chemokine-mediated diseases (reviewed in Rossi, et al., ibid.). Notably, in an experimental model of rheumatoid arthritis, disease development is diminished when a signaling-blocking, modified-RANTES ligand is administered (see Plater-Zyberk, et al., *Immunol Lett.* 57(1-3):117-120 (1997)). While function-blocking antibody and small peptide therapies are promising, they suffer from the perils of degradation, extremely short half-lives once administered, and prohibitive expense to develop and manufacture, characteristic of most proteins. Small organic compounds are preferable since they often have longer half lives in vivo, require fewer doses to be effective, can often be administered orally, and are consequently less expensive. Some organic antagonists of CCR1 have been previously described (see, Hesselgesser, et al., *J. Biol. Chem.* 273(25): 15687-15692 (1998); Ng, et al., *J. Med. Chem.* 42(22):4680-4694 (1999); Liang, et al., *J. Biol. Chem.* 275(25):19000-19008 (2000); and Liang, et al., *Eur. J. Pharmacol.* 389(1):41-49 (2000)). In view of the effectiveness demonstrated for treatment of disease in animal models (see, Liang, et al., *J. Biol. Chem.* 275(25):19000-19008 (2000)), the search has continued to identify additional compounds that can be used in the treatment of diseases mediated by CCR1 signaling.

BRIEF SUMMARY OF THE INVENTION

In one aspect, the present invention provides compounds having the Formula I:

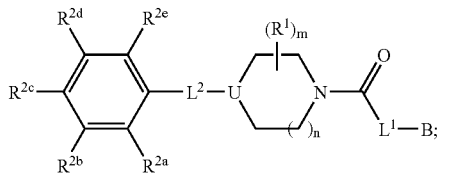

(I)

or pharmaceutically acceptable salts and N-oxides thereof, in which each $R^1$ is independently selected from the group consisting of $C_{1-8}$ alkyl, $C_{1-8}$ haloalkyl, $C_{3-6}$ cycloalkyl, —$CO_2R^a$, —$X^1CO_2R^a$, —$X^1SO_2R^a$, —$X^1SO_3R^a$, —$X^1OR^a$, —$COR^a$, —$CONR^aR^b$, —$X^1NR^aR^b$, —$X^1NR^aCOR^b$, —$X^1CONR^aR^b$, $X^1NR^aS(O)_2R^b$, $X^1S(O)_2NR^aR^b$ and $X^1S(O)_2R^a$. In Formula I, $X^1$ is $C_{1-4}$ alkylene and each $R^a$ and $R^b$ is independently selected from the group consisting of hydrogen, $C_{1-8}$ alkyl, $C_{1-8}$ haloalkyl and $C_{3-6}$ cycloalkyl. $R^a$ and $R^b$ when attached to the same nitrogen atom are optionally combined to form a 5- to 7-membered ring having from 0-2 heteroatoms selected from the group consisting of N, O and S. Optionally any two $R^1$ substituents attached to the same atom are optionally replaced with the substituent =O, =NH, =NOH, =$NR^a$, =S or =$CR^aR^b$. Optionally, any two $R^1$ substituents attached to the same or adjacent carbon atoms are cyclized to form a 3- to 7-membered ring. The aliphatic portions of each $R^1$ substituent is optionally substituted with from one to three members selected from the group consisting of —OH, —$OR^m$, —OC(O)$NHR^m$, —OC(O)N($R^m$)$_2$, —SH, —$SR^m$, —S(O)$R^m$, —S(O)$_2R^m$, —$SO_2NH_2$, —S(O)$_2NHR^m$, —S(O)$_2$N($R^m$)$_2$, —NHS(O)$_2R^m$, —$NR^mS(O)_2R^m$, —C(O)$NH_2$, —C(O)$NHR^m$, —C(O)N($R^m$)$_2$, —C(O)$R^m$, —NHC(O)$R^m$, —$NR^mC(O)R^m$, —NHC(O)$NH_2$, —$NR^mC(O)NH_2$, —$NR^mC(O)NHR^m$, —NHC(O)$NHR^m$, —$NR^mC(O)N(R^m)_2$, —NHC(O)N($R^m$)$_2$, —$CO_2H$, —$CO_2R^m$, —$NHCO_2R^m$, —$NR^mCO_2R^m$, —CN, —$NO_2$, —$NH_2$, —$NHR^m$, —N($R^m$)$_2$, —$NR^mS(O)NH_2$ and —$NR^mS(O)_2NHR^m$, in which each $R^m$ is independently an unsubstituted $C_{1-6}$ alkyl, and the subscript m is an integer from 0-4.

The symbols $R^{2a}$, $R^{2b}$, $R^{2c}$, $R^{2d}$ and $R^{2e}$ at each occurrence are each independently selected from the group consisting of hydrogen, halogen, cyano, heteroaryl, —$NO_2$, —$CO_2R^c$, —C(O)$NR^cR^d$, —C(O)$R^c$, —S(O)$R^e$, —S(O)$_2R^e$, —$NR^cS(O)_2R^e$, —$R^e$, —$C(NOR^c)R^d$, $C(NR^cV)=NV$, —N(V)C($R^c$)=NV, —$NR^dC(O)_2R^e$, $NR^cC(O)NR^cR^d$, —NH—C($NH_2$)=NH, $NR^eC(NH_2)=NH$, —NH—C($NH_2$)=$NR^e$, —NH—C($NHR^e$)=NH, —$X^2C(NR^cV)=NV$, —$X^2N(V)C(R^c)=NV$ —$X^2C(NOR^c)R^d$, —$X^2C(NR^cV)=NV$, —$X^2N(V)C(R^c)=NV$, —$NR^cR^d$, —$X^2SR^c$, —$X^2CN$, —$X^2NO_2$, —$X^2CO_2R^c$, —$X^2CONR^cR^d$, —$X^2C(O)R^c$, —$X^2OC(O)NR^cR^d$, —$X^2NR^dC(O)R^c$, —$X^2NR^dC(O)_2R^e$, —$X^2NR^cC(O)NR^cR^d$, —$X^2NH—C(NH_2)=NH$, —$X^2NR^cC(NH_2)=NH$, —$X^2NH—C(NH_2)=NR^e$, —$X^2NH—C(NHR^e)=NH$, —$X^2S(O)R^e$, —$X^2NR^cS(O)_2R^e$, —$X^2S(O)_2NR^cR^d$, —$X^2N_3$, —$OR^c$, —$SR^c$, —$NR^dC(O)R^c$, —$NR^dC(O)_2R^e$, —S(O)$_2NR^cR^d$, —$X^2OR^c$, —O—$X^2OR^c$, —$X^2NR^cR^d$, —O—$X^2NR^cR^d$ and —$NR^d—X^2CO_2R^c$. The symbol $X^2$ is $C_{1-4}$ alkylene and each $R^c$ and $R^d$ is independently selected from hydrogen, $C_{1-8}$ alkyl, $C_{1-8}$ haloalkyl, $C_{3-6}$ cycloalkyl, or optionally, $R^c$ and $R^d$ when attached to the same nitrogen atom can be combined with the nitrogen atom to form a five or six-membered ring having from 0 to 2 additional heteroatoms as ring members. Each $R^e$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl and heteroaryl. Each of $R^c$, $R^d$ and $R^e$ is optionally further substituted with from one to three members selected from the group consisting of —OH, —$OR''$, —OC(O)$NHR''$, —OC(O)N($R''$)$_2$, —SH, —$SR''$, —S(O)$R''$, —S(O)$_2R''$, —$SO_2NH_2$, —S(O)$_2NHR''$, —S(O)$_2N(R'')_2$, —NHS(O)$_2R''$, —$NR''S(O)_2R''$, —C(O)$NH_2$, —C(O)$NHR''$, —C(O)N($R''$)$_2$, —C(O)$R''$, —NHC(O)$R''$, —$NR''C(O)R''$, —NHC(O)$NH_2$, —$NR''C(O)NH_2$, —$NR''C(O)NHR''$, —NHC(O)$NHR''$, —$NR''C(O)N(R'')_2$, —NHC(O)N($R''$)$_2$, —$CO_2H$, —$CO_2R''$, —$NHCO_2R''$, —$NR''CO_2R''$, —CN, —$NO_2$, —$NH_2$, —$NHR''$, —N($R''$)$_2$, —$NR''S(O)NH_2$ and —$NR''S(O)_2NHR''$, wherein each $R''$ is independently an unsubstituted $C_{1-6}$ alkyl, and wherein V is independently selected from the group consisting of —$R^c$, —CN, —$CO_2R^e$ and —$NO_2$.

The symbol B represents a monocyclic (-$B^1$) or bicyclic (-$B^1$-$B^2$) ring system in which $B^1$ is attached to the remainder of the compound of Formula I. $B^1$ is a 5- to 7-membered non-aromatic nitrogen containing heterocyclic ring optionally having 1-2 additional heteroatom ring members selected from the group consisting of N, O, S, S(O) and S(O)$_2$, and optionally having up to two double bonds; and $B^2$ is selected from the group consisting of phenyl, pyridinyl, pyrimidinyl, pyrazinyl and pyridazinyl. When B is a bicyclic ring system, then $B_1$ and $B_2$ are fused or connected with a single bond. The $B^1$ and $B^2$ rings are both each independently further substituted with 0 to 5 $R^3$ substituents. At each occurrence, $R^3$ is independently selected from the group consisting of hydrogen, halogen, —$OR^f$, —OC(O)$R^f$, —$NR^fR^g$, —$SR^f$, —$R^h$, —CN, —$NO_2$, —$CO_2R^f$, —$CONR^fR^g$, —C(O)$R^f$, —OC(O)$NR^fR^g$, —$NR^gC(O)R^f$, —$NR^gC(O)_2R^h$, —$NR^f$—C(O)$NR^fR^g$, —NH—C($NH_2$)=NH, —$NR^hC(NH_2)=NH$, —NH—C($NH_2$)=$NR^h$, —C($NR^fR^g$)=$NOR^f$, —S(O)$_3R^h$, $X^3S(O)_3R^f$, —NH—C($NHR^h$)=NH, —S(O)$R^h$, —S(O)$_2R^h$, —$NR^fS(O)_2R^h$, —S(O)$_2NR^fR^g$, —$NR^fS(O)_2R^h$, —$NR^fS(O)_2NR^fR^g$, —$N_3$, —$X^3OR^f$, —$X^3OC(O)R^f$, —$X^3NR^fR^g$, —$X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2R^h$, —$X^3NR^f$—C(O)$NR^fR^g$, —$X^3NH$—C($NH_2$)=NH, —$X^3NR^hC(NH_2)=NH$, —$X^3NH$—C($NH_2$)=$NR^h$, —$X^3NH$—C($NHR^h$)=NH, —$X^3S(O)R^h$, —$X^3S(O)_2R^h$, —$X^3NR^fS(O)_2R^h$, —$X^3S(O)_2NR^fR^g$, —Y, —$X^3Y$ and —$X^3N_3$, wherein Y is a five to ten-membered aryl, heteroaryl or heterocycloalkyl ring, optionally substituted with from one to three substitutents selected from the group consisting of halogen, —$OR^f$, —$NR^fR^g$, —$R^h$, —$SR^f$, —CN, —$NO_2$, —$CO_2R^f$, —$CONR^fR^g$, —C(O)$R^f$, —$NR^gC(O)R^f$, —S(O)$R^h$, —S(O)$_2R^h$, —$NR^fS(O)_2R^h$, —S(O)$_2NR^fR^g$, —$X^3OR^f$, —$X^3NR^fR^g$, —$X^3NR^fS(O)_2R^h$, —$X^3CO_2R^f$, —$X^3CONR^fR^g$, —$X^3C(O)R^f$, —$X^3NR^gC(O)R^f$, —$X^3S(O)R^h$, —$X^3S(O)_2R^h$, and —$X^3S(O)_2NR^fR^g$. Any two $R^3$ substituents attached to the same atom on $B^1$ are optionally replaced with the substituent =O, =NH, =NOH, =$NR^f$, =S or =$CR^fR^g$. Furthermore, when B is a monocyclic ring system (-$B^1$), $R^3$ is not —Y. Optionally any two $R^3$ substituent located on adjacent atoms of $B^1$ or $B^2$ may be combined to form a 5- or 6-membered ring. Each $X^3$ is independently selected from the group consisting of $C_{1-4}$ alkylene, $C_{2-4}$ alkenylene and $C_{2-4}$ alkynylene; and each $R^f$ and $R^g$ substituent is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl and aryloxy-$C_{1-4}$ alkyl, or when attached to the same nitrogen atom can be combined with the nitrogen atom to form a five or six-membered ring having from 0 to 2 additional heteroatoms as ring members. Each $R^h$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl and aryloxy-$C_{1-4}$ alkyl, wherein the aliphatic portions of $X^3$, $R^f$, $R^g$ and $R^h$ are optionally further substituted with from one to three members selected from the group consisting of —OH, —OR$^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)$_2$NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$, wherein R$^o$ is unsubstituted $C_{1-6}$ alkyl.

The symbol $L^1$ is a linking group selected from the group consisting of $C_{1-3}$ alkylene, $C_{1-3}$ heteroalkylene, optionally substituted with phenyl, —R$^k$, —X$^4$OR$^i$, —X$^4$OC(O)R$^i$, —X$^4$NR$^i$R$^j$, —X$^4$SR$^i$, —X$^4$CN or —X$^4$NO$_2$. X$^4$ is selected from the group consisting of $C_{1-4}$ alkylene, $C_{2-4}$ alkenylene and $C_{2-4}$ alkynylene. Each R$^i$ and R$^j$ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl. Each R$^k$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl.

The symbol U is selected from the group consisting of N, C—R$^p$ and N$^+$—O$^-$, wherein R$^p$ is hydrogen, $C_{1-3}$ alkylene-OR$^q$, $C_{1-3}$ alkylene-N(R$^q$)$_2$, $C_{1-3}$ alkylene-NH(R$^q$), —OH, —OR$^q$, —R$^q$, —CN, —OC(O)NHR$^q$, —OC(O)N(R$^q$)$_2$, —SH, —SR$^q$, —S(O)R$^q$, S(O)$_2$R$^q$, —SO$_2$NH$_2$, S(O)$_2$NHR$^q$, —S(O)$_2$N(R$^q$)$_2$, —NHS(O)$_2$R$^q$, —NR$^q$S(O)$_2$R$^q$, —C(O)NH$_2$, —C(O)NHR$^q$, —C(O)N(R$^q$)$_2$, —C(O)R$^q$, —NHC(O)R$^q$, —NR$^q$C(O)R$^q$, —NHC(O)NH$_2$, —NR$^q$C(O)NH$_2$, —NR$^q$C(O)NHR$^q$, —NHC(O)NHR$^q$, —NR$^q$C(O)N(R$^q$)$_2$, —NHC(O)N(R$^q$)$_2$, —CO$_2$H, —CO$_2$R$^q$, —NHCO$_2$R$^q$, —NR$^q$CO$_2$R$^q$, —NH$_2$, —NHR$^q$, —N(R$^q$)$_2$, —NR$^q$S(O)NH$_2$, —NHC(=NH)NH$_2$, —NHC(=NH)R$^q$ and —NR$^q$S(O)$_2$NHR$^q$. R$^q$ is each independently $C_{1-8}$ alkyl, $C_{1-8}$ haloalkyl, $C_{3-8}$ cycloalkyl; and the aliphatic portions of R$^q$ is optionally further substituted with from one to three members selected from the group consisting of —OH, —OR$^r$, —OC(O)NHR$^r$, —OC(O)N(R$^r$)$_2$, —SH, —SR$^r$, —S(O)R$^r$, —S(O)$_2$R$^r$, —SO$_2$NH$_2$, —S(O)$_2$NHR$^r$, —S(O)$_2$N(R$^r$)$_2$, —NHS(O)$_2$R$^r$, —NR$^r$S(O)$_2$R$^r$, —C(O)NH$_2$, —C(O)NHR$^r$, —C(O)N(R$^r$)$_2$, —C(O)R$^r$, —NHC(O)R$^r$, —NR$^q$C(O)R$^r$, —NHC(O)NH$_2$, —NR$^r$C(O)NH$_2$, —NR$^r$C(O)NHR$^r$, —NHC(O)NHR$^r$, —NR$^r$C(O)N(R$^r$)$_2$, —NHC(O)N(R$^r$)$_2$, —CO$_2$H, —CO$_2$R$^r$, —NHCO$_2$R$^r$, —NR$^r$CO$_2$R$^r$, —CN, —NO$_2$, —NH$_2$, —NHR$^r$, —N(R$^r$)$_2$, —NR$^r$S(O)NH$_2$ and —NR$^r$S(O)$_2$NHR$^r$, wherein each R$^r$ is independently an unsubstituted $C_{1-6}$ alkyl.

The symbol $L^2$ is a linking group selected from the group consisting of a direct bond, $C_{1-3}$ alkylene, $C_{1-8}$ heteroalkyl, —O—, —NR$^s$, —C(O)—, —C(R$^s$)$_2$, —S(O)—, —S(O)$_2$—, —NR$^s$C(O)— and —NR$^s$S(O)$_2$—. The substituent R$^s$ is, at each occurrence, independently selected from the group consisting of hydrogen, $C_{1-8}$ alkyl, $C_{1-8}$ haloalkyl, $C_{3-6}$ cycloalkyl, $C_{2-8}$ alkenyl, $C_{2-8}$ alkynyl, $C_{6-10}$ aryl and $C_{5-10}$ heteroaryl; wherein the aliphatic portion of R$^s$ are optionally further substituted with from one to three members selected from the group consisting of —OH, —OR$^t$, —OC(O)NHR$^t$, —OC(O)N(R$^t$)$_2$, —SH, —SR$^t$, —S(O)R$^t$, —S(O)$_2$R$^t$, —SO$_2$NH$_2$, —S(O)$_2$NHR$^t$, —S(O)$_2$N(R$^t$)$_2$, —NHS(O)$_2$R$^t$, —NR$^t$S(O)$_2$R$^t$, —C(O)NH$_2$, —C(O)NHR$^t$, —C(O)N(R$^t$)$_2$, —C(O)R$^t$, —NHC(O)R$^t$, —NR$^o$C(O)R$^t$, —NHC(O)NH$_2$, —NR$^o$C(O)NH$_2$, —NR$^o$C(O)NHR$^t$, —NHC(O)NHR$^t$, —NR$^t$C(O)N(R$^t$)$_2$, —NHC(O)N(R$^t$)$_2$, —CO$_2$H, —CO$_2$R$^t$, —NHCO$_2$R$^t$, —NR$^t$CO$_2$R$^t$, —CN, —NO$_2$, —NH$_2$, —NHR$^t$, —N(R$^t$)$_2$, —NR$^t$S(O)NH$_2$ and —NR$^t$S(O)$_2$NHR$^t$, wherein each R$^t$ is independently an unsubstituted $C_{1-6}$ alkyl or $C_{1-6}$ haloalkyl The subscript n is an integer from 0-2.

DETAILED DESCRIPTION OF THE INVENTION

I. Abbreviation and Definitions

Figure 1A:
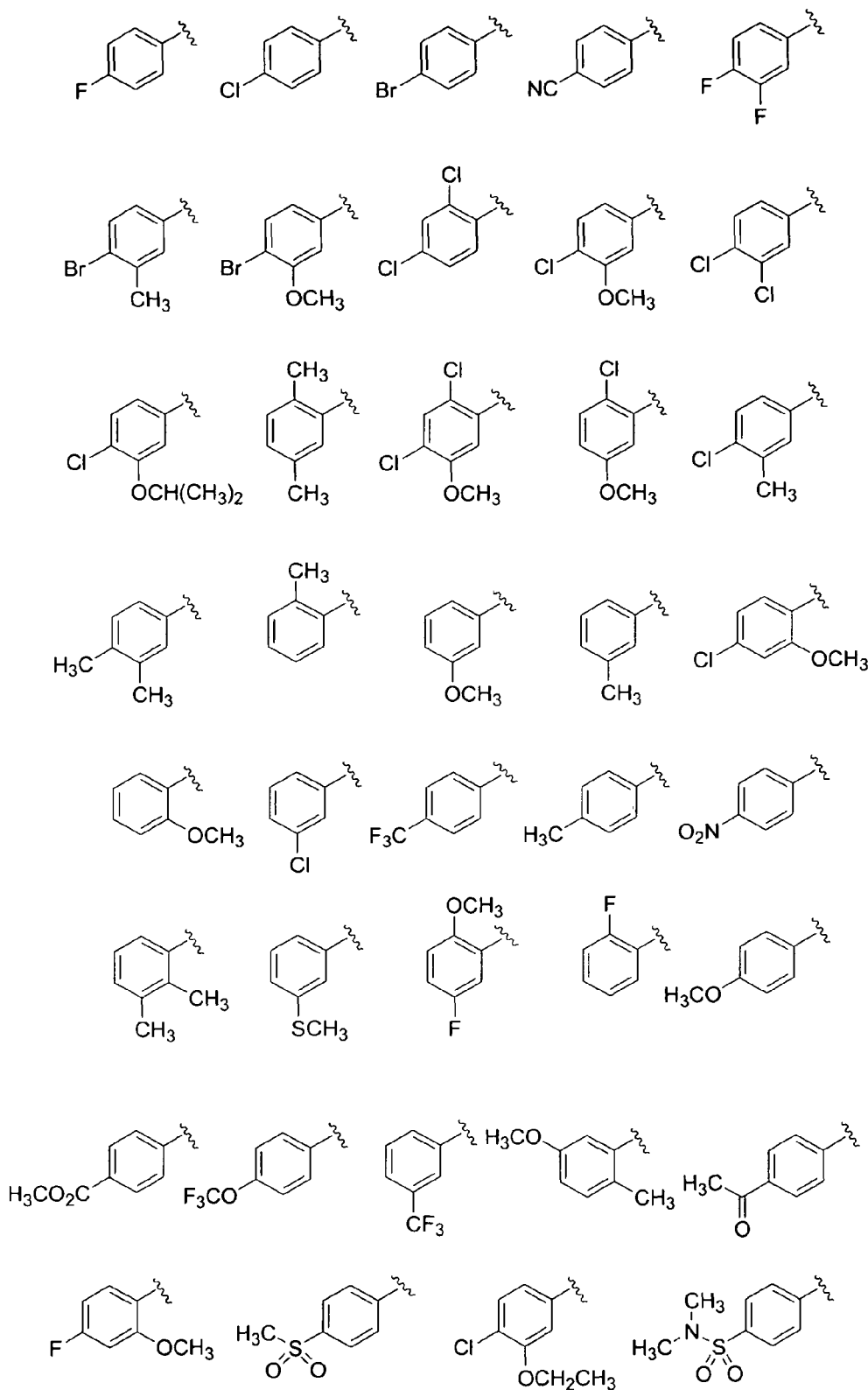
FIGS. 1A-1F show the structures of certain preferred substituted phenyl moieties comprising the $R^{2a-2e}$ substituents of the invention.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycyclic ring system. Non limiting examples of heterocycloalkyl groups include pyrrolidine, piperidiny, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S, S-oxide, piperazine, pyran, pyridone, 3-pyrroline, thiopyran, pyrone, tetrahydrofuran, tetrhydrothiophene, quinuclidine, and the like. A heterocycloalkyl group can be attached to the remainder of the molecule through a ring carbon or a heteroatom.

The term "alkylene" by itself or as part of another substituent means a divalent radical derived from an alkane, as exemplified by —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —NR$^a$R$^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like).

The above terms (e.g., "alkyl," "aryl" and "heteroaryl"), in some embodiments, will include both substituted and unsubstituted forms of the indicated radical. Preferred substituents for each type of radical are provided below. For brevity, the terms aryl and heteroaryl will refer to substituted or unsubstituted versions as provided below, while the term "alkyl" and related aliphatic radicals is meant to refer to unsubstituted version, unless indicated to be substituted.

Substituents for the alkyl radicals (including those groups often referred to as alkylene, alkenyl, alkynyl and cycloalkyl) can be a variety of groups selected from: -halogen, —OR', —NR'R", —SR', —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NH—C(NH$_2$)=NH, —NR$^a$C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such radical. R', R" and R''' each independently refer to hydrogen, unsubstituted $C_{1-8}$ alkyl, unsubstituted heteroalkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro($C_1$-$C_4$)alkoxy, and perfluoro($C_1$-$C_4$)alkyl, in a number ranging from zero to the total number of open valences on the aromatic ring system; and where R', R" and R''' are independently selected from hydrogen, $C_{1-8}$ alkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$-U-, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$-B-, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $C_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

II. General

The present invention derives from the discovery that compounds of Formula I act as potent antagonists of the CCR1 receptor. The compounds have in vivo anti-inflammatory activity. Accordingly, the compounds provided herein are useful in pharmaceutical compositions, methods for the treatment of CCR1-mediated diseases, and as controls in assays for the identification of competitive CCR1 antagonists.

III. Compounds

A. Embodiments of Formula I

In one aspect, the present invention provides compounds having the Formula I:

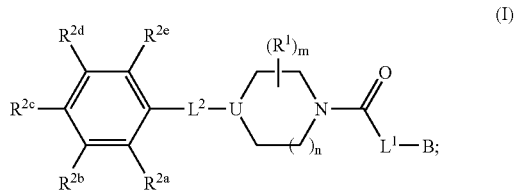

(I)

or pharmaceutically acceptable salts and N-oxides thereof, in which each $R^1$ is independently selected from the group consisting of $C_{1-8}$ alkyl, $C_{1-8}$ haloalkyl, $C_{3-6}$ cycloalkyl, $-CO_2R^a$, $-X^1CO_2R^a$, $-X^1SO_2R^a$, $-X^1SO_3R^a$, $-X^1OR^a$, $-COR^a$, $CONR^aR^b$, $-X^1NR^aNR^b$, $-X^1NR^aCOR^b$, $-X^1CONR^aR^b$, $X^1NR^aS(O)_2R^b$, $X^1S(O)_2NR^aR^b$ and $X^1S(O)_2R^a$. In Formula I, $X^1$ is $C_{1-4}$ alkylene and each $R^a$ and $R^b$ is independently selected from the group consisting of hydrogen, $C_{1-8}$ alkyl, $C_{1-8}$ haloalkyl and $C_{3-6}$ cycloalkyl. $R^a$ and $R^b$ when attached to the same nitrogen atom are optionally combined to form a 5- to 7-membered ring having from 0-2 heteroatoms selected from the group consisting of N, O and S. Optionally any two $R^1$ substituents attached to the same atom are optionally replaced with the substitutent =O, =NH, =NOH, =NR$^a$, =S or =CR$^a$R$^b$. Optionally, any two $R^1$ substituents attached to the same or adjacent carbon atoms are cyclized to form a 3- to 7-membered ring. The aliphatic portions of each $R^1$ substituent is optionally substituted with from one to three members selected from the group consisting of $-OH$, $-OR^m$, $-OC(O)NHR^m$, $-OC(O)N(R^m)_2$, $-SH$, $-SR^m$, $-S(O)R^m$, $-S(O)_2R^m$, $-SO_2NH_2$, $-S(O)_2NHR^m$, $-S(O)_2N(R^m)_2$, $-NHS(O)_2R^m$, $-NR^mS(O)_2R^m$, $-C(O)NH_2$, $-C(O)NHR^m$, $-C(O)N(R^m)_2$, $-C(O)R^m$, $-NHC(O)R^m$, $-NR^mC(O)R^m$, $-NHC(O)NH_2$, $-NR^mC(O)NH_2$, $-NR^mC(O)NHR^m$, $-NHC(O)NHR^m$, $-NR^mC(O)N(R^m)_2$, $-NHC(O)N(R^m)_2$, $-CO_2H$, $-CO_2R^m$, $-NHCO_2R^m$, $-NR^mCO_2R^m$, $-CN$, $-NO_2$, $-NH_2$, $-NHR^m$, $-N(R^m)_2$, $-NR^mS(O)NH_2$ and $-NR^mS(O)_2NHR^m$, in which each $R^m$ is independently an unsubstituted $C_{1-6}$ alkyl.

In one embodiment of the invention, each $R^1$ in Formula I is a substituent selected from the group consisting of $C_{1-8}$ alkyl, $C_{1-8}$ haloalkyl, $C_{3-6}$ cycloalkyl, $-CO_2R^a$, $-X^1CO_2R^a$, $-X^1SO_2R^a$, $-X^1SO_3R^a$ and $-X^1OR^a$. In one embodiment of the invention, each $R^1$ in Formula I is a substituent selected from the group consisting of $C_{1-8}$ alkyl, $C_{1-8}$ haloalkyl, $C_{3-6}$ cycloalkyl, $-CO_2R^a$, $-X^1CO_2R^a$, and $-X^1OR^a$. In another embodiment, $R^1$ in Formula I is a substituent independently selected from the group consisting of $C_{1-8}$ alkyl, $C_{1-8}$ haloalkyl and $C_{3-6}$ cycloalkyl. Within each of the above embodiments, the aliphatic portions of each of said $R^1$ substituents is optionally substituted with from one to three members selected from the group consisting of $-OH$, $-OR^m$, $-OC(O)NHR^m$, $-OC(O)N(R^m)_2$, $-SH$, $-SR^m$, $-S(O)R^m$, $-S(O)_2R^m$, $-SO_2NH_2$, $-S(O)_2NHR^m$, $-S(O)_2N(R^m)_2$, $-NHS(O)_2R^m$, $-NR^mS(O)_2R^m$, $-C(O)NH_2$, $-C(O)NHR^m$, $-C(O)N(R^m)_2$, $-C(O)R^m$, $-NHC(O)R^m$, $-NR^mC(O)R^m$, $-NHC(O)NH_2$, $-NR^mC(O)NH_2$, $-NR^mC(O)NHR^m$, $-NHC(O)NHR^m$, $-NR^mC(O)N(R^m)_2$, $-NHC(O)N(R^m)_2$, $-CO_2H$, $-CO_2R^m$, $-NHCO_2R^m$, —NR'''CO$_2$R''', —CN, —NO$_2$, —NH$_2$, —NHR''', —N(R''')$_2$, —NR'''S(O)NH$_2$ and —NR'''S(O)$_2$NHR''', wherein each R''' is independently an unsubstituted C$_{1-6}$ alkyl.

In another embodiment, R$^1$, when present, is selected from the group consisting of —CO$_2$R$^a$ or C$_{1-4}$ alkyl, optionally substituted with OH, —OR''', —S(O)$_2$R''', —CO$_2$H or —CO$_2$R'''. In yet another embodiment, R$^1$, when present, is selected from the group consisting of —CO$_2$H or C$_{1-4}$ alkyl, optionally substituted with OH, —OR''', —S(O)$_2$R''', —CO$_2$H or —CO$_2$R'''. In another embodiment, R$^1$ is selected from the group consisting of —CO$_2$H, —CO$_2$CH$_3$ and —CH$_3$.

The subscript m in Formula I is an integer from 0-4. In one embodiment, the subscript m, in Formula I, is an integer from 0-2. In another embodiment the subscript m is an integer from 0-1. In another embodiment, R$^1$ is methyl; and m is from 0-2. In another embodiment, R$^1$ is selected from the group consisting of —CO$_2$H, —CO$_2$CH$_3$ and —CH$_3$; and m is an integer from 0-1.

In Formula I, the symbols R$^{2a}$, R$^{2b}$, R$^{2c}$, R$^{2d}$ and R$^{2e}$ at each occurrence are each independently selected from the group consisting of hydrogen, halogen, cyano, heteroaryl, —NO$_2$, —CO$_2$R$^c$, —C(O)NR$^c$R$^d$, —C(O)R$^c$, —S(O)R$^e$, —S(O)$_2$R$^e$, —NR$^c$S(O)$_2$R$^e$, —R$^e$, —C(NOR$^c$)R$^d$, —C(NR$^c$V)=NV, —N(V)C(R$^c$)=NV, —NR$^d$C(O)$_2$R$^e$, —NR$^c$C(O)NR$^c$R$^d$, —NH—C(NH$_2$)=NH, —NR$^e$C(NH$_2$)=NH, —NH—C(NH$_2$)=NR$^e$, —NH—C(NHR$^e$)=NH, —X$^2$C(NR$^c$V)=NV, —X$^2$N(V)C(R$^c$)=NV —X$^2$C(NOR$^c$)R$^d$, —X$^2$C(NR$^c$V)=NV, —X$^2$N(V)C(R$^c$)=NV, —NR$^c$R$^d$, —X$^2$SR$^c$, —X$^2$CN, —X$^2$NO$_2$, —X$^2$CO$_2$R$^c$, —X$^2$CONR$^c$R$^d$, —X$^2$C(O)R$^c$, —X$^2$OC(O)NR$^c$R$^d$, —X$^2$NR$^d$C(O)R$^c$, —X$_2$NR$^d$C(O)$_2$R$^e$, —X$^2$NR$^c$C(O)NR$^c$R$^d$, —X$^2$NH—C(NH$_2$)=NH, —X$^2$NR$^e$C(NH$_2$)=NH, —X$^2$NH—C(NH$_2$)=NR$^e$, —X$^2$NH—C(NHR$^e$)=NH, —X$^2$S(O)R$^e$, —X$^2$S(O)$_2$R$^e$, —X$^2$NR$^c$S(O)$_2$R$^e$, —X$^2$S(O)$_2$NR$^c$R$^d$, —X$^2$N$_3$, OR$^c$, SR$^c$, NR$^d$C(O)R$^c$, —NR$^d$C(O)$_2$R$^e$, —S(O)$_2$NR$^c$R$^d$, —X$^2$OR$^c$, —O—X$^2$OR$^c$, —X$^2$NR$^c$R$^d$, —OX$^2$NR$^c$R$^d$ and —NR$_d$—X$^2$CO$_2$R$^c$. The symbol X$^2$ is C$_{1-4}$ alkylene and each R$^c$ and R$^d$ is independently selected from hydrogen, C$_{1-8}$ alkyl, C$_{1-8}$ haloalkyl, C$_{3-6}$ cycloalkyl, or optionally, R$^c$ and R$^d$ when attached to the same nitrogen atom can be combined with the nitrogen atom to form a five or six-membered ring having from 0 to 2 additional heteroatoms as ring members. Each R$^e$ is independently selected from the group consisting of C$_{1-8}$ alkyl, C$_{1-8}$ haloalkyl, C$_{3-6}$ cycloalkyl, C$_{2-8}$ alkenyl, C$_{2-8}$ alkynyl, aryl and heteroaryl. Each of R$^c$, R$^d$ and R$^e$ is optionally further substituted with from one to three members selected from the group consisting of —OH, —OR'', —OC(O)NHR'', —OC(O)N(R'')$_2$, —SH, —SR'', —S(O)R'', —S(O)$_2$R'', —SO$_2$NH$_2$, —S(O)$_2$NHR'', —S(O)$_2$N(R'')$_2$, —NHS(O)$_2$R'', —NR''S(O)$_2$R'', —C(O)NH$_2$, —C(O)NHR'', —C(O)N(R'')$_2$, —C(O)R'', —NHC(O)R'', —NR''C(O)R'', —NHC(O)NH$_2$, —NR''C(O)NH$_2$, —NR''C(O)NHR'', —NHC(O)NHR'', —NR''C(O)N(R'')$_2$, —NHC(O)N(R'')$_2$, —CO$_2$H, —CO$_2$R'', —NHCO$_2$R'', —NR''CO$_2$R'', —CN, —NO$_2$, —NH$_2$, NHR'', —N(R'')$_2$, —NR''S(O)NH$_2$ and —NR''S(O)$_2$NHR'', wherein each R'' is independently an unsubstituted C$_{1-6}$ alkyl, and wherein V is independently selected from the group consisting of —R$^c$, —CN, —CO$_2$R$^e$ and —NO$_2$.

In one embodiment, the symbols R$^{2a}$, R$^{2b}$, R$^{2c}$, R$^{2d}$ and R$^{2e}$ in Formula I are each is independently selected from the group consisting of hydrogen, halogen, cyano, heteroaryl, —NO$_2$, —CO$_2$R$^c$, —CONR$^c$R$^d$, —C(O)R$^c$, —S(O)R$^e$, —S(O)$_2$R$^e$, R$^e$, C(NOR$^c$)R$^d$, C(NR$^c$V)=NV, —N(V)C(R$^c$)=NV, —X$^2$C(NOR$^c$)R$^d$, —X$^2$C(NR$^c$V)=NV, —X$^2$N(V)C(R$^c$)=NV, —X$^2$NR$^c$R$^d$, —X$^2$SR$^c$, —X$^2$CN, —X$^2$NO$_2$, —X$^2$CO$_2$R$^c$, —X$^2$CONR$^c$R$^d$, —X$^2$C(O)R$^c$, —X$^2$OC(O) NR$^c$R$^d$, —X$^2$NR$^d$C(O)R$^c$, —X$^2$NR$^d$C(O)$_2$R$^e$, —X$^2$NR$^c$C(O)NR$^c$R$^d$, —X$^2$NH—C(NH$_2$)=NH, X$^2$NR$^e$C(NH$_2$)=NH, —X$^2$NH—C(NH$_2$)=NR$^e$, —X$^2$NH—C(NHR$^e$)=NH, —X$^2$S(O)R$^e$, —X$^2$S(O)$_2$R$^e$, —X$^2$NR$^c$S(O)$_2$R$^e$, —X$^2$S(O)$_2$NR$^c$R$^d$ and —X$^2$N$_3$.

In one embodiment, the R$^{2a}$ substituent in Formula I is selected from the group consisting of hydrogen, F, Cl, Br, I, —CO$_2$R$^c$, —CONR$^c$R$^d$, —CN, a 5- to 6-membered heteroaryl, —X$_2$NR$^c$R$^d$, —C(NOR$^c$)R$^d$. In yet another embodiment, R$^{2a}$ is hydrogen. In other embodiments, the R$^{2a}$ substituent in Formula I is selected from the group consisting of F, Cl, Br, I, —CO$_2$Me, —CONH$_2$, CN, oxazolyl, —CH$_2$NH$_2$, —CH$_2$NHMe, —CH$_2$NMe$_2$ and —CH=N—OH. In yet another embodiment, in compounds having Formulae I, the R$^{2a}$ substituent is selected from the group consisting of hydrogen, F, Cl, Br and I. In another embodiment, R$^{2b}$ and R$^{2e}$ are each hydrogen.

In another embodiment, R$^{2b}$ is hydrogen. In another embodiment, R$^{2b}$ is halogen or OR$^c$. In another embodiment, R$^{2b}$ is fluoro, chloro, bromo, iodo, methoxy, or ethoxy.

In another embodiment, the symbols R$^{2c}$ and R$^{2d}$ in Formula I are each substituents independently selected from the group consisting of hydrogen, halogen, —OR$^c$, —SR$^c$, —OC(O)R$^c$, —NR$^c$R$^d$, —R$^e$, —CN, —NO$_2$, —CO$_2$R$^c$, —C(O)R$^c$, NR$^d$C(O)R$^c$, —NR$^d$C(O)$_2$R$^e$, —S(O)$_2$R$^e$, S(O)$_2$NR$^c$R$^d$, —X$^2$OR$^c$, —O—X$^2$OR$^c$, —X$^2$NR$^c$R$^d$, —O—X$^2$NR$^c$R$^d$ and —NR$_d$—X$^2$ CO$_2$R$^c$. In certain aspects of this embodiment, R$^{2c}$ and R$^{2d}$ are each independently selected from the group consisting of hydrogen, halogen, F, Cl, Br, I and OR$^c$. In another aspect of this embodiment, R$^{2d}$ is hydrogen and R$^{2c}$ is selected from the group consisting of halogen, F, Cl, Br, I and OR$^c$.

In one embodiment, the symbols R$^{2a}$, R$^{2c}$ and R$^{2d}$ in Formula I are each independently selected from the group consisting of hydrogen, halogen, cyano, heteroaryl, —NO$_2$, —CO$_2$R$^c$, CONR$^c$R$^d$, —C(O)R$^c$, —S(O)R$^e$, —S(O)$_2$R$^e$, R$^e$, —C(NOR$^c$)R$^d$, —C(NR$^c$V)=NV, —N(V)C(R$^c$)=NV, —X$^2$C(NOR$^c$)R$^d$, —X$^2$C(NR$^c$V)=NV, —X$^2$N(V)C(R$^c$)=NV, —X$^2$NR$^c$R$^d$, —X$^2$SR$^c$, —X$^2$CN, —X$^2$NO$_2$, —X$^2$CO$_2$R$^c$, —X$^2$CONR$^c$R$^d$, —X$^2$C(O)R$^c$, —X$^2$OC(O)NR$^c$R$^d$, —X$^2$NR$^d$C(O)R$^c$, —X$^2$NR$^d$C(O)$_2$R$^e$, —X$^2$NR$^c$C(O)NR$^c$R$^d$, —X$^2$NH—C(NH$_2$)=NH, —X$^2$NR$^e$C(NH$_2$)=NH, —X$^2$NH—C(NH$_2$)=NR$^e$, —X$^2$NH—C(NHR$^e$)=NH, —X$^2$S(O)R$^e$, —X$^2$S(O)$_2$R$^e$, —X$^2$NR$^c$S(O)$_2$R$^e$, —X$^2$S(O)$_2$NR$^c$R$^d$ and —X$^2$N$_3$; and R$^{2b}$ and R$^{2e}$ are each hydrogen. In certain aspects of this embodiment, R$^{2a}$ is selected from the group consisting of hydrogen, halogen, —CO$_2$R$^c$, —C(O)NR$^c$R$^d$, —CN, oxazolyl, —X$^2$N$^c$R$^d$ and —C(NOR$^c$)R$^d$; R$^{2b}$ and R$^{2e}$ are each hydrogen; R$^{2c}$ is selected from the group consisting of halogen, —CN, —NO$_2$, —CO$_2$R$^c$, —C(O)NR$^c$R$^d$, —C(O)R$^c$ and —S(O)$_2$R$^e$; and R$^{2d}$ is selected from the group consisting of hydrogen, —SR$^c$, —O—X$^2$—OR$^c$, —X$^2$—OR$^c$, —R$^e$, —OR$^c$, —NR$^c$R$^d$, —NR$^c$S(O)$_2$R$^e$ and —NR$^d$C(O)R$^c$. In another aspect of this embodiment, R$^{2a}$ is hydrogen.

In another embodiment, R$^{2a}$ and R$^{2b}$ in Formula I are each independently selected from the group consisting of hydrogen, halogen, cyano, heteroaryl, —NO$_2$, —CO$_2$R$^c$, —CONR$^c$R$^d$, —C(O)R$^c$, —S(O)R$^e$, —S(O)$_2$R$^e$, —R$^e$, —C(NOR$^c$)R$^d$, —C(NR$^c$V)=NV, —N(V)C(R$^c$)=NV, —X$^2$C(NOR$^c$)R$^d$, —X$^2$C(NR$^c$V)=NV, —X$^2$N(V)C(R$^c$)=NV, X$^2$ NR$^c$R$^d$, —X$^2$SR$^c$, —X$^2$CN, —X$^2$NO$_2$, —X$^2$CO$_2$R$^c$, —X$^2$CONR$^c$R$^d$, —X$^2$C(O)R$^c$, —X$^2$OC(O)NR$^c$R$^d$, —X$^2$NR$^d$C(O)R$^c$, —X$^2$NR$^d$C(O)$_2$R$^e$, —X$^2$NR$^c$C(O)NR$^c$R$^d$, —X$^2$NH—C(NH$_2$)=NH, —X$^2$NR$^e$C(NH$_2$)=NH, —X$^2$NH—C(NH$_2$)=NR$^e$, —X$^2$NH—C(NHR$^e$)=NH, —$X^2S(O)R^e$, —$X^2S(O)_2R^e$, —$X^2NR^cS(O)_2R^e$, —$X^2S(O)_2NR^cR^d$ and —$X^2N_3$; and $R^{2c}$, $R^{2d}$ and $R^{2e}$ are each hydrogen. In another embodiment, $R^{2b}$ is halogen or $OR^c$. In another embodiment, $R^{2b}$ is fluoro, chloro, bromo, iodo, methoxy, or ethoxy.

Figure 1B:
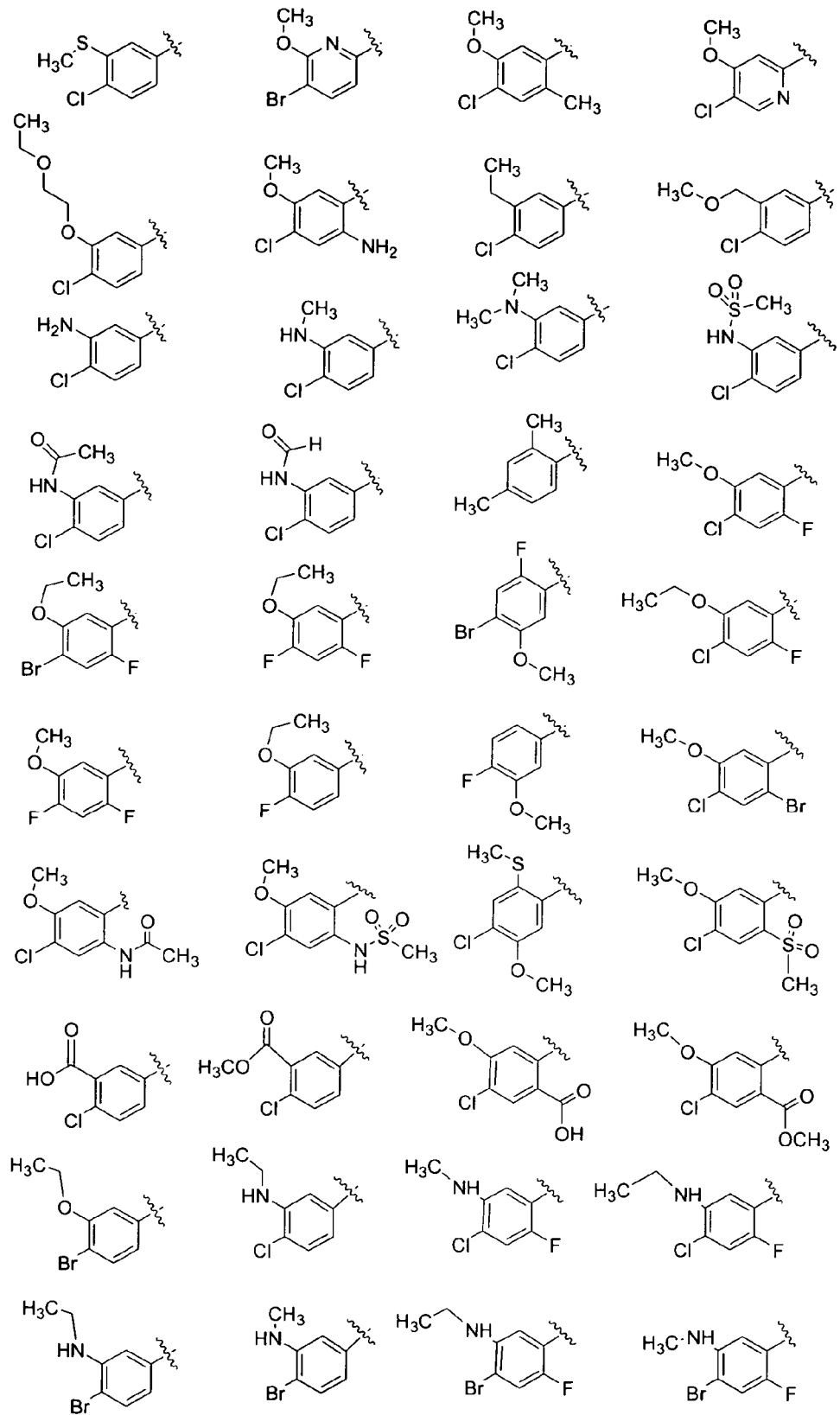
Figure 1C:
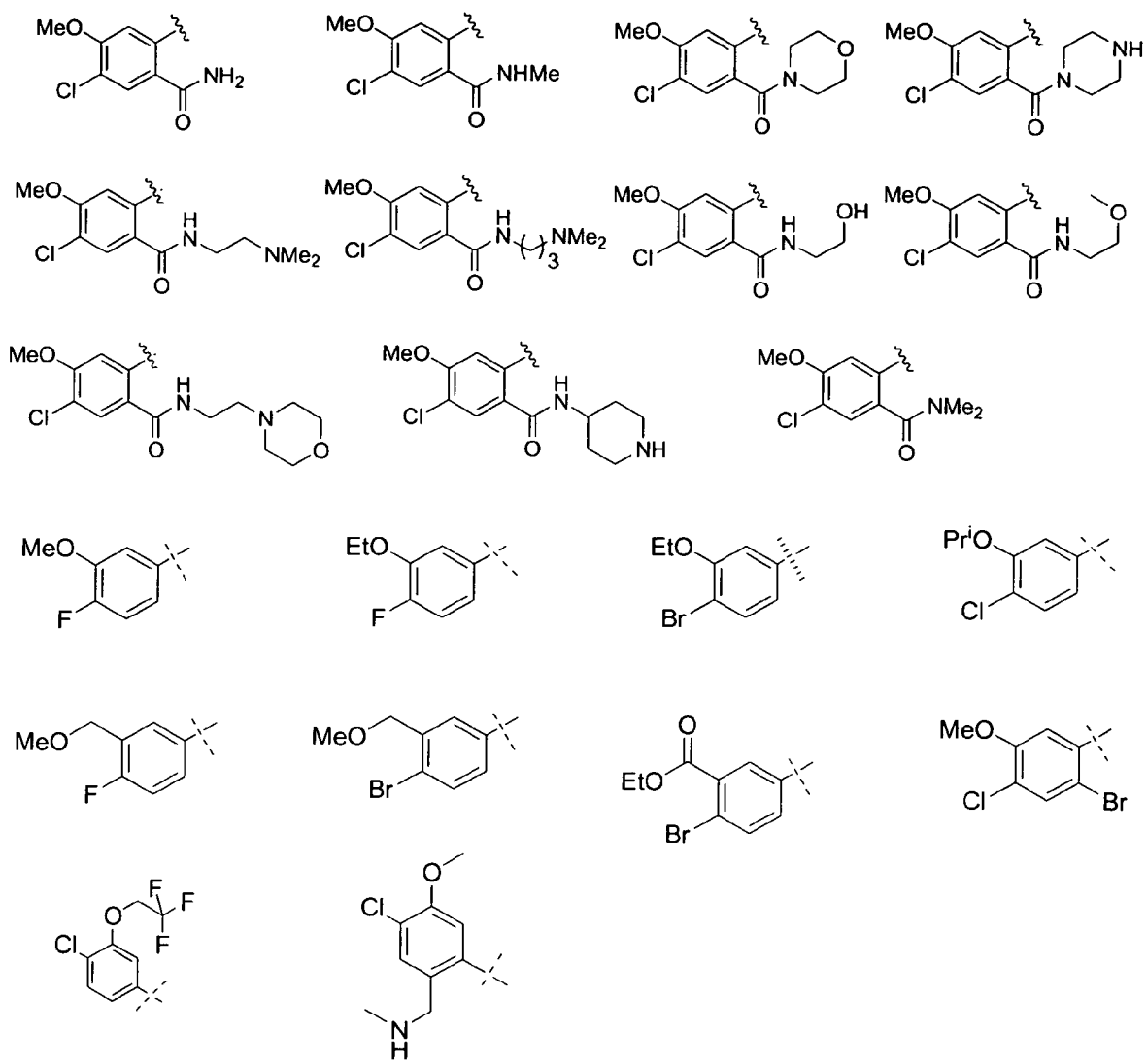
Figure 1D:
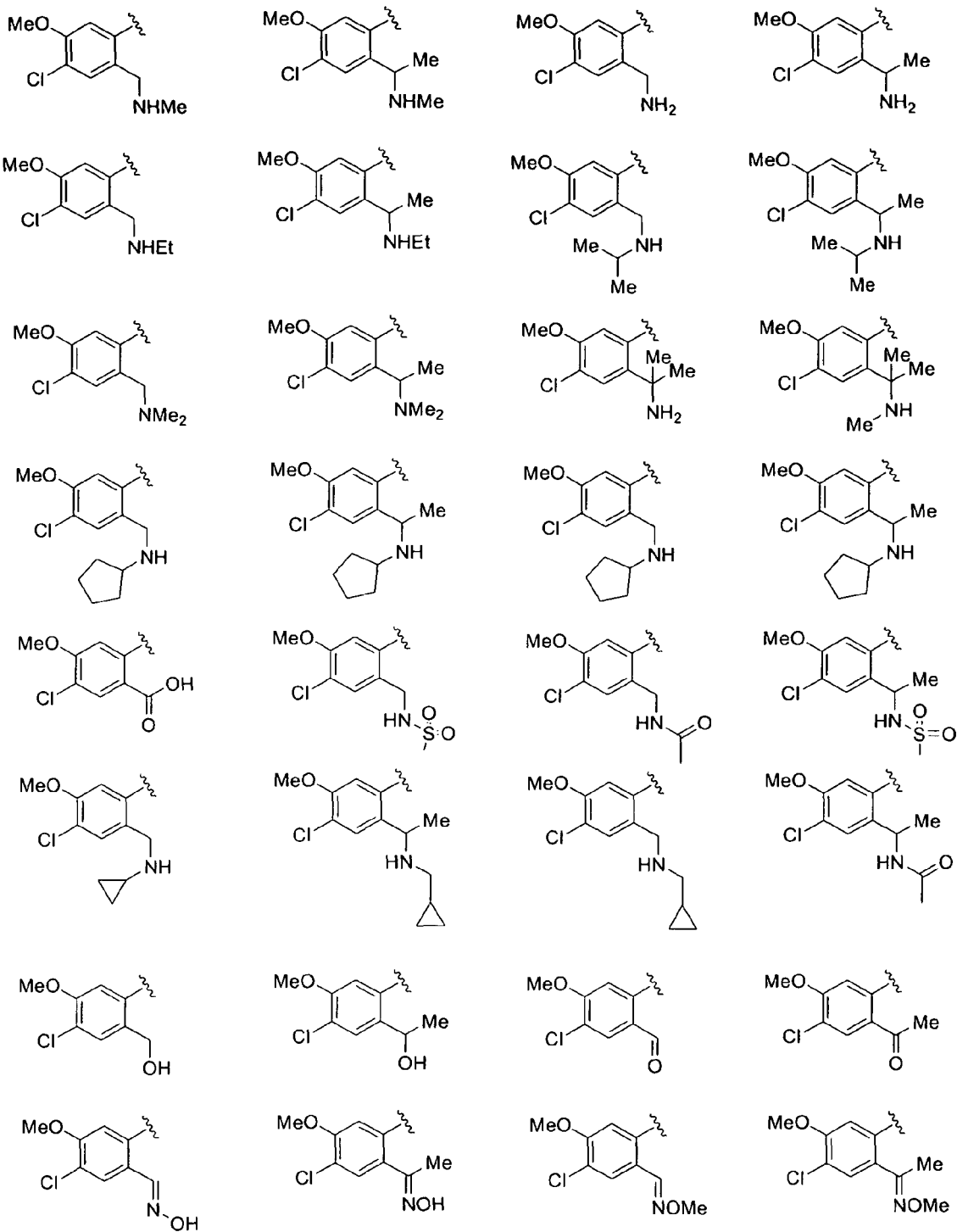
Figure 1E:
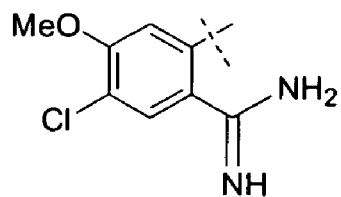
Figure 1E:
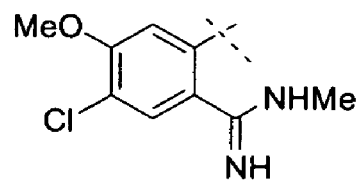
Figure 1E:
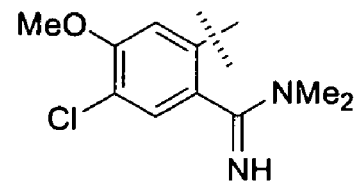
Figure 1E:
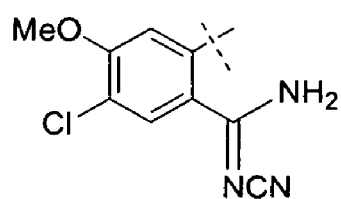
Figure 1E:
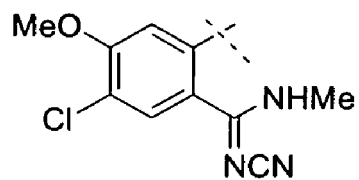
Figure 1E:
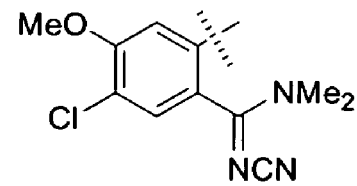
Figure 1E:
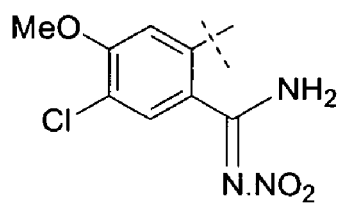
Figure 1E:
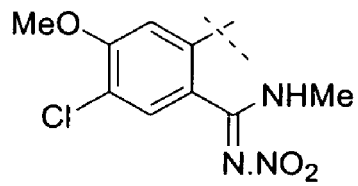
Figure 1E:
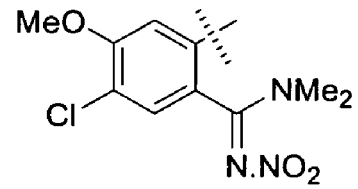
Figure 1E:
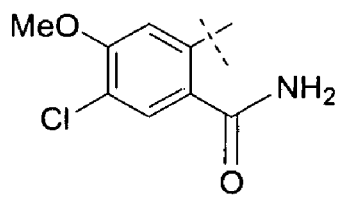
Figure 1E:
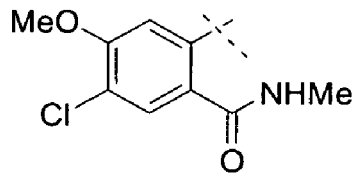
Figure 1E:
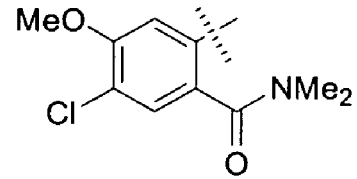
Figure 1F:
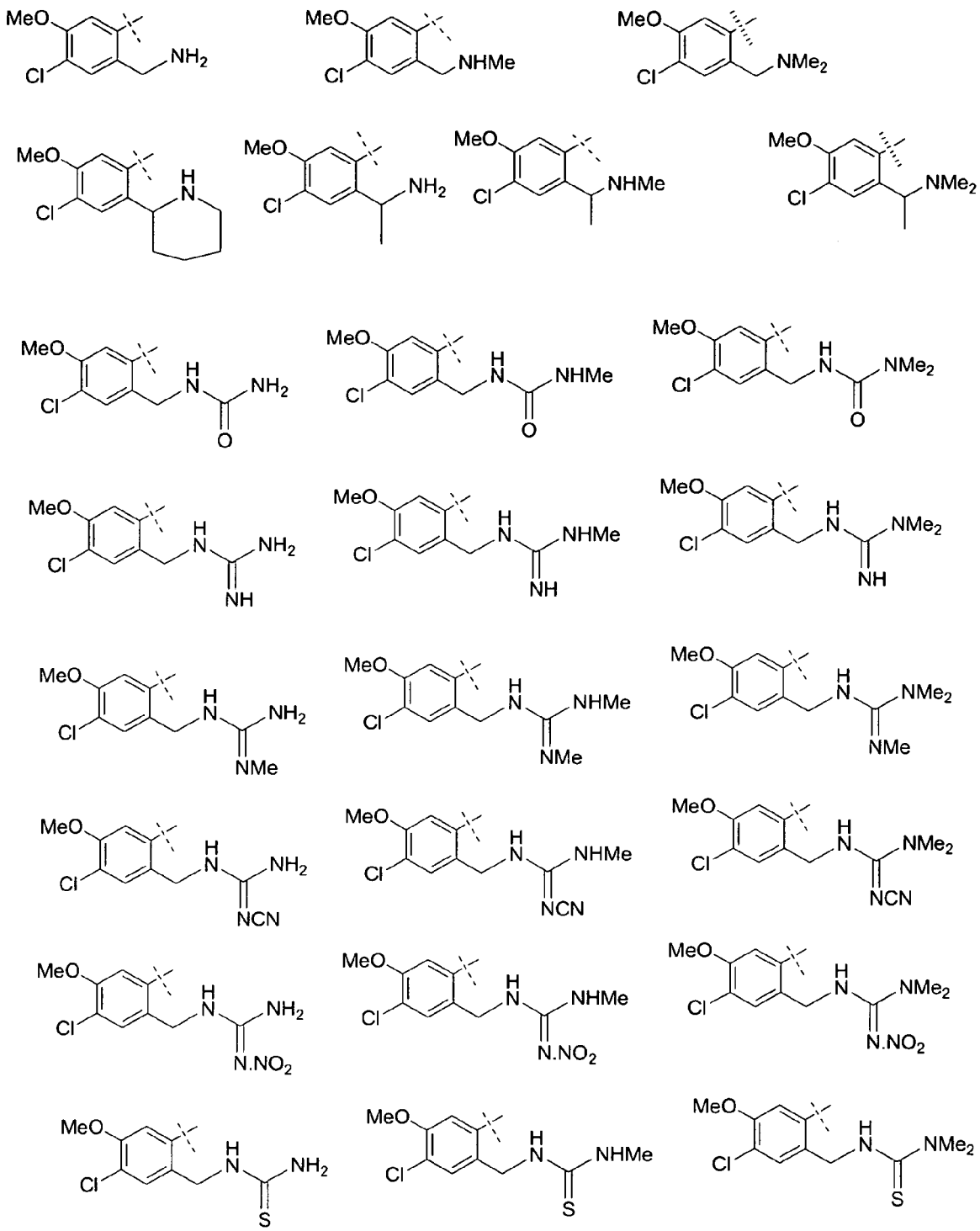

In another embodiment, the phenyl ring bearing the $R^{2a-2e}$ substituents is independently selected from each of the substituted phenyl moieties shown in FIGS. 1A-1F.

Within each of the above embodiments, the aliphatic portions of $R^{2a-2e}$ are optionally substituted with from one to three members selected from the group consisting of —OH, —$OR''$, —$OC(O)NHR''$, —$OC(O)N(R'')_2$, —SH, —$SR''$, —$S(O)R''$, —$S(O)_2R''$, —$SO_2NH_2$, —$S(O)_2NHR''$, —$S(O)_2N(R'')_2$, —$NHS(O)_2R''$, —$NR''S(O)_2R''$, —$C(O)NH_2$, —$C(O)NHR''$, —$C(O)N(R'')_2$, —$C(O)R''$, —$NHC(O)R''$, —$NR''C(O)R''$, —$NHC(O)NH_2$, —$NR''C(O)NH_2$, —$NR''C(O)NHR''$, —$NHC(O)NMR''$, —$NR''C(O)N(R'')_2$, —$NHC(O)N(R'')_2$, —$CO_2H$, —$CO_2R''$, —$NHCO_2R''$, —$NR''CO_2R''$, —CN, —$NO_2$, —$NH_2$, —$NHR''$, —$N(R'')_2$, —$NR''S(O)NH_2$ and —$NR''S(O)_2NHR''$, wherein each $R''$ is independently an unsubstituted $C_{1-6}$ alkyl, and wherein V is independently selected from the group consisting of —$R^c$, —CN, —$CO_2R^e$ and —$NO_2$.

The symbol B in Formula I represents a monocyclic (-$B^1$) or bicyclic (-$B^1$-$B^2$) ring system, wherein the monocyclic or bicyclic ring system is attached to the remainder of Formula I through the $B^1$ ring. The $B^1$ ring is a 5- to 7-membered non-aromatic nitrogen containing heterocyclic ring optionally having 1-2 additional heteroatom ring members selected from the group consisting of N, O, S, S(O) and $S(O)_2$, and optionally having up to two double bonds; and $B^2$ is selected from the group consisting of phenyl, pyridinyl, pyrimidinyl, pyrazinyl and pyridazinyl. When B is a bicyclic ring system, then $B^1$ and $B^2$ are fused or connected with a single bond. The $B^1$ and $B^2$ rings are both each independently further substituted with 0 to 5 $R^3$ substitutents. In certain embodiment, the $B^1$ and $B^2$ rings of the symbol B are each independently further substituted with 0 to 4 $R^3$ substitutents, preferably 0-3, or preferably 0-2 $R^3$ substitutents. At each occurrence, $R^3$ is independently selected from the group consisting of hydrogen, halogen, —$OR^f$, —$OC(O)R^f$, —$NR^fR^g$, —$SR^f$, —$R^h$, —CN, —$NO_2$, —$CO_2R^f$, —$CONR^fR^g$, —$C(O)R^f$, —$OC(O)NR^fR^g$, —$NR^gC(O)R^f$, —$NR^gC(O)_2R^h$, —$NR^f$—$C(O)NR^fR^g$, —$NR^fR^g$, —NH—$C(NH_2)$=NH, —$NR^hC(NH_2)$=NH, —NH—$C(NH_2)$=$NR^h$, —$C(NR^fR^g)$=$NOR^f$, —$S(O)_3R^h$, $X^3S(O)_3R^f$, —NH—$C(NHR^h)$=NH, —$S(O)R^h$, —$S(O)_2R^h$, —$NR^fS(O)_2R^h$, —$S(O)_2NR^fR^g$, —$NR^fS(O)_2R^h$, —$NR^fS(O)_2NR^fR^g$, —$N_3$, —$X^3OR^f$, —$X^3OC(O)R^f$, —$X^3NR^fR^g$, —$X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2R^h$, —$X^3NR^f$—$C(O)NR^fR^g$, —$X^3NH$—$C(NH_2)$=NH, —$X^3NR^hC(NH_2)$=NH, —$X^3NH$—$C(NH_2)$=$NR^h$, —$X^3NH$—$C(NHR^h)$=NH, —$X^3S(O)R^h$, —$X^3S(O)_2R^h$, —$X^3NR^fS(O)_2R^h$, —$X^3S(O)_2NR^fR^g$, —Y, —$X^3Y$ and —$X^3N_3$, wherein Y is a five to ten-membered aryl, heteroaryl or heterocycloalkyl ring, optionally substituted with from one to three substitutents selected from the group consisting of halogen, —$OR^f$, —$NR^fR^g$, —$R^h$, —$SR^f$, —CN, —$NO_2$, —$CO_2R^f$, —$CONR^fR^g$, —$C(O)R^f$, —$NR^gC(O)R^f$, —$S(O)R^h$, —$S(O)_2R^h$, —$NR^fS(O)_2R^h$, —$S(O)_2NR^fR^g$, —$X^3OR^f$, —$X^3NR^fR^g$, —$X^3NR^fS(O)_2R^h$, —$X^3CO_2R^f$, —$X^3CONR^fR^g$, —$X^3C(O)R^f$, —$X^3NR^gC(O)R^f$, —$X^3S(O)R^h$, —$X^3S(O)_2R^h$, and —$X^3S(O)_2NR^fR^g$. Any two $R^3$ substituents attached to the same atom on $B^1$ are optionally replaced with the substituent =O, =NH, =NOH, =$NR^f$, =S or =$CR^fR^g$. Furthermore, when B is a monocyclic ring system (-$B^1$), $R^3$ is not —Y. Optionally any two $R^3$ substituent located on adjacent atoms of $B^1$ or $B^2$ may be combined to form a 5- or 6-membered ring. Each $X^3$ is independently selected from the group consisting of $C_{1-4}$ alkylene, $C_{2-4}$ alkenylene and $C_{2-4}$ alkynylene; and each $R^f$ and $R^g$ substituent is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl and aryloxy-$C_{1-4}$ alkyl, or when attached to the same nitrogen atom can be combined with the nitrogen atom to form a five or six-membered ring having from 0 to 2 additional heteroatoms as ring members. Each $R^h$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl and aryloxy-$C_{1-4}$ alkyl, wherein the aliphatic portions of $X^3$, $R^f$, $R^g$ and $R^h$ are optionally further substituted with from one to three members selected from the group consisting of —OH, —$OR^o$, —$OC(O)NHR^o$, —$OC(O)N(R^o)_2$, —SH, —$SR^o$, —$S(O)R^o$, —$S(O)_2R^o$, —$SO_2NH_2$, —$S(O)_2NHR^o$, —$S(O)_2N(R^o)_2$, —$NHS(O)_2R^o$, —$NR^oS(O)_2R^o$, —$C(O)NH_2$, —$C(O)NHR^o$, —$C(O)N(R^o)_2$, —$C(O)R^o$, —$NHC(O)R^o$, —$NR^oC(O)R^o$, —$NHC(O)NH_2$, —$NR^oC(O)NH_2$, —$NR^oC(O)NHR^o$, —$NHC(O)NHR^o$, —$NR^oC(O)N(R^o)_2$, —$NHC(O)N(R^o)_2$, —$CO_2H$, —$CO_2R^o$, —$NHCO_2R^o$, —$NR^oCO_2R^o$, —CN, —$NO_2$, —$NH_2$, —$NHR^o$, —$N(R^o)_2$, —$NR^oS(O)NH_2$ and —$NR^oS(O)_2NHR^o$, wherein $R^o$ is unsubstituted $C_{1-6}$ alkyl.

In one embodiment, the substituent $R^3$ on the B group of Formula I, at each occurrence, is independently selected from the group consisting of hydrogen, halogen, —$OR^f$, —$OC(O)R^f$, —$NR^fR^g$, —$SR^f$, —$R^h$, —CN, —$NO_2$, —$CO_2R^f$, —$CONR^fR^g$, —$C(O)R^f$, —$OC(O)NR^fR^g$, —$NR^gC(O)R^f$, —$NR^gC(O)_2R^h$, —$NR^f$—$C(O)NR^fR^g$, —$S(O)R^h$, —$S(O)_2R^h$, —$S(O)_3R^h$, —$NR^fS(O)_2R^h$, —$S(O)_2NR^fR^g$, —$NR^fS(O)_2NR^fR^g$, —$X^3$ $OR^f$, —$X^3NR^fR^g$, $X^3SR^f$, —$X^3S(O)_2R^h$, —$X^3S(O)_3R^h$, —$X^3S(O)_2NR^fR^g$, —$X^3CN$, —$C(C$=$NOR^f)NR^fR^g$, —$X^3CO_2R^f$, —$X^3CONR^fR^g$, —$X^3C(O)R^f$, —$X^3NR^gC(O)R^f$, —$X^3NR^gC(O)_2R^h$, —Y, —$X^3Y$ and —$X^3N_3$. The symbol Y is a five or six-membered aryl, a five or six membered heteroaryl, or a three to eight membered heterocycloalkyl ring, optionally substituted with from one to three substitutents selected from the group consisting of halogen, —$OR^f$, —$NR^fR^g$, —$R^h$, —$SR^f$, —CN, —$NO_2$, —$CO_2R^f$, —$CONR^fR^g$, —$C(O)R^f$, —$NR^gC(O)R^f$, —$S(O)R^h$, —$S(O)_2R^h$, —$NR^fS(O)_2R^h$ and —$S(O)_2NR^fR^g$. $X^3$ is independently $C_{1-4}$ alkylene. The symbols $R^f$ and $R^g$ are independently selected from hydrogen, $C_{1-8}$ alkyl, $C_{1-8}$ haloalkyl and $C_{3-6}$ cycloalkyl, and each $R^h$ is independently selected from the group consisting of $C_{1-8}$ alkyl, $C_{1-8}$ haloalkyl and $C_{3-6}$ cycloalkyl.

In another embodiment of the invention, the $R^3$ substituent in the B group of Formula I, at each occurrence, is a member independently selected from the group consisting of hydrogen, halogen, —$OR^f$, —$NR^fR^g$, —$R^h$, —CN, and —Y, wherein Y is a five to six-membered aryl ring, a five to six-membered heteroaryl ring, or a three to eight-membered heterocycloalkyl ring selected from the group consisting of homopiperidinyl, morpholinyl, thiomorpholinyl, pyrrolidinyl, piperidinyl, azetidinyl, pyranyl, tetrahydrofuranyl, piperazinyl, phenyl, pyridyl, pyrimidinyl, oxadiazolyl, oxazolyl and thiazolyl, optionally substituted with from one to three substitutents selected from the group consisting of halogen, —$OR^f$, —$NR^fR^g$, —$R^h$, —CN, wherein each $R^f$ and $R^g$ is independently selected from hydrogen, $C_{1-6}$ alkyl, $C_{1-6}$ haloalkyl and $C_{3-6}$ cycloalkyl, and each $R^h$ is independently selected from the group consisting of $C_{1-6}$ alkyl, $C_{1-6}$ haloalkyl and $C_{3-6}$ cycloalkyl In another embodiment of the invention, the $R^3$ substituent in the B group of Formula I, at each occurrence, is selected from the group consisting of —Y and —$X^3$—Y, wherein Y is selected from the group consisting of homopiperidinyl, morpholinyl, thiomorpholinyl, pyrrolidinyl, piperidinyl, azetidinyl, pyranyl, tetrahydrofuranyl, piperazinyl, phenyl, thienyl, furanyl, pyridyl, pyrimidinyl, pyrazinyl, pyrrolyl, pyridizinyl, pyrazolyl, imidazolyl, thiazolyl, oxazolyl, isoxazolyl, isothiazolyl, triazolyl, tetrazolyl and oxadiazolyl, which is optionally substituted with from one to three substituents independently selected from the group consisting of halogen, —$OR^f$, —$NR^fR^g$, —$COR^f$, —$CO_2R^f$, —$CONR^fR^g$, —$NO_2$, —$R^h$ and —CN, wherein $R^f$ and $R^g$ are each independently selected from the group consisting of H, $C_{1-8}$ alkyl, $C_{3-6}$ cycloalkyl and $C_{1-8}$ haloalkyl, and each $R^h$ is independently selected from the group consisting of $C_{1-8}$ alkyl, $C_{3-6}$ cycloalkyl and $C_{1-8}$ haloalkyl. In certain aspects of this embodiment, the symbol Y is selected from the group consisting of phenyl, pyridyl, oxazolyl, pyrimidinyl, oxadiazolyl, and thiazolyl, each of which is optionally substituted with from one to three substituents independently selected from the group consisting of halogen, —$OR^f$, —$NR^fR^g$, —$COR^f$, —$CO_2R^f$, —$CONR^fR^g$, —$NO_2$, —$R^h$ and —CN, wherein $R^f$ and $R^g$ are each independently selected from the group consisting of H, $C_{1-8}$ alkyl, $C_{3-6}$ cycloalkyl and $C_{1-8}$ haloalkyl, and each $R^h$ is independently selected from the group consisting of $C_{1-8}$ alkyl, $C_{3-6}$ cycloalkyl and $C_{1-8}$ haloalkyl.

In yet another embodiment of the invention, the $R^3$ substituent in the B group of Formula I, at each occurrence, is selected from the group consisting of hydrogen, halogen, $C_{1-4}$ alkyl and $C_{1-4}$ haloalkyl. In yet another embodiment, B group is selected from the optionally substituted group consisting of hydrogen, fluoro, chloro bromo, iodo, —$OCH_3$, —CN, —$OCH_2CH_2OH$, —$OCH_2CH_2NH_2$, —$CH_2CO_2H$, —$OCH_2CO_2H$, —$CO_2H$, —$OCH_2CH_2CO_2H$. In a certain aspect of these embodiments, m is 0 or 1; $R^{2a}$ is preferably hydrogen; and additionally in another aspect, $R^{2c}$ is preferably selected from the group consisting of F, Cl, Br, CN, $NO_2$, —$CO_2CH_3$, —$C(O)CH_3$ and —$S(O)_2CH_3$.

In yet another embodiment, the $R^3$ substituent of the B group in Formula I is a member independently selected from the group consisting of hydrogen, halogen, —$OR^f$, —$NR^fR^g$, —$C(O)R^f$, —$C(O)OR^f$, —$S(O)R^f$, —$S(O)_2R^f$, —$S(O)_3R^f$, —$S(O)_3R^h$, —$X^3C(O)_2R^f$, $X^3S(O)_3R^f$, —$S(O)_2NR^fR^g$, —$X^3S(O)_2NR^fR^g$, —$R^h$, —CN, $X^3NR^fR^g$, $NR^fC(O)R^f$, —$X^3OR^f$, —$X^3CONR^fR^g$, $X^3N_3$ and Y, wherein Y is a five to six-membered aryl, a five or six-membered heteroaryl ring or a three to eight-membered heterocycloalkyl ring selected from the group consisting of homopiperidinyl, morpholinyl, thiomorpholinyl, pyrrolidinyl, piperidinyl, azetidinyl, pyranyl, tetrahydrofuranyl, piperazinzyl, phenyl, pyridyl, oxazolyl, pyrimidinyl, oxadiazolyl, imidazolyl, pyrazolyl, triazolyl, pyrrolyl and thiazolyl, optionally substituted with from one to three substitutents selected from the group consisting of halogen, —$OR^f$, —$NR^fR^g$, —$R^h$, —CN, wherein each $R^f$ and $R^g$ is independently selected from hydrogen, $C_{1-6}$ alkyl, $C_{1-6}$ haloalkyl and $C_{3-6}$ cycloalkyl, and each $R^h$ is independently selected from the group consisting of $C_{1-6}$ alkyl, $C_{1-6}$ haloalkyl and $C_{3-6}$ cycloalkyl.

Within each of the above embodiments, the aliphatic portions of the $R^3$ substitutents is optionally further substituted with from one to three members selected from the group consisting of —OH, —$OR^o$, —$OC(O)NHR^o$, —$OC(O)N(R^o)_2$, —SH, —$SR^o$, —$S(O)R^o$, —$S(O)_2R^o$, —$SO_2NH_2$, —$S(O)_2NHR^o$, —$S(O)_2N(R^o)_2$, —$NHS(O)_2R^o$, —$NR^oS(O)_2R^o$, —$C(O)NH_2$, —$C(O)NHR^o$, —$C(O)N(R^o)_2$, —$C(O)R^o$, —$NHC(O)R^o$, —$NR^oC(O)R^o$, —$NHC(O)NH_2$, —$NR^oC(O)NH_2$, —$NR^oC(O)NHR^o$, —$NHC(O)NHR^o$, —$NR^oC(O)N(R^o)_2$, —$NHC(O)N(R^o)_2$, —$CO_2H$, —$CO_2R^o$, —$NHCO_2R^o$, —$NR^oCO_2R^o$, —CN, —$NO_2$, —$NH_2$, —$NHR^o$, —$N(R^o)_2$, —$NR^oS(O)NH_2$ and —$NR^oS(O)_2NHR^o$, wherein each $R^o$ is independently an unsubstituted $C_{1-6}$ alkyl.

In some embodiments, in Formula I, B is a bicyclic ring system (-$B^1$-$B^2$), whereas in other embodiments, -$B^1$-$B^2$ is a fused bicyclic ring system. In yet other embodiments, -$B^1$ and $B^2$ are connected by a single bond. In other embodiments, in Formula I, B is a monocyclic ring system (-$B^1$). In some embodiments, $B^1$ is attached to the remainder of the molecule through a carbon atom. In other embodiments, $B^1$ is attached to the remainder of the molecule through a nitrogen atom.

In a first embodiment of the B group in Formula I, B is a bicyclic ring (-$B^1$-$B^2$) having a formula selected from the group consisting of:

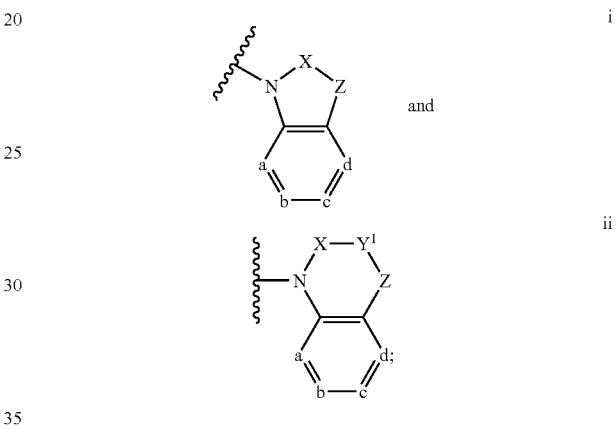

in which X, $Y^1$ and Z are each independently selected from the group consisting of —$CH_2$—, —$CHR^3$—, —$C(R^3)_2$—, —$NR^3$—, —NH—, —S—, —O—, —C(O)—, —S(O)— and —$S(O)_2$—. Optionally, any two substituents on the adjacent atoms of X and $Y^1$, or $Y^1$ and Z may be absent and replaced with a bond to form a double bond between X and $Y^1$, or $Y^1$ and Z. In one embodiment, the $R^3$ substituent on the $B^1$ ring in Formula i and ii is selected from the group consisting of halogen, —$OR^f$, —$NR^fR^g$, —$C(O)R^f$, —$C(O)OR^f$, —$S(O)R^f$, —$S(O)_2R^f$, —$S(O)_3R^f$, —$S(O)_3R^h$, —$X^3C(O)_2R^f$, $X^3S(O)_3R^f$, —$S(O)_2NR^fR^g$, —$X^3S(O)_2NR^fR^g$, —$R^h$, —CN, $X^3NR^fR^g$, $NR^fC(O)R^f$, —$X^3OR^f$, —$X^3CONR^fR^g$, $X^3N_3$, wherein each $R^f$ and $R^g$ is independently selected from hydrogen, $C_{1-6}$ alkyl, $C_{1-6}$ haloalkyl and $C_{3-6}$ cycloalkyl, and each $R^h$ is independently selected from the group consisting of $C_{1-6}$ alkyl, $C_{1-6}$ haloalkyl and $C_{3-6}$ cycloalkyl. The aliphatic portions of $X^3$, $R^f$, $R^g$ and $R^h$ is optionally further substituted with from one to three members selected from the group consisting of —OH, —$OR^o$, —$OC(O)NHR^o$, —$OC(O)N(R^o)_2$, —SH, —$SR^o$, —$S(O)R^o$, —$S(O)_2R^o$, —$SO_2NH_2$, —$S(O)_2NHR^o$, —$S(O)_2N(R^o)_2$, —$NHS(O)_2R^o$, —$NR^oS(O)_2R^o$, —$C(O)NH_2$, —$C(O)NHR^o$, —$C(O)N(R^o)_2$, —$C(O)R^o$, —$NHC(O)R^o$, —$NR^oC(O)R^o$, —$NHC(O)NH_2$, —$NR^oC(O)NH_2$, —$NR^oC(O)NHR^o$, —$NHC(O)NHR^o$, —$NR^oC(O)N(R^o)_2$, —$NHC(O)N(R^o)_2$, —$CO_2H$, —$CO_2R^o$, —$NHCO_2R^o$, —$NR^oCO_2R^o$, —CN, —$NO_2$, —$NH_2$, —$NHR^o$, —$N(R^o)_2$, —$NR^oS(O)NH_2$ and —$NR^oS(O)_2NHR^o$, wherein each $R^o$ is independently an unsubstituted $C_{1-6}$ alkyl.

Each of ring vertices a, b, c and d of the $B^2$ ring in Formula i and ii is independently selected from the group consisting of N, N⁺—O⁻, C(H) and C(R³); and from 0-2 ring vertices is N or N⁺—O⁻. In certain embodiments, 1 or 2 of said ring vertices a, b, c and d in Formula i and ii are N or N—O. In one embodiment, the ring vertex a is N or N⁺—O⁻ and ring vertices b, c and d are each independently C(H) or C(R³). In another embodiment, the ring vertex d is N or N⁺—O⁻ and ring vertices a, b and c are each independently C(H) or C(R³). In yet another embodiment, the ring vertex b is N or N⁺—O⁻ and ring vertices a, c and d are each independently C(H) or C(R³). In yet another embodiment, the ring vertex c is N or N⁺—O⁻ and ring vertices a, b and d are each independently C(H) or C(R³). In yet another embodiment, the ring vertices a, b, c and d are each independently C(H) or C(R³). Within the above embodiments of Formula i and ii, when any of the ring vertices a, b, c or d of the B² ring is C(R³), the R³ substituent, in certain embodiments, is independently selected from the group consisting of hydrogen, halogen, —OR$^f$, NR$^f$R$^g$, SR$^f$, —R$^h$, —Y, —CN, X³N₃, —SO₂R$^h$, X³NR$^f$R$^g$, X³Y, —S(O)₃R$^f$, —C(C=NOR)NR$^f$R$^g$, —NO₂, —CO₂R$^f$ and —NR$^g$C(O)R$^f$, wherein Y is an optionally substituted group selected from the group consisting of phenyl, pyridyl, pyrimidinyl, oxazolyl, thiazolyl, oxadiazolyl, imidazolyl, pyrazolyl, triazolyl, pyrrolyl and morpholinyl, and R$^h$ is an optionally substituted group selected from the group consisting of $C_{1-8}$ alkyl, $C_{1-8}$ haloalkyl and $C_{3-8}$ cycloalkyl, and R$^f$ and R$^g$ are each independently an optionally substituted group selected from the group consisting of hydrogen, $C_{1-8}$ alkyl, $C_{1-8}$ haloalkyl and $C_{3-8}$ cycloalkyl wherein the aliphatic portions the R³ substituent are each independently optionally substituted with from one to three members selected from the group consisting of —OH, —OR°, —OC(O)NHR°, —OC(O)N(R°)₂, —SH, —SR°, —S(O)R°, —S(O)₂R°, —SO₂NH₂, —S(O)₂NHR°, —S(O)₂N(R°)₂, —NHS(O)₂R°, —NR°S(O)₂R°, —C(O)NH₂, —C(O)NHR°, —C(O)N(R°)₂, —C(O)R°, —NHC(O)R°, —NR°C(O)R°, —NHC(O)NH₂, —NR°C(O)NH₂, —NR°C(O)NHR°, —NHC(O)NHR°, —NR°C(O)N(R°)₂, —NHC(O)N(R°)₂, —CO₂H, —CO₂R°, —NHCO₂R°, —NR°CO₂R°, —CN, —NO₂, —NH₂, —NHR°, —N(R°)₂, —NR°S(O)NH₂ and —NR°S(O)₂NHR°, wherein each R° is independently an unsubstituted $C_{1-6}$ alkyl.

In one preferred embodiment, R³ substituent on the B² ring of the B group, at each occurrence, is independently selected from the optionally substituted group consisting of halogen, —OR$^f$, —NR$^f$R$^g$, —SR$^f$, —R$^h$, —CN, —NO₂, —C(NR$^f$R$^g$)=NOR$^f$, —CO₂R$^f$ and —Y, wherein Y is an optionally substituted group selected from the group consisting of phenyl, pyridyl, oxazolyl, pyrimidinyl, oxadiazolyl, imidazolyl, pyrazolyl, triazolyl, pyrrolyl, and thiazoyl. In a certain aspect of this embodiment, the R³ substituent is independently selected from the group consisting of fluoro, chloro, bromo, iodo, amino, —CH₃, oxazolyl, 2-oxazolyl, thiazolyl, pyridyl, pyrimidinyl, morpholinyl, oxdiazolyl, 2-oxadiazolyl, —OH, —OCH₃, —OCH₂CO₂H, —OCH₂CO₂Et, —OCH₂CH₂OH, —OCH₂CH₂NH₂, —NHC(O)CH₃, —CN, —CH₂N₃, —CH₂SO₃H, —NO₂, —(C=NOH)NH₂, —S(O)₂CH₃ and —CH₂NH₂.

In yet another embodiment, in Formula i and ii the ring vertices a, b, c and d of the B ring are C(H) or C(R³), wherein R³ is halogen. In yet another embodiment, the ring vertices a, b, d of the B ring are each C(H) and c is C(R³), wherein R³ is fluoro, chloro, bromo or iodo. In yet another embodiment, the ring vertices a, c, d are each C(H) and b is C(R³), wherein R³ is fluoro, chloro, bromo or iodo.

In one embodiment, -B¹-B² is a bicyclic ring having Formula i and is selected from the group consisting of

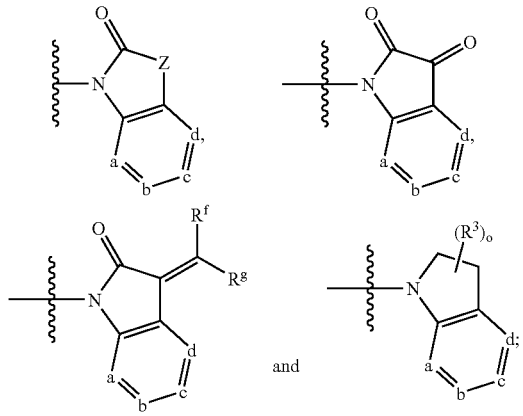

and wherein the subscript o is from 0-3, and wherein certain preferred substituents R$^f$, R$^g$, R³, Z and the ring vertices a, b, c and d are as described above for Formula i.

In one preferred embodiment, the bicyclic ring -B¹-B² of Formula I has the Formula i$^{a1}$

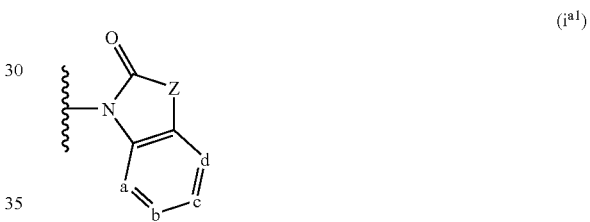

(i$^{a1}$)

in which Z is CH₂, CHR³, C(R³)₂, NH, NR³ or O, wherein certain preferred embodiments of the R³ substituent (on the B¹ ring) and the ring vertices a, b, c and d of the B² ring are set forth as described for Formula i. Furthermore, in another embodiment, the R³ substitutent, at each occurrence, on the B¹ ring is selected from the group consisting of —R$^h$, —X₃OR$^f$, —X₃NR$^f$R$^g$, —X₃CO₂R$^f$ and —X₃CONR$^f$R$^g$. In another embodiment, the R³ substitutent, at each occurrence on the B¹ ring is selected from the group consisting of methyl, ethyl, propyl, CH₂CH₂OH, CH₂CH₂NH₂, CH₂CH₂NMeH, CH₂CO₂H and CH₂CONH₂.

Each of ring vertices a, b, c and d in the B² ring of Formula i$^{a1}$ is independently selected from the group consisting of N, N⁺—O⁻, C(H) and C(R³); and from 0-2 ring vertices is N or N⁺—O⁻. When any of the ring vertices a, b, c or d of the B² ring is C(R³), in one embodiment, the R³ substituent is independently selected from the group consisting of hydrogen, halogen, —OR$^f$, NR$^f$R$^g$, SR$^f$, —R$^h$, —Y, —CN, X³N₃, —SO₂R$^h$, X³NR$^f$R$^g$, X³Y, —S(O)₃R$^f$, —C(C=NOR)NR$^f$R$^g$, —NO₂, —CO₂R$^f$ and —NR$^g$C(O)R$^f$, wherein Y is an optionally substituted group selected from the group consisting of phenyl, pyridyl, pyrimidinyl, oxazolyl, thiazolyl, oxadiazolyl, imidazolyl, pyrazolyl, triazolyl, pyrrolyl and morpholinyl, and R$^h$ is an optionally substituted group selected from the group consisting of $C_{1-8}$ alkyl, $C_{1-8}$ haloalkyl and $C_{3-8}$ cycloalkyl, wherein the aliphatic portions of R³ is each independently optionally substituted with from one to three members selected from the group consisting of —OH, —OR°, —OC(O)NHR°, —OC(O)N(R°)$_2$, —SH, —SR°, —S(O)R°, —S(O)$_2$R°, —SO$_2$NH$_2$, —S(O)$_2$NHR°, —S(O)$_2$N(R°)$_2$, —NHS(O)$_2$R°, —NR°S(O)$_2$R°, —C(O)NH$_2$, —C(O)NHR°, —C(O)N(R°)$_2$, —C(O)R°, —NHC(O)R°, —NR°C(O)R°, —NHC(O)NH$_2$, —NR°C(O)NH$_2$, —NR°C(O)NHR°, —NHC(O)NHR°, —NR°C(O)N(R°)$_2$, —NHC(O)N(R°)$_2$, —CO$_2$H, —CO$_2$R°, —NHCO$_2$R°, —NR°CO$_2$R°, —CN, —NO$_2$, —NH$_2$, —NHR°, —N(R°)$_2$, —NR°S(O)NH$_2$ and —NR°S(O)$_2$NHR°, wherein each R° is independently an unsubstituted C$_{1-6}$ alkyl.

In one embodiment, the ring vertices a, b, c and d in the B$^2$ ring of Formulae i$^{a1}$ are each independently C(H) or C(R$^3$). In another embodiment, in Formula i$^{a1}$, the ring vertices a, b, d of the B$^2$ ring are each C(H) and c is C(R$^3$). In another embodiment, the ring vertices a, c, d of the B$^2$ ring are each C(H) and b is C(R$^3$). In another embodiment, the ring vertex a of the B$^2$ ring is N or N$^+$—O$^-$ and the ring vertices b, c, d are each C(H) or C(R$^3$). Within each of the above embodiments, R$^3$ is selected from the group consisting of halogen, —OR$^f$, —CN, —NO$_2$, C(NH$_2$)=NOR$^f$ and —Y, wherein Y is an optionally substituted oxadiazolyl, oxazolyl, pyrrolyl, pyrazolyl, imidazolyl or thiazolyl group. In a specific aspect of this embodiment, R$^3$ on the B$^2$ ring is selected from the group consisting of fluoro, chloro, bromo, iodo, OMe, CN, —C(NH$_2$)=NOH, oxadiazolyl or OR$^f$, wherein R$^f$ is selected from the group consisting of hydrogen, C$_{1-4}$ alkyl optionally substituted with —CO$_2$H, —CO$_2$R°, —NH$_2$, —NR°H and —N(R°)$_2$. In yet another embodiment, the R$^3$ substituent of the B$^2$ ring is selected from the group consisting of halogen, —OR$^f$, —CN, —NO$_2$, C(NH$_2$)=NOR$^f$ and —Y, wherein Y is an optionally substituted oxadiazolyl, oxazolyl, pyrrolyl, pyrazolyl, imidazolyl or thiazolyl group. In certain aspects of this embodiment, R$^3$ on the B$^2$ ring is selected from the group consisting of OMe, CN, —C(NH$_2$)=NOH, oxadiazolyl or OR$^f$, wherein R$^f$ is selected from the group consisting of hydrogen, C$_{1-4}$ alkyl optionally substituted with —CO$_2$H, —CO$_2$R°, —NH$_2$, —NR° H and —N(R°)$_2$.

In another aspect of this embodiment, in Formula i$^{a1}$, -B$^1$-B$^2$ is selected from the group consisting of:

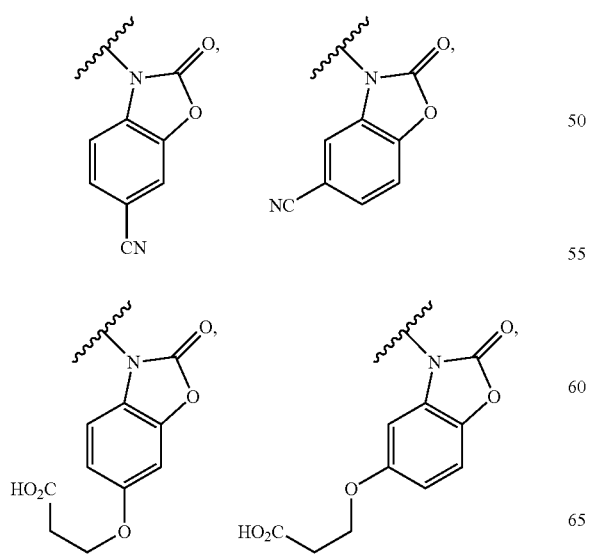

-continued

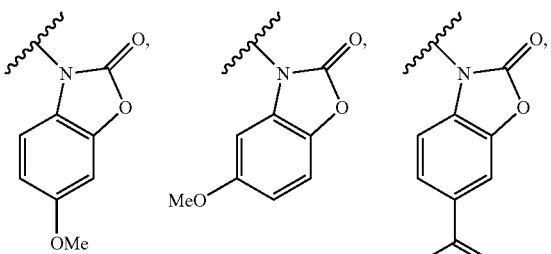

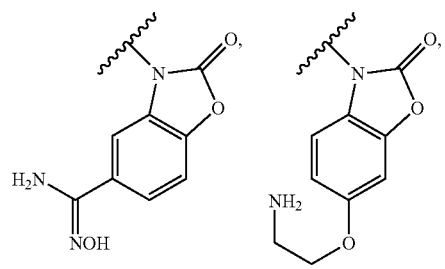

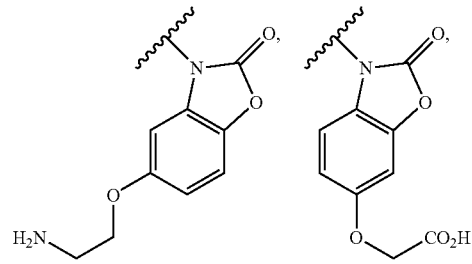

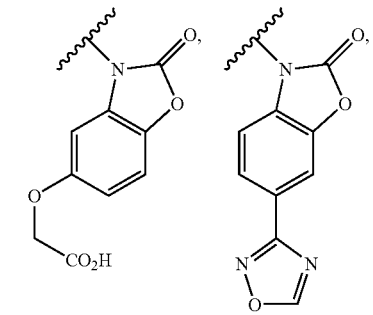

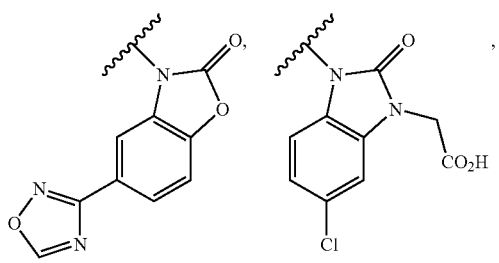

-continued
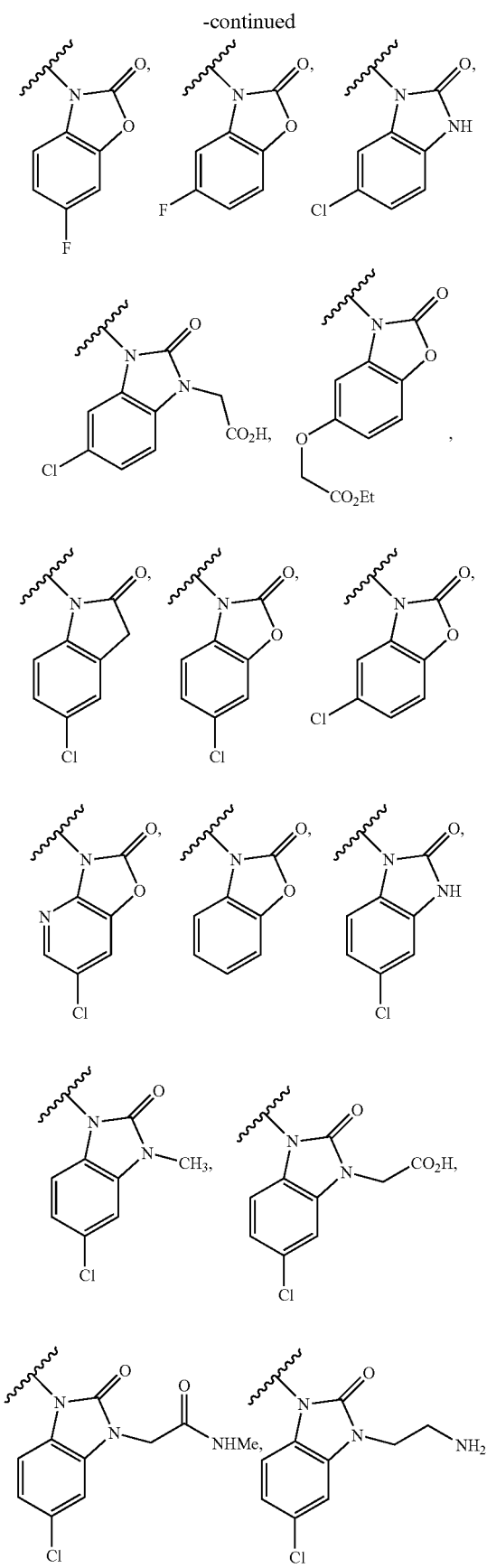
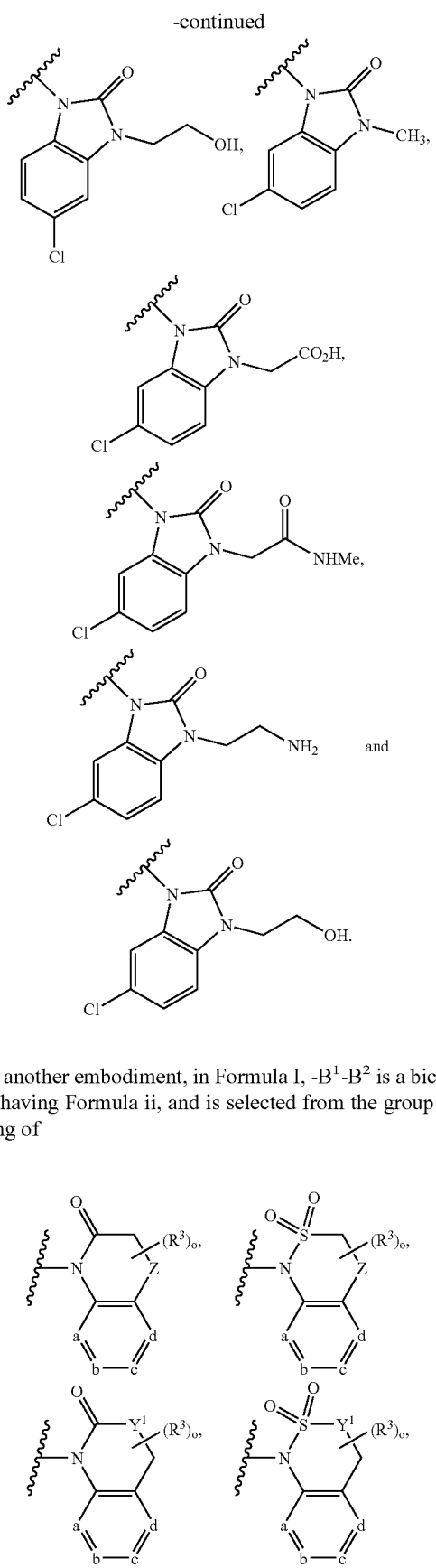
In another embodiment, in Formula I, -B¹-B² is a bicyclic ring having Formula ii, and is selected from the group consisting of
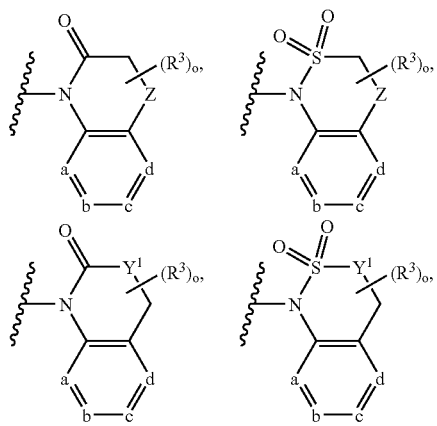

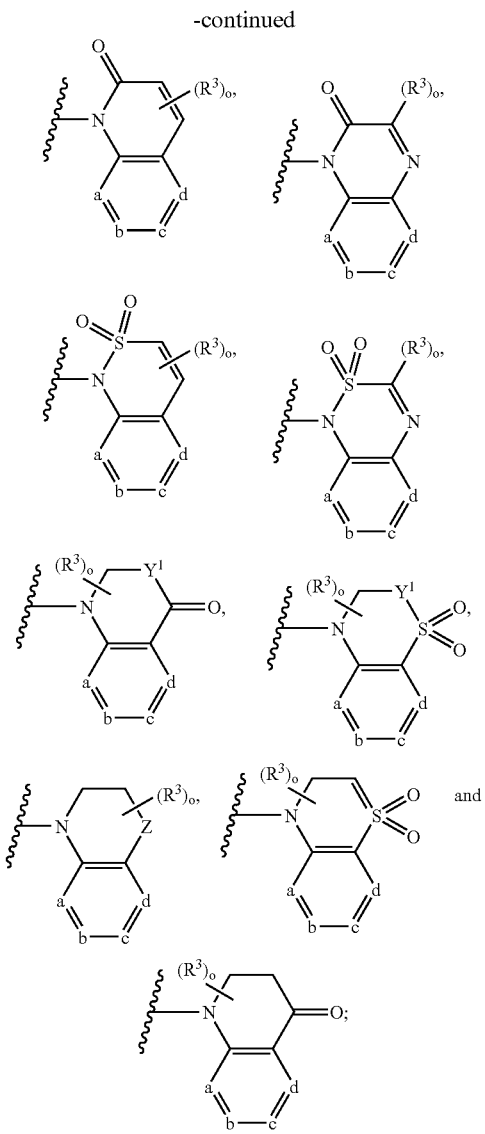

wherein Y¹ and Z are —NH—, N(R³), —CH₂—, —CHR³—, —C(R³)₂, —O or S; and the subscript o is 0-2. In yet another embodiment, -B¹-B² is a bicyclic ring having Formula ii, in which X is —C(O)—; Y¹ is —CH₂—, —CHR³— or —C(R³)₂; and Z is —NH—, —NR³—, O or S. In each of these embodiments, the substituents, R³ and the ring vertices a, b, c and d are as set forth for Formula ii.

In a preferred embodiment, -B¹-B² is a bicyclic ring having the Formula ii and is selected from the group consisting of:

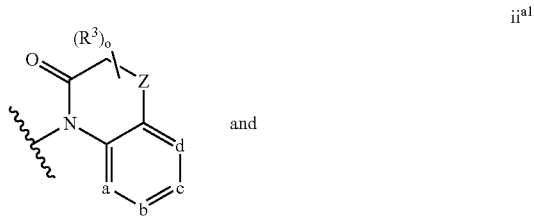

ii^{a1} and

ii^{a2} wherein the symbols Y¹ and Z are independently selected from the group consisting of O, NH and NR³, wherein the substituent R³, if present, is halogen or R^h. The subscript o in Formula ii^{a1} and ii^{a2} is an integer from 0-1.

Each of ring vertices a, b, c and d of the B² ring in Formula ii^{a1} or ii^{a2} is independently selected from the group consisting of N, N⁺—O⁻, C(H) and C(R³); and from 0-2 ring vertices is N or N⁺—O⁻. When any of the ring vertices a, b, c or d of the B² ring in Formula ii^{a1} or ii^{a2} is C(R³), the R³ substituent is independently selected from the group consisting of hydrogen, halogen, —OR^f, NR^fR^g, SR^f, —R^h, —Y, —CN, X³N₃, —SO₂R^h, X³NR^fR^g, X³Y, —S(O)₃R^f, —C(C=NOR^f)NR^fR^g, —NO₂, —CO₂R^f and —NR^gC(O)R^f, wherein Y is an optionally substituted group selected from the group consisting of phenyl, pyridyl, pyrimidinyl, oxazolyl, thiazolyl, oxadiazolyl, imidazolyl, pyrazolyl, triazolyl, pyrrolyl and morpholinyl, and R^h is an optionally substituted group selected from the group consisting of C₁₋₈ alkyl, C₁₋₈ haloalkyl and C₃₋₈ cycloalkyl, wherein the aliphatic portions of R³ is each independently optionally substituted with from one to three members selected from the group consisting of —OH, —OR°, —OC(O)NHR°, —OC(O)N(R°)₂, —SH, —SR°, —S(O)R°, —S(O)₂R°, —SO₂NH₂, —S(O)₂NHR°, —S(O)₂N(R°)₂, —NHS(O)₂R°, —NR°S(O)₂R°, —C(O)NH₂, —C(O)NHR°, —C(O)N(R°)₂, —C(O)R°, —NHC(O)R°, —NR°C(O)R°, —NHC(O)NH₂, —NR°C(O)NH₂, —NR°C(O)NHR°, —NHC(O)NHR°, —NR°C(O)N(R°)₂, —NHC(O)N(R°)₂, —CO₂H, —CO₂R°, —NHCO₂R°, —NR°CO₂R°, —CN, —NO₂, —NH₂, —NHR°, —N(R°)₂, —NR°S(O)NH₂ and —NR°S(O)₂NHR°, wherein each R° is independently an unsubstituted C₁₋₆ alkyl.

In one embodiment, the ring vertices a, b, c and d in Formulae ii^{a1} and ii^{a2} are independently C(H) or C(R³). In another embodiment, the ring vertices a, b, d in Formulae ii^{a1} and ii^{a2} are each C(H) and c is C(R³). In another embodiment, the ring vertices a, c, d are each C(H) and b is C(R³). In another embodiment, the ring vertex a is N or N⁺—O⁻, and the ring vertices b, c and d are each independently C(H) or C(R³). In another embodiment, the ring vertex c is N or N⁺—O⁻, and the ring vertices a, b and d are each independently C(H) or C(R³). In preferred aspects of the above embodiments, R³ is selected from the group consisting of halogen, —OR^f, —CN, —NO₂, C(NH₂)=NOR^f and —Y, wherein Y is an optionally substituted oxadiazolyl, oxazolyl, pyrrolyl, pyrazolyl, imidazolyl or thiazolyl group. In one embodiment, the R³ on the B² ring is selected from the group consisting of fluoro, chloro, bromo, iodo, OMe, CN, —C(NH₂)=NOH, oxadiazolyl or OR^f, wherein R^f is selected from the group consisting of hydrogen, C₁₋₄ alkyl optionally substituted with —CO₂H, —CO₂R°, —NH₂, —NR°H and —N(R°)₂. In another embodiment, R³ of the B² ring is halogen or OR^f, preferably methoxy, fluoro, chloro, bromo or iodo.

In one embodiment, in Formula ii^{a1} and ii^{a2}, -B¹-B² is selected from the group consisting of

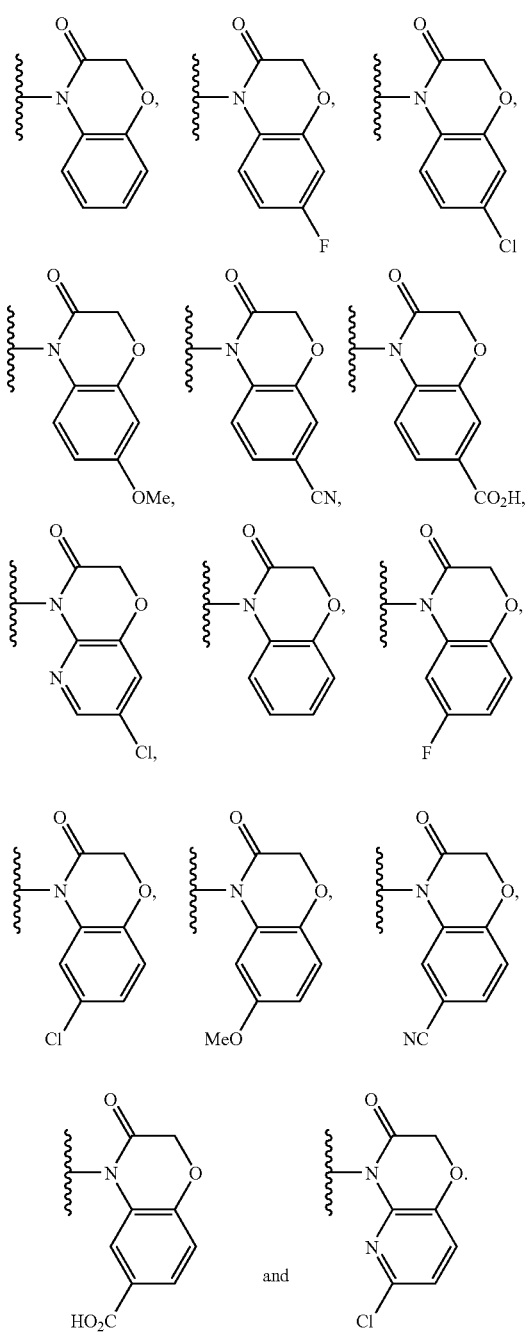

In another embodiment, in Formula ii$^{a1}$ and ii$^{a2}$, -B$^1$-B$^2$ is selected from the group consisting of

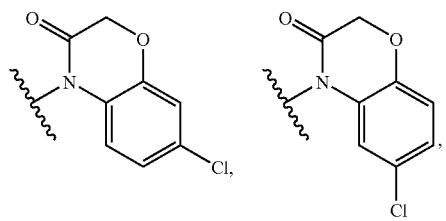

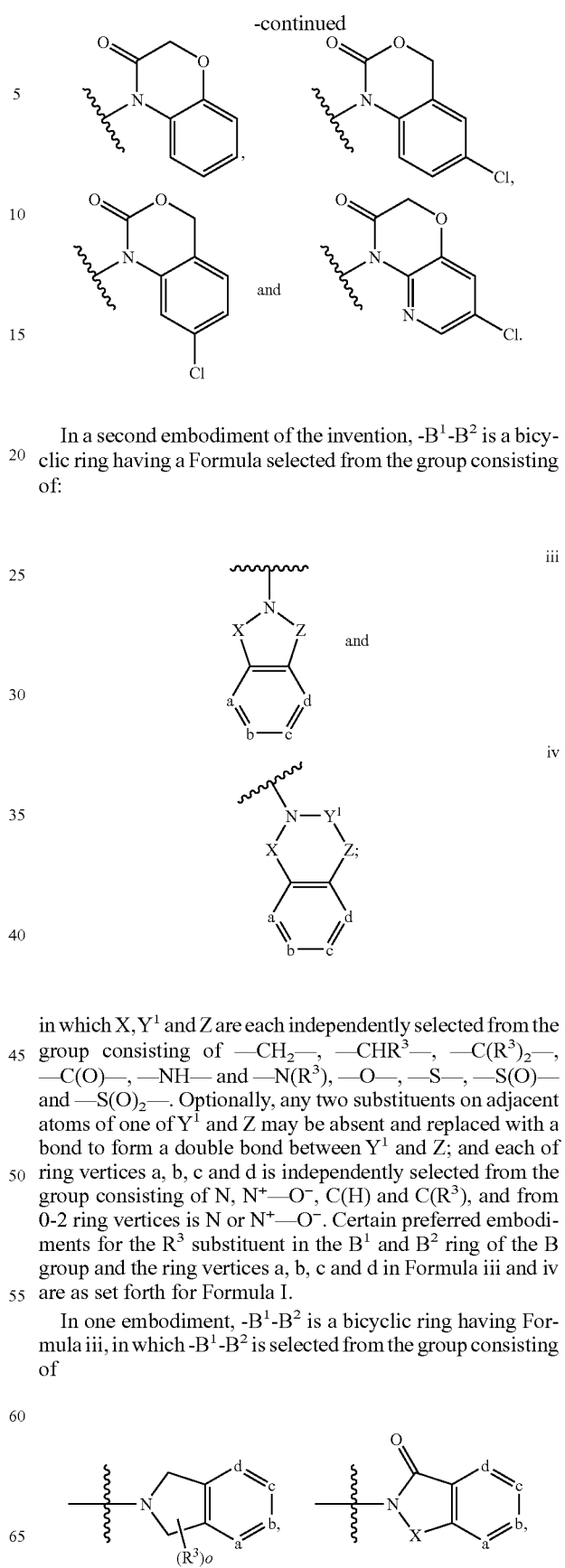

In a second embodiment of the invention, -B$^1$-B$^2$ is a bicyclic ring having a Formula selected from the group consisting of:

in which X, Y$^1$ and Z are each independently selected from the group consisting of —CH$_2$—, —CHR$^3$—, —C(R$^3$)$_2$—, —C(O)—, —NH— and —N(R$^3$), —O—, —S—, —S(O)— and —S(O)$_2$—. Optionally, any two substituents on adjacent atoms of one of Y$^1$ and Z may be absent and replaced with a bond to form a double bond between Y$^1$ and Z; and each of ring vertices a, b, c and d is independently selected from the group consisting of N, N$^+$—O$^-$, C(H) and C(R$^3$), and from 0-2 ring vertices is N or N$^+$—O$^-$. Certain preferred embodiments for the R$^3$ substituent in the B$^1$ and B$^2$ ring of the B group and the ring vertices a, b, c and d in Formula iii and iv are as set forth for Formula I.

In one embodiment, -B$^1$-B$^2$ is a bicyclic ring having Formula iii, in which -B$^1$-B$^2$ is selected from the group consisting of

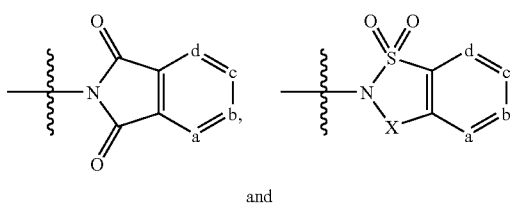

and

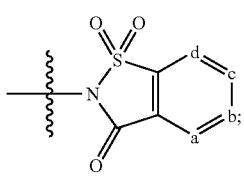

wherein X is CH$_2$, CHR$^3$, C(R$^3$)$_2$, —NH—, N(R$^3$), O or S; and the subscript o is 0-2.

In another embodiment, -B$^1$-B$^2$ is a bicyclic ring having Formula iv, in which -B$^1$-B$^2$ is selected from the group consisting of

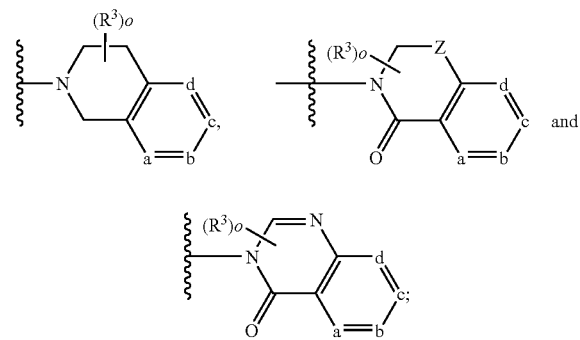

in which the subscript o is 0-2.

In a third embodiment of the invention, B$^1$-B$^2$ is a bicyclic ring having a formula selected from the group consisting of:

v

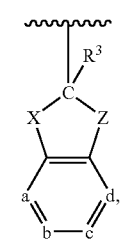

vi

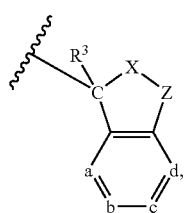

vii

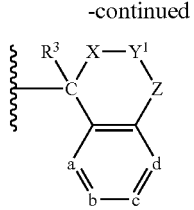

and viii

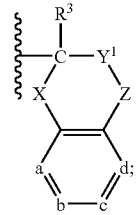

in which X, Y$^1$ and Z are each independently selected from the group consisting of —CH$_2$—, —CHR$^3$—, —C(R$^3$)$_2$, —C(O)—, —S(O)—, —S(O)$_2$—, —NH—, —N(R$^3$), —S— and —O—, wherein at least one of X, Y$^1$ and Z is —NH— or —N(R$^3$)—. Optionally, any two substituents on adjacent atoms of X and C, C and Y$^1$, X and Y$^1$, X and Z, or Y$^1$ and Z may be absent and replaced with a bond to form a double bond between X and C, C and Y, X and Y$^1$, X and Z, or Y$^1$ and Z. Each of ring vertices a, b, c and d is independently selected from the group consisting of N, N$^+$—O$^-$, —CH— and C(R$^3$), and from 0-2 ring vertices is N or N$^+$—O$^-$. In Formulae v, vi, vii and viii, the preferred embodiments of R$^3$ substituent in the B$^1$ and B$^2$ ring of the B group and the ring vertices a, b, c and d are as set forth for Formula I.

In a fourth embodiment, -B$^1$-B$^2$ is a bicyclic ring having the formula:

ix

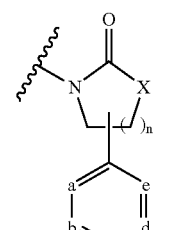

and x

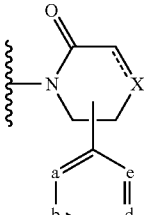

wherein X is selected from the group consisting of C, N, O and S; the subscript n is an integer from 1-2; the bond ----- represents a single or double bond. In Formula ix and x, the R$^3$ substituent of the -B$^1$ ring is each independently selected from the group halogen, —OR$^f$, —OC(O)R$^f$, —NR$^f$R$^g$, —SR$^f$, —R$^h$, —CN, —NO$_2$, —CO$_2$R$^f$, —CONR$^f$R$^g$, —C(O)R$^f$, —OC(O)NR$^f$R$^g$, —NR$^g$C(O)R$^f$, —NR$^g$C(O)$_2$R$^h$, —NR$^f$—C(O)NR$^f$R$^g$, —NH—C(NH$_2$)=NH, —NR$^h$C(NH$_2$)=NH, —NH—C(NH$_2$)=NR$^h$, NH—C(NHR$^h$)=NH, —S(O)R$^h$, —S(O)$_2$R$^h$, —NR$^f$S(O)$_2$R$^h$, —S(O)$_2$NR$^f$R$^g$, —NR$^f$S(O)$_2$R$^h$, —NR$^f$S(O)$_2$NR$^f$R$^g$, —N$_3$, —X$^3$OR$^f$, —X$^3$OC(O)R$^f$, —X$^3$NR$^f$R$^g$, —X$^3$SR$^f$, —X$^3$CN, —X$^3$NO$_2$, —X$^3$CO$_2$R$^f$, —X$^3$CONR$^f$R$^g$, —X$^3$C(O)R$^f$, —X$^3$OC(O)NR$^f$R$^g$, —X$^3$NR$^g$C(O)R$^f$, —X$^3$NR$^g$C(O)$_2$R$^h$, —X$^3$NR$^f$—C(O) NR$^f$R$^g$, —X$^3$NH—C(NH$_2$)=NH, —X$^3$NR$^h$C(NH$_2$)=NH, —X$^3$NH—C(NH$_2$)=NR$^h$, —X$^3$NH—C(NHR$^h$)=NH, —X$^3$S(O)R$^h$, —X$^3$S(O)$_2$R$^h$, —X$^3$NR$^f$S(O)$_2$R$^h$, —X$^3$S(O)$_2$NR$^f$R$^g$, and —X$^3$N$_3$, and wherein any two R$^3$ substitutents on attached to the same atom may be replaced with the substitutents =O, =NH, =NOH, =NR$^f$, =S or =CR$^f$R$^g$; and optionally any two R$^3$ substituents on -B$^1$ located on adjacent atoms are absent and replaced with a bond to form a double bond. The subscript o is 0-2; and each of ring vertices a, b, c d and e is independently selected from the group consisting of N, —C(H)— and C(R$^3$), and from 0-2 ring vertices is N or N$^+$—O$^-$, wherein the R$^3$ substituent on the B$^2$ ring as set forth for Formula I.

In another embodiment, in Formula I, B is the monocyclic ring system (-B$^1$). In yet another embodiment, -B$^1$ is a optionally substituted monocyclic ring system wherein the heterocyclic ring is selected from the group consisting of oxazolidinonyl, imidazolidinonyl, thiazolidinonyl, oxazinanonyl, thiazinanonyl, azetidinyl, pyrrolidinyl, piperidinyl, imidazolidinyl, pyrazolidinyl, morpholinyl, thiomorpholinyl, thiomorpholinyl-S-oxide, thiomorpholinyl-S,S-dioxide, piperazinzyl, butyrolactamyl, valerolactamyl, caprolactamyl, hydantoinyl, dihydropyridinyl and pyridonyl. In yet another embodiment, in Formula I, B is the monocyclic ring system B$^1$ and is attached to the remainder of the molecule through a nitrogen atom. In yet another embodiment, in Formula I, B is the monocyclic ring system B$^1$ and is attached to the remainder of the molecule through a carbon atom. In another embodiment, in Formula I, B is the monocyclic ring system is selected from the group consisting of oxazolidinonyl, imidazolidinonyl, thiazolidinonyl, oxazinanonyl, thiazinanonyl, morpholinyl, thiomorpholinyl, valerolactamyl, caprolactamyl, piperidinyl, piperazinyl and pyrrolidinyl and is optionally substituted with 1 to 2 R$^3$ substituents selected from R$^h$, —OR$^f$, OC(O)R$^f$, —OC(O)NR$^f$R$^g$, NR$^g$C(O)R$^f$, —CN and —CO$_2$R$^f$. In another embodiment, in Formula I, B is the monocyclic ring system selected from the group consisting of oxazolidinonyl, imidazolidinonyl, oxazinanonyl, morpholinyl, piperidinyl, piperazinyl and is optionally substituted with 1 to 2 R$^3$ substituents selected from R$^h$, —OR$^f$, OC(O)R$^f$, —OC(O)NR$^f$R$^g$, —C(O)NR$^f$R$^g$, NR$^g$C(O)R$^f$, —CN and —CO$_2$R$^f$. In certain aspects of these embodiments, R$^3$ is selected from —OMe, —NH$_2$, —CN, —CH$_3$, —CH$_2$CH$_3$, —CO$_2$H, —CO$_2$Me and —C(O)NMe$_2$.

In Formula I, the symbol L$^1$ is a linking group selected from the group consisting of C$_{1-3}$ alkylene, C$_{1-3}$ heteroalkylene, optionally substituted with phenyl, —R$^k$, —X$^4$OR$^i$, —X$^4$OC(O)R$^i$, —X$^4$NR$^i$R$^j$, —X$^4$SR$^i$, —X$^4$CN or —X$^4$NO$_2$. X$^4$ is selected from the group consisting of C$_{1-4}$ alkylene, C$_{2-4}$ alkenylene and C$_{2-4}$ alkynylene. Each R$^i$ and R$^j$ is independently selected from hydrogen, C$_{1-8}$ alkyl, C$_{1-8}$ haloalkyl, C$_{3-6}$ cycloalkyl, C$_{2-8}$ alkenyl, C$_{2-8}$ alkynyl, aryl, heteroaryl, aryl-C$_{1-4}$ alkyl, and aryloxy-C$_{1-4}$ alkyl. Each R$^k$ is independently selected from the group consisting of C$_{1-8}$ alkyl, C$_{1-8}$ haloalkyl, C$_{3-6}$ cycloalkyl, C$_{2-8}$ alkenyl, C$_{2-8}$ alkynyl, aryl, heteroaryl, aryl-C$_{1-4}$ alkyl, and aryloxy-C$_{1-4}$ alkyl. In one embodiment, L$^1$ is selected from the group consisting of —CH$_2$—, —CH$_2$CH$_2$—, —CH$_2$CH$_2$CH$_2$—, —CH$_2$O—, —CH$_2$NH—, —CH$_2$OCH$_2$—, and —CH$_2$NHCH$_2$—. In a preferred embodiment, L$^1$ is —CH$_2$—.

In Formula I, the symbol U is selected from the group consisting of N, C—R$^p$ and N$^+$—O$^-$, wherein R$^p$ is selected from the group consisting of hydrogen, C$_{1-3}$ alkylene-OR$^q$, C$_{1-3}$ alkylene-N(R$^q$)$_2$, C$_{1-3}$ alkylene-NH(R$^q$), —OH, —OR$^q$, —R$^q$, —CN, —OC(O)NHR$^q$, OC(O)N(R$^q$)$_2$, —SH, —SR$^q$, —S(O)R$^q$, —S(O)$_2$R$^q$, —SO$_2$NH$_2$, —S(O)$_2$NHR$^q$, —S(O)$_2$N(R$^q$)$_2$, —NHS(O)$_2$R$^q$, —NR$^q$S(O)$_2$R$^q$, —C(O)NH$_2$, —C(O)NHR$^q$, —C(O)N(R$^q$)$_2$, —C(O)R$^q$, —NHC(O)R$^q$, —NR$^q$C(O)R$^q$, —NHC(O)NH$_2$, NR$^q$C(O)NH$_2$, NR$^q$C(O)NHR$^q$, —NHC(O)NHR$^q$, —NR$^q$C(O)N(R$^q$)$_2$, —NHC(O)N(R$^q$)$_2$, —CO$_2$H, —CO$_2$R$^q$, —NHCO$_2$R$^q$, —NR$^q$CO$_2$R$^q$, —NH$_2$, —NHR$^q$, —N(R$^q$)$_2$, —NR$^q$S(O)NH$_2$, —NHC(=NH)NH$_2$, —NHC(=NH)R$^q$ and —NR$^q$S(O)$_2$NHR$^q$. R$^q$ is each independently C$_{1-8}$ alkyl, C$_{1-8}$ haloalkyl, C$_{3-8}$ cycloalkyl; and the aliphatic portions of R$^q$ is optionally further substituted with from one to three members selected from the group consisting of —OH, —OR$^r$, —OC(O)NHR$^r$, —OC(O)N(R$^r$)$_2$, —SH, —SR$^r$, —S(O)R$^r$, —S(O)$_2$R$^r$, —SO$^2$NH$^2$, —S(O)$_2$NHR$^r$, —S(O)$_2$N(R$^r$)$_2$, —NHS(O)$_2$R$^r$, —NR$^r$S(O)$_2$R$^r$, —C(O)NH$_2$, —C(O)NHR$^r$, —C(O)N(R$^r$)$_2$, —C(O)R$^r$, —NHC(O)R$^r$, —NR$^q$C(O)R$^r$, —NHC(O)NH$_2$, —NR$^r$C(O)NH$_2$, —NR$^r$C(O)NHR$^r$, —NHC(O)NHR$^r$, —NR$^r$C(O)N(R$^r$)$_2$, —NHC(O)N(R$^r$)$_2$, —CO$_2$H, —CO$_2$R$^f$, —NHCO$_2$R$^r$, —NR$^r$CO$_2$R$^r$, —CN, —NO$_2$, —NH$_2$, —NHR$^r$, —N(R$^r$)$_2$, —NR$^r$S(O)NH$_2$ and —NR$^r$S(O)$_2$NHR$^r$, wherein each R$^r$ is independently an unsubstituted C$_{1-6}$ alkyl. In one embodiment, U is selected from the group consisting of N, C—R$^p$ and N—O, wherein R$^p$ is —OH, —NH$_2$, —CH$_2$OH, —CH$_2$NH$_2$, —CN, —OR$^q$, —R$^q$, —C(O)$_2$R$^q$ and —C(O)R$^q$. In a preferred embodiment, U is selected from the group consisting of N, C—R$^p$ and N—O, wherein R$^p$ is —OH, —CN, —OR$^q$, R$^q$, or —C(O)R$^q$. In another embodiment the symbol U is selected from the group consisting of N, C—R$^p$ and N$^+$—O$^-$, wherein R$^p$ is hydrogen, —OH, —CH$_2$OH, —CH$_2$OR$^q$, —NH$_2$, —CH$_2$NH$_2$, —CH$_2$NHR$^q$, —OR$^q$, —R$^q$, —CN, —NO$_2$, CO$_2$H, and —CO$_2$R$^q$. In another embodiment, U is selected from the group consisting of N, C—R$^p$ and N—O, in which R$^p$ is hydrogen, —OH, C$_{1-3}$ alkylene-OR$^q$, —NH$_2$, —NHC(O)R$^q$, NHR$^q$, —NHCONH$_2$, —NHC(=NH)NH$_2$, —NHC(=NH)R$^q$, C$_{1-3}$ alkylene-NH(R$^q$), —OR$^q$, —R$^q$, —CN, —NO$_2$, —CO$_2$H, or —CO$_2$R$^q$. In another embodiment, U is selected from the group consisting of N, C—R$^p$ and N—O, in which R$^p$ is hydrogen, —OH, —CH$_2$OH, —CH$_2$OR$^q$—NH$_2$, —NHC(O)CH$_3$, NHC(O)CH$_2$NH$_2$, —NHC(O)CH$_2$OH, —NHCH$_2$CH$_2$NH, —NHCH$_2$CH$_2$OH, —NHCONH$_2$, —NHC(=NH)NH$_2$, —NHC(=NH)CH$_3$, —OR$^q$, —R$^q$, —CN, —NO$_2$, —CO$_2$H, or —CO$_2$CH$_3$. In a preferred embodiment, U is nitrogen. In another preferred embodiment, U is C—R$^p$.

In Formula I, the symbol L$^2$ is a linking group selected from the group consisting of a direct bond, C$_{1-3}$ alkylene, C$_{1-8}$ heteroalkyl, —O—, —NR$^s$, —C(O)—, —C(R$^s$)$_2$, —S(O)—, —S(O)$_2$—, —NR$^s$C(O)— and —NR$^s$S(O)$_2$—. The substituent R$^s$ is, at each occurrence, independently selected from the group consisting of hydrogen, C$_{1-8}$ alkyl, C$_{1-8}$ haloalkyl, C$_{3-6}$ cycloalkyl, C$_{2-8}$ alkenyl, C$_{2-8}$ alkynyl, C$_{6-10}$ aryl and C$_{5-10}$ heteroaryl; wherein the aliphatic portion of R$^s$ are optionally further substituted with from one to three members selected from the group consisting of —OH, —OR$^t$, —OC(O)NHR$^t$, —OC(O)N(R$^t$)$_2$, —SH, —SR$^t$, —S(O)R$^t$, —S(O)$_2$R$^t$, —SO$_2$NH$_2$, —S(O)$_2$NHR$^t$, —S(O)$_2$N(R$^t$)$_2$, —NHS(O)$_2$R$^t$, —NR$^t$S(O)$_2$R$^t$, —C(O)NH$_2$, —C(O)NHR$^t$, —C(O)N(R$^t$)$_2$, —C(O)R$^t$, —NHC(O)R$^t$, —NR$^o$C(O)R$^t$, —NHC(O)NH$_2$, —NR$^o$C(O)NH$_2$, —NR$^t$C(O)NHR$^t$, —NHC(O)NHR$^t$, —NR'C(O)N(R')$_2$, —NHC(O)N(R')$_2$, —CO$_2$H, —CO$_2$R',
—NHCO$_2$R', —NR'CO$_2$R', —CN, —NO$_2$, —NH$_2$,
—NHR', —N(R')$_2$, —NR'S(O)NH$_2$ and —NR'S(O)$_2$NHR',
wherein each R' is independently an unsubstituted C$_{1-6}$ alkyl or C$_{1-6}$ haloalkyl The subscript n is an integer from 0-2. In one embodiment, L$^2$ is selected from the group consisting of direct bond, —CH$_2$—, —O—, —C(R')$_2$, —S(O)—, —S(O)$_2$—, —C(O)— and —NR'— wherein R' is a C$_{1-6}$ alkyl or C$_{1-6}$ haloalkyl. In another embodiment, L$^2$ is selected from the group consisting of direct bond, —CH$_2$— and —O—. In another embodiment, L$^2$ is a direct bond or —CH$_2$—.

B. Other Embodiments

In yet another embodiment of the invention, the compound having Formula I has the subformulae Ia, Ib or Ic:

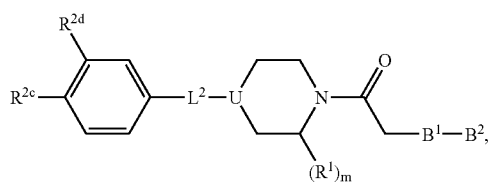

Ia

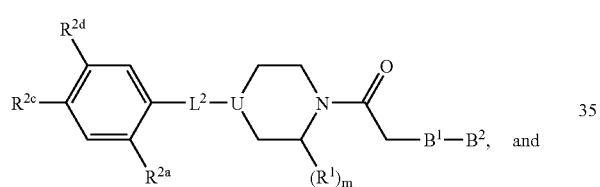

Ib

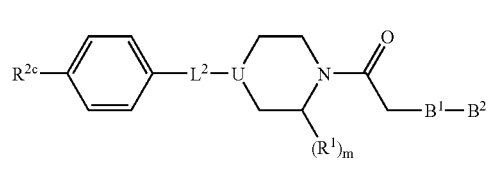

Ic in which R$^{2c}$ is halogen, —CN, or —NO$_2$; R$^{2d}$ is —SR$^e$, —O—X$^2$—OR$^c$, —X$^2$—OR$^c$, —R$^e$, —OR$^c$, —NR$^c$R$^d$, —NR$^c$S(O)$_2$R$^e$ or —NR$^d$C(O)R$^c$; and R$^{2a}$ is halogen, —CO$_2$R$^c$, —C(O)NR$^c$R$^d$, —CN, oxazolyl, —X$^2$NR$^c$R$^d$ or —C(NOR$^c$)R$^d$. The subscript m is 0-1; and wherein R$^1$, when present, is —CO$_2$H or C$_{1-4}$ alkyl, optionally substituted with —OH, —OR$^m$, —S(O)$_2$R$^m$, —CO$_2$H and —CO$_2$R$^m$. In a preferred embodiment, in the compounds having Formulae Ia, Ib and Ic, R$^{2c}$ is —F, —Cl, —Br, —I, cyano, or nitro; R$^{2d}$ is —SCH$_3$, —CH$_3$, —CH$_2$CH$_3$, —CH$_2$OCH$_3$, —OCH$_3$, —OCH$_2$CH$_3$ or —N(CH$_3$)$_2$; and R$^{2a}$ is F, Cl, Br, I, —CO$_2$Me, —CONH$_2$, —CN, oxazolyl, —CH$_2$NH$_2$, —CH$_2$NHMe, —CH$_2$NMe$_2$ or —CH(=N—OH). The subscript m is 0-1 and wherein R$^1$ when present is —CO$_2$H or C$_{1-4}$ alkyl.

In yet another embodiment of the invention, the compound having Formula I has the subformulae selected from the group consisting of:

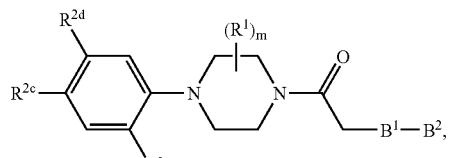

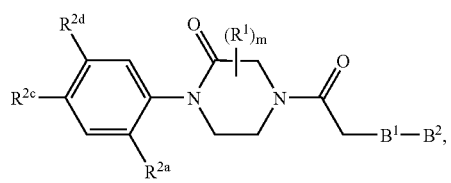

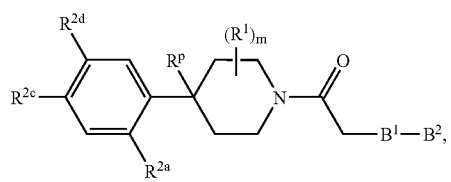

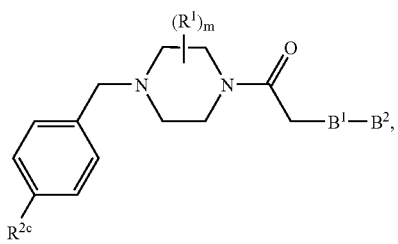

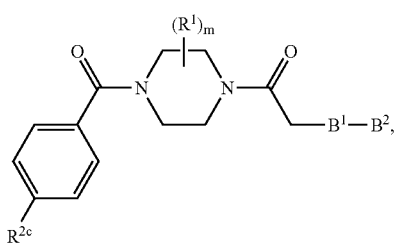

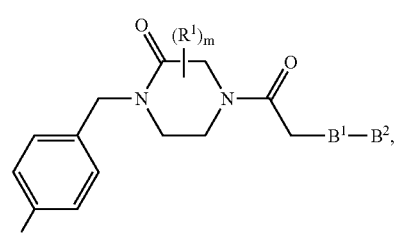

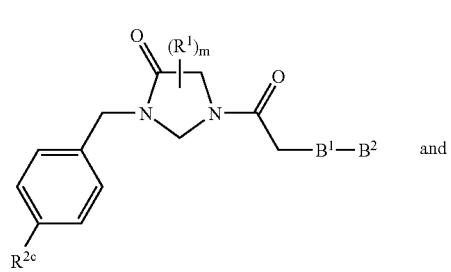

and

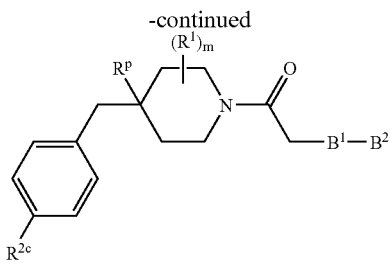

wherein $R^{2c}$ is halogen, —CN, or —$NO_2$; $R^{2d}$ is —$SR^c$, —O—$X^2$—$OR^c$, —$X^2$—$O^{Rc}$, —$R^e$, —$OR^c$, —$NR^cR^d$, —$NR^cS(O)_2R^e$ or —$NR^dC(O)R^c$; and $R^{2a}$ is halogen, —$CO_2R^c$, —$C(O)NR^cR^d$, —CN, oxazolyl, —$X^2NR^cR^d$ or —$C(NOR^c)R^d$; the subscript m is 0-1; wherein $R^1$, when present, is —$CO_2H$ or $C_{1-4}$ alkyl, optionally substituted with —OH, —$OR^m$, —$S(O)_2R^m$, —$CO_2H$ and —$CO_2R^m$; and wherein; $R^p$ is —OH, $C_{1-3}$ alkylene-$OR^q$, —$NH_2$, —NHC(O) $R^q$, $NHR^q$, —$NHCONH_2$, —NHC(=NH)$NH_2$, —NHC(=NH)$R^q$, $C_{1-3}$ alkylene-$NH(R^q)$, —$OR^q$, —$R^q$, —CN, —$NO_2$, —$CO_2H$, or —$CO_2R^q$.

In another embodiment, the compound of Formula I has the Formula Id:

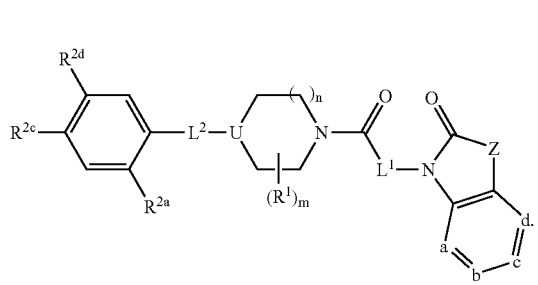

Id

In Formula Id, the subscript m is an integer from 0-2, preferably from 0-1; and the subscript n is an integer from 0-2, preferably from 0-1. The substituent $R^1$ is selected from the group consisting of —$CO_2R^a$ or $C_{1-4}$ alkyl, optionally substituted with OH, —$OR^m$, —$S(O)_2R^m$, —$CO_2H$ or —$CO_2R^m$, or optionally any two $R^1$ substituents located on the same atom is replaced with the substituent =O, or =S. In another embodiment, $R^1$, when present, is selected from the group consisting of —$CO_2H$ or $C_{1-4}$ alkyl, optionally substituted with OH, —$OR^m$, —$S(O)_2R^m$, —$CO_2H$ or —$CO_2R^m$, wherein $R^m$ is a $C_{1-4}$ alkyl. In one embodiment, $R^1$ is selected from —$CO_2H$, —$CO_2Me$, and methyl; and the subscript m is 0-1.

In Formula Id, the substituent $R^{2a}$ is selected from the group consisting of hydrogen, halogen, —$CO_2R^c$, —$C(O)NR^cR^d$, —CN, $R^e$, oxazolyl, —$X^2NR^cR^d$ and —$C(NOR^c)R^d$; $R^{2c}$ is selected from the group consisting of halogen, —CN, —$NO_2$, —$CO_2R^c$, —$C(O)NR^cR^d$, —$C(O)R^c$ and —$S(O)_2R^e$; and $R^{2d}$ is selected from the group consisting of hydrogen, —$SR^c$, —O—$X^2$—$OR^c$, —$X^2$—$OR^c$, —$R^e$, —$OR^c$, —$NR^cR^d$, —$NR^cS(O)_2R^e$ and —$NR^dC(O)R^c$. In a specific embodiment, $R^{2a}$ is F, Cl, Br, I, —$CO_2Me$, —$CONH_2$, —CN, —$CH_3$, oxazolyl, —$CH_2NH_2$, —$CH_2NHMe$, —$CH_2NMe_2$ or —CH(=N—OH); $R^{2c}$ is —F, —Cl, —Br, —I, cyano, or nitro; and $R^{2d}$ is —$SCH_3$, —$CH_3$, —$CH_2CH_3$, —$CH_2OCH_3$, —$OCH_3$, —$OCH_2CH_3$ or —$N(CH_3)_2$. In another specific embodiment, $R^{2a}$ is hydrogen; and $R^{2c}$ is —F, —Cl, —Br, —I, cyano, or nitro; and $R^{2d}$ is —$SCH_3$, —$CH_3$, —$CH_2CH_3$, —$CH_2OCH_3$, —$OCH_3$, —$OCH_2CH_3$ or —$N(CH_3)_2$. In another specific embodiment, $R^{2a}$ and $R^{2d}$ are each hydrogen and $R^{2c}$ $R^{2c}$ is —F, —Cl, —Br, —I, cyano, or nitro.

The symbol $L^1$, in Formula Id, is a $C_{1-3}$ alkylene or $C_{1-3}$ heteroalkylene. In one embodiment, the symbol $L^1$ is selected from the group consisting of —$CH_2$—, —$CH_2CH_2$—, —$CH_2CH_2CH_2$—, —$CH_2O$—, —$CH_2NH$—, —$CH_2OCH_2$—, and —$CH_2NHCH_2$—. In other embodiments, the symbol $L^1$ is —$CH_2$—. The symbol $L^2$ is selected from the group consisting of direct bond, —$CH_2$— and —O—; in certain embodiments, the symbol $L^2$ is a direct bond or —$CH_2$—.

In Formula Id, the symbol U is selected from the group consisting of N and C—$R^p$, wherein $R^p$ is —OH, $C_{1-3}$ alkylene-$OR^q$, —$NH_2$, —NHC(O)$R^q$, $NHR^q$, —$NHCONH_2$, —NHC(=NH)$NH_2$, —NHC(=NH)$R^q$, $C_{1-3}$ alkylene-NH($R^q$), —$OR^q$, —$R^q$, —CN, —$NO_2$, —$CO_2H$, or —$CO_2R^q$. In one embodiment, U is selected from the group consisting of N and C—$R^p$, wherein $R^p$ is hydrogen, —OH, —$CH_2OH$, —$CH_2OR^q$, —$NH_2$, —$CH_2NH_2$, —$CH_2NHR^q$, —$OR^q$, —$R^q$, —CN, —$NO_2$, $CO_2H$, or —$CO_2R^q$. In one embodiment, the symbol U is N. In another embodiment, the symbol U is C—$R^p$, wherein $R^p$ is selected from the group consisting of hydrogen, —OH, —$R^q$, —CN, —$CO_2H$ and —$CO_2R^q$. In another embodiment, the symbol U is nitrogen or C—$R^p$, wherein $R^p$ is selected from hydrogen and OH.

The symbol Z, in Formula Id, is $CH_2$, $CHR^3$, $C(R^3)_2$, NH, $NR^3$ or O, wherein $R^3$ (in the $B^1$ ring) is selected from the group consisting of —$R^h$, —$X^3OR^f$, —$X^3NR^fR^g$, —$X^3CO_2R^f$ and —$X^3CONR^fR^g$. In one embodiment, the $R^3$ substituent of the -$B^1$ ring is selected from the group consisting of methyl, ethyl, propyl, $CH_2CH_2OH$, $CH_2CH_2NH_2$, $CH_2CH_2NMeH$, $CH_2CO_2H$ and $CH_2CONH_2$.

Each of ring vertices a, b, c and d in Formula Id is independently selected from the group consisting of N, $N^+$—$O^-$, C(H) and C($R^3$); and from 0-2 ring vertices is N or $N^+$—$O^-$. If any of the ring vertices a, b, c or d in the $B^2$ ring is C($R^3$), in one embodiment, the $R^3$ substituent is independently selected from the group consisting of hydrogen, halogen, —$OR^f$, $NR^fR^g$, $SR^f$, —$R^h$, —Y, —CN, $X^3N_3$, —$SO_2R^h$, $X^3NR^fR^g$, $X^3Y$, —$S(O)_3R^f$, —$C(C=NOR^f)NR^fR^g$, —$NO_2$, and —$NR^gC(O)R^f$, wherein Y is an optionally substituted group selected from the group consisting of phenyl, pyridyl, pyrimidinyl, oxazolyl, thiazolyl, oxadiazolyl, imidazolyl, pyrazolyl, triazolyl, pyrrolyl and morpholinyl, and $R^h$ is an optionally substituted group selected from the group consisting of $C_{1-8}$ alkyl, $C_{1-8}$ haloalkyl and $C_{3-8}$ cycloalkyl, and $R^f$ and $R^g$ are each independently an optionally substituted group selected from the group consisting of hydrogen, $C_{1-8}$ alkyl, $C_{1-8}$ haloalkyl and $C_{3-8}$ cycloalkyl.

In another embodiment, $R^3$ is preferably selected from the group consisting of halogen, —$OR^f$, —CN, —$NO_2$, C($NH_2$)=$NOR^f$ and —Y, wherein Y is an optionally substituted oxadiazolyl, oxazolyl, pyrrolyl, pyrazolyl, imidazolyl and thiazolyl group. In a specific embodiment, $R^3$ on the $B^2$ ring is selected from the group consisting of OMe, CN, —C($NH_2$)=NOH, oxadiazolyl or $OR^f$, wherein $R^f$ is selected from the group consisting of hydrogen, $C_{1-4}$ alkyl optionally substituted with —$CO_2H$, —$CO_2R^o$, —$NH_2$, —$NR^oH$ and —$N(R^o)_2$.

Within each of the above embodiments, the aliphatic portions of the $R^3$ group of the $B^2$ ring are each independently optionally substituted with from one to three members selected from the group consisting of —OH, —$OR^o$, —OC(O)$NHR^o$, —OC(O)N($R^o)_2$, —SH, —$SR^o$, —$S(O)R^o$, —S(O)$_2$R$^o$, —SO$_2$NH$_2$, —S(O)$_2$NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$, wherein each R$^o$ is independently an unsubstituted C$_{1-6}$ alkyl.

In one embodiment, in Formula Id, the ring vertices a, b, c and d of the B$^2$ ring are C(H) or C(R$^3$). In one embodiment, in Formula Id the ring vertices a, b, d are each C(H) and c is C(R$^3$). In another embodiment, in Formula Id, the ring vertices a, c, d in Formula Id are each C(H) and b is C(R$^3$). In yet another aspect, in compounds having Formula Id, the ring vertex a is N or N$^+$—O$^-$ and the ring vertices b, c and d are each C(H) or C(R$^3$). In yet another aspect, in compounds having Formula Id, the ring vertex c is N or N$^+$—O$^-$ and the ring vertices a, b and d are each C(H) or C(R$^3$).

In yet another embodiment, the compounds of Formula I has the formula selected from the group consisting of

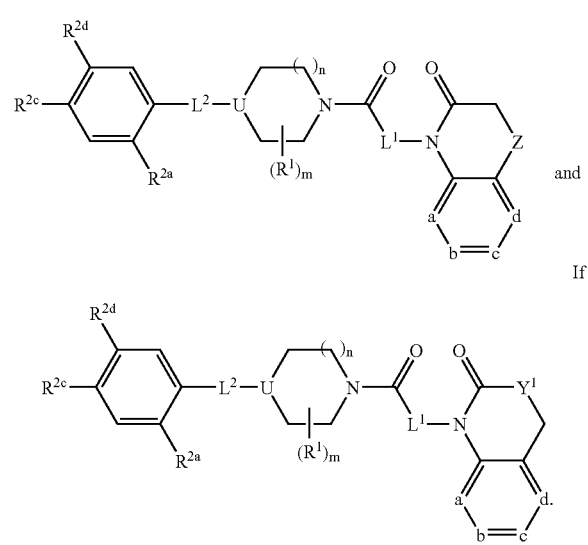

Ie and

If

In Formula Ie or If, the subscript m is an integer from 0-2, preferably from 0-1; and the subscript n is an integer from 0-2, preferably from 0-1. The substituent R$^1$ is selected from the group consisting of —CO$_2$R$^a$ or C$_{1-4}$ alkyl, optionally substituted with OH, —OR$^m$, —S(O)$_2$R$^m$, —CO$_2$H or —CO$_2$R$^m$, or optionally any two R$^1$ substituents located on the same atom is replaced with the substituent =O, or =S. In another embodiment, R$^1$, when present, is selected from the group consisting of —CO$_2$H or C$_{1-4}$ alkyl, optionally substituted with OH, —OR$^m$, —S(O)$_2$R$^m$, —CO$_2$H or —CO$_2$R$^m$, wherein R$^m$ is a C$_{1-4}$ alkyl. In one embodiment, R$^1$ is selected from —CO$_2$H, —CO$_2$Me, and methyl; and the subscript m is 0-1.

In Formula Ie or If, the substituent R$^{2a}$ is selected from the group consisting of hydrogen, halogen, —CO$_2$R$^c$, —C(O) NR$^c$R$^d$, —CN, R$^e$, oxazolyl, —X$^2$NR$^c$R$^d$ and —C(NOR$^c$)R$^d$; R$^{2c}$ is selected from the group consisting of halogen, —CN, —NO$_2$, —CO$_2$R$^c$, —C(O)NR$^c$R$^d$, —C(O)R$^c$ and —S(O)$_2$R$^e$; and R$^{2d}$ is selected from the group consisting of hydrogen, —SR$^c$, —O—X$^2$—OR$^c$, —X$^2$—OR$^c$, —R$^e$, —OR$^c$, —NR$^c$R$^d$, —NR$^c$S(O)$_2$R$^e$ and —NR$^d$C(O)R$^c$. In a specific embodiment, R$^{2a}$ is F, Cl, Br, I, —CO$_2$Me, —CONH$_2$, —CN, —CH$_3$, oxazolyl, —CH$_2$NH$_2$, —CH$_2$NHMe, —CH$_2$NMe$_2$ or —CH(=N—OH); R$^{2c}$ is —F, —Cl, —Br, —I, cyano, or nitro; and R$^{2d}$ is —SCH$_3$, —CH$_3$, —CH$_2$CH$_3$, —CH$_2$OCH$_3$, —OCH$_3$, —OCH$_2$CH$_3$ or —N(CH$_3$)$_2$. In another specific embodiment, R$^{2a}$ is hydrogen; and R$^{2c}$ is —F, —Cl, —Br, —I, cyano, or nitro; and R$^{2d}$ is —SCH$_3$, —CH$_3$, —CH$_2$CH$_3$, —CH$_2$OCH$_3$, —OCH$_3$, —OCH$_2$CH$_3$ or —N(CH$_3$)$_2$. In another specific embodiment, R$^{2a}$ and R$^{2d}$ are each hydrogen and R$^{2c}$ is —F, —Cl, —Br, —I, cyano, or nitro.

The symbol L$^1$, in Formula Ie or If, is a C$_{1-3}$ alkylene or C$_{1-3}$ heteroalkylene. In one embodiment, the symbol L$^1$ is selected from the group consisting of —CH$_2$—, —CH$_2$CH$_2$—, —CH$_2$CH$_2$CH$_2$—, —CH$_2$O—, —CH$_2$NH—, —CH$_2$OCH$_2$—, and —CH$_2$NHCH$_2$—. In other embodiments, the symbol L$^1$ is —CH$_2$—. The symbol L$^2$ is selected from the group consisting of direct bond, —CH$_2$— and —O—; in certain embodiments, the symbol L$^2$ is a direct bond or —CH$_2$—.

In Formula Ie or If, the symbol U is selected from the group consisting of N and C—R$^p$, wherein R$^p$ is —OH, C$_{1-3}$ alkylene-OR$^q$, —NH$_2$, —NHC(O)R$^q$, NHR$^q$, —NHCONH$_2$, —NHC(=NH)NH$_2$, —NHC(=NH)R$^q$, C$_{1-3}$ alkylene-NH (R$^q$), —OR$^q$, —R$^q$, —CN, —NO$_2$, —CO$_2$H, or —CO$_2$R$^q$. In one embodiment, U is selected from the group consisting of N and C—R$^p$, wherein R$^p$ is hydrogen, —OH, —CH$_2$OH, —CH$_2$OR$^q$, —NH$_2$, —CH$_2$NH$_2$, —CH$_2$NHR$^q$, —OR$^q$, —R$^q$, —CN, —NO$_2$, CO$_2$H, or —CO$_2$R$^q$. In one embodiment, the symbol U is N. In another embodiment, the symbol U is C—R$^p$, wherein R$^p$ is selected from the group consisting of hydrogen, —OH, —R$^q$, —CN, —CO$_2$H and —CO$_2$R$^q$. In one embodiment, the symbol U is N or C—R$^p$, wherein R$^p$ is hydrogen or OH.

The symbols Z and Y$^1$, in Formula Ie or If, are each independently selected from CH$_2$, CHR$^3$, C(R$^3$)$_2$, NH, NR$^3$ or O, wherein R$^3$ (in the B$^1$ ring) is selected from the group consisting of —R$^h$, —X$^3$OR$^f$, —X$^3$NR$^f$R$^g$, —X$^3$CO$_2$R$^f$ and CONR$^f$R$^g$. In one embodiment, the R$^3$ substituent of the -B$^1$ ring is selected from the group consisting of methyl, ethyl, propyl, CH$_2$CH$_2$OH, CH$_2$CH$_2$NH$_2$, CH$_2$CH$_2$NMeH, CH$_2$CO$_2$H and CH$_2$CONH$_2$.

Each of ring vertices a, b, c and d in Formula Ie or If is independently selected from the group consisting of N, N$^+$—O$^-$, C(H) and C(R$^3$); and from 0-2 ring vertices is N or N$^+$—O$^-$. If any of the ring vertices a, b, c or d in the B$^2$ ring is C(R$^3$), in one embodiment, the R$^3$ substituent is independently selected from the group consisting of hydrogen, halogen, —OR$^f$, NR$^f$R$^g$, SR$^f$, —R$^h$, —Y, —CN, X$^3$N$_3$, —SO$_2$R$^h$, X$^3$NR$^f$R$^g$, X$^3$Y, —S(O)$_3$R$^f$, —C(C=NOR$^f$)NR$^f$R$^g$, —NO$_2$, and —NR$^g$C(O)R$^f$, wherein Y is an optionally substituted group selected from the group consisting of phenyl, pyridyl, pyrimidinyl, oxazolyl, thiazolyl, oxadiazolyl, imidazolyl, pyrazolyl, triazolyl, pyrrolyl and morpholinyl, and R$^h$ is an optionally substituted group selected from the group consisting of C$_{1-8}$ alkyl, C$_{1-8}$ haloalkyl and C$_{3-8}$ cycloalkyl, and R$^f$ and R$^g$ are each independently an optionally substituted group selected from the group consisting of hydrogen, C$_{1-8}$ alkyl, C$_{1-8}$ haloalkyl and C$_{3-8}$ cycloalkyl.

In another embodiment, R$^3$ is preferably selected from the group consisting of halogen, —OR$^f$, —CN, —NO$_2$, C(NH$_2$) =NOR$^f$ and —Y, wherein Y is an optionally substituted oxadiazolyl, oxazolyl, pyrrolyl, pyrazolyl, imidazolyl and thiazolyl group. In a specific embodiment, R$^3$ on the B$^2$ ring is selected from the group consisting of OMe, CN, —C(NH$_2$) =NOH, oxadiazolyl or OR$^f$, wherein R$^f$ is selected from the group consisting of hydrogen, C$_{1-4}$ alkyl optionally substituted with —CO₂H, —CO₂Rᵒ, —NH₂, —NRᵒH and —N(Rᵒ)₂. In certain embodiments, R³ in the B² ring is halogen or ORᶠ, wherein Rᶠ is selected from the group consisting of hydrogen, $C_{1-4}$ alkyl optionally substituted with —CO₂H, —CO₂Rᵒ, —NH₂, —NRᵒH and —N(Rᵒ)₂.

Within each of the above embodiments, the aliphatic portions of the R³ group of the B² ring are each independently optionally substituted with from one to three members selected from the group consisting of —OH, —ORᵒ, —OC(O)NHRᵒ, —OC(O)N(Rᵒ)₂, —SH, —SRᵒ, —S(O)Rᵒ, —S(O)₂Rᵒ, —SO₂NH₂, —S(O)₂NHRᵒ, —S(O)₂N(Rᵒ)₂, —NHS(O)₂Rᵒ, —NRᵒS(O)₂Rᵒ, —C(O)NH₂, —C(O)NHRᵒ, —C(O)N(Rᵒ)₂, —C(O)Rᵒ, —NHC(O)Rᵒ, —NRᵒC(O)Rᵒ, —NHC(O)NH₂, —NRᵒC(O)NH₂, —NRᵒC(O)NHRᵒ, —NHC(O)NHRᵒ, —NRᵒC(O)N(Rᵒ)₂, —NHC(O)N(Rᵒ)₂, —CO₂H, —CO₂Rᵒ, —NHCO₂Rᵒ, —NRᵒCO₂Rᵒ, —CN, —NO₂, —NH₂, —NHRᵒ, —N(Rᵒ)₂, —NRᵒS(O)NH₂ and —NRᵒS(O)₂NHRᵒ, wherein each Rᵒ is independently an unsubstituted $C_{1-6}$ alkyl.

In one embodiment, in Formula Ie or If, the ring vertices a, b, c and d of the B² ring are C(H) or C(R³). In one embodiment, in Formula Ie or If the ring vertices a, b, d are each C(H) and c is C(R³). In another embodiment, in Formula Id, the ring vertices a, c, d in Formula Ie or If are each C(H) and b is C(R³). In yet another aspect, in compounds having Formula Ie or If, the ring vertex a is N or N⁺—O⁻ and the ring vertices b, c and d are each C(H) or C(R³). In yet another aspect, in compounds having Formula Ie or If, the ring vertex d is N or N⁺—O⁻ and the ring vertices a, b and d are each C(H) or C(R³).

In another specific embodiment, in Formula I, the substituent R¹ is independently selected from the group consisting of $C_{1-8}$ alkyl, $C_{1-8}$ haloalkyl, $C_{3-6}$ cycloalkyl, —CO₂Rᵃ, —X¹CO₂Rᵃ, —X¹SO₂Rᵃ, —X¹SO₃Rᵃ, —X¹ORᵃ, —CORᵃ, CONRᵃRᵇ, —X¹NRᵃRᵇ, —X¹NRᵃCORᵇ, —X¹CONRᵃRᵇ, X¹NRᵃS(O)₂Rᵇ, —X¹S(O)₂NRᵃRᵇ and X¹S(O)₂Rᵃ, wherein X¹ is $C_{1-4}$ alkylene and each Rᵃ and Rᵇ is independently selected from the group consisting of hydrogen, $C_{1-8}$ alkyl, $C_{1-8}$ haloalkyl and $C_{3-6}$ cycloalkyl, optionally any two R¹ substituents attached to the same atom are optionally replaced with the substituent =O, =NH, =NOH, =NRᵃ, =S or =CRᵃRᵇ, and wherein the aliphatic portions of each of said R¹ substituents is optionally substituted with from one to three members selected from the group consisting of —OH, —ORᵐ, —OC(O)NHRᵐ, —OC(O)N(Rᵐ)₂, —SH, —SRᵐ, —S(O)Rᵐ, —S(O)₂Rᵐ, —SO₂NH₂, —S(O)₂NHRᵐ, —S(O)₂N(Rᵐ)₂, —NHS(O)₂Rᵐ, —NRᵐS(O)₂Rᵐ, —C(O)NH₂, —C(O)NHRᵐ, —C(O)N(Rᵐ)₂, —C(O)Rᵐ, —NHC(O)Rᵐ, —NRᵐC(O)Rᵐ, —NHC(O)NH₂, —NRᵐC(O)NH₂, —NRᵐC(O)NHRᵐ, —NHC(O)NHRᵐ, —NRᵐC(O)N(Rᵐ)₂, —NHC(O)N(Rᵐ)₂, —CO₂H, —CO₂Rᵐ, —NHCO₂Rᵐ, —NRᵐCO₂Rᵐ, —CN, —NO₂, —NH₂, —NHRᵐ, —N(Rᵐ)₂, —NRᵐS(O)NH₂ and —NRᵐS(O)₂NHRᵐ, wherein each Rᵐ is independently an unsubstituted $C_{1-6}$ alkyl. The subscript m is an integer from 0-2; and the subscript n is an integer from 0-1. The substituents $R^{2a}$, $R^{2c}$ and $R^{2d}$ are each independently selected from the group consisting of hydrogen, halogen, cyano, heteroaryl, —NO₂, —CO₂Rᶜ, —CONRᶜRᵈ, —C(O)Rᶜ, —S(O)Rᵉ, —S(O)₂Rᵉ, —Rᵉ, —C(NORᶜ)Rᵈ, —C(NRᶜV)=NV, —N(V)C(Rᶜ)=NV, —X²C(NORᶜ)Rᵈ, —X²C(NRᶜV)=NV, —X²N(V)C(Rᶜ)=NV, —X²NRᶜRᵈ, —X²SRᶜ, —X²NO₂, —X²CO₂Rᶜ, —X²CONRᶜRᵈ, —X²C(O)Rᶜ, —X²OC(O)NRᶜRᵈ, —X²NRᶜC(O)Rᶜ, —X²NRᵈC(O)₂Rᵉ, —X²NRᶜC(O)NRᶜRᵈ, —X²NH—C(NH₂)=NH, —X²NRᵉC(NH₂)=NH, —X²NH—C(NH₂)=NRᵉ, —X²NH—C(NHRᵉ)=NH, —X²S(O)Rᵉ, —X²S(O)₂Rᵉ, —X²NRᶜS(O)₂Rᵉ, —X²S(O)₂NRᶜRᵈ, —X²N₃, ORᶜ, —SRᶜ, —Rᵉ, —NRᵈC(O)Rᶜ, NRᵈC(O)₂Rᵉ, —S(O)₂Rᵉ, —S(O)₂NRᶜRᵈ, —X²ORᶜ, —O—X²ORᶜ, —X²NRᶜRᵈ, —O—X²NRᶜRᵈ and NRᵈ—X²CO₂Rᶜ; wherein within each of $R^{2a}$, $R^{2c}$ and $R^{2d}$, X² is $C_{1-4}$ alkylene and each Rᶜ and Rᵈ is independently selected from hydrogen, $C_{1-8}$ alkyl, $C_{1-8}$ haloalkyl, $C_{3-6}$ cycloalkyl, or optionally, Rᶜ and Rᵈ when attached to the same nitrogen atom can be combined with the nitrogen atom to form a five or six-membered ring having from 0 to 2 additional heteroatoms as ring members; and each Rᵉ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl and heteroaryl, and each of Rᶜ, Rᵈ and Rᵉ is optionally further substituted with from one to three members selected from the group consisting of —OH, —ORⁿ, —OC(O)NHRⁿ, —OC(O)N(Rⁿ)₂, —SH, —SRⁿ, —S(O)Rⁿ, —S(O)₂Rⁿ, —SO₂NH₂, —S(O)₂NHRⁿ, —S(O)₂N(Rⁿ)₂, —NHS(O)₂Rⁿ, —NRⁿS(O)₂Rⁿ, —C(O)NH₂, —C(O)NHRⁿ, —C(O)N(Rⁿ)₂, —C(O)Rⁿ, —NHC(O)Rⁿ, —NRⁿC(O)Rⁿ, —NHC(O)NH₂, —NRⁿC(O)NH₂, —NRⁿC(O)NHRⁿ, —NHC(O)NHRⁿ, —NRⁿC(O)N(Rⁿ)₂, —NHC(O)N(Rⁿ)₂, —CO₂H, —CO₂Rⁿ, —NHCO₂Rⁿ, —NRⁿCO₂Rⁿ, —CN, —NO₂, —NH₂, —NHRⁿ, —N(Rⁿ)₂, —NRⁿS(O)NH₂ and —NRⁿS(O)₂NHRⁿ, wherein each Rⁿ is independently an unsubstituted $C_{1-6}$ alkyl; and wherein V is independently selected from the group consisting of —Rᶜ, —CN, —CO₂Rᵉ and —NO₂. The symbol B represents a monocyclic (-B¹) ring system, or a bicyclic (-B¹-B²) ring system selected from the group consisting of formulae i, ii, iii, iv, v, vi, vii, viii, ix and x:

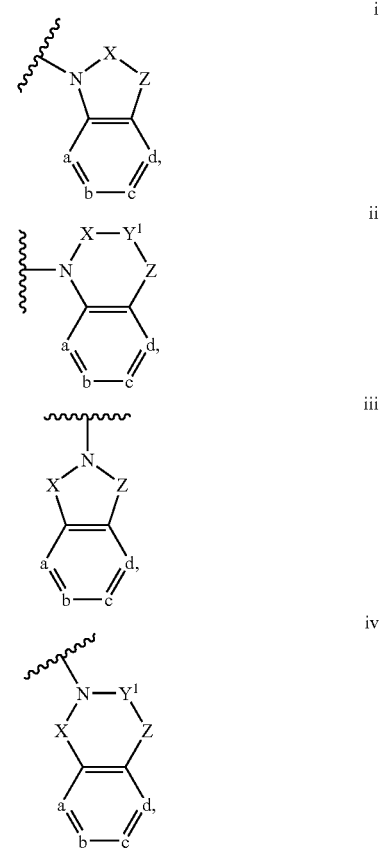

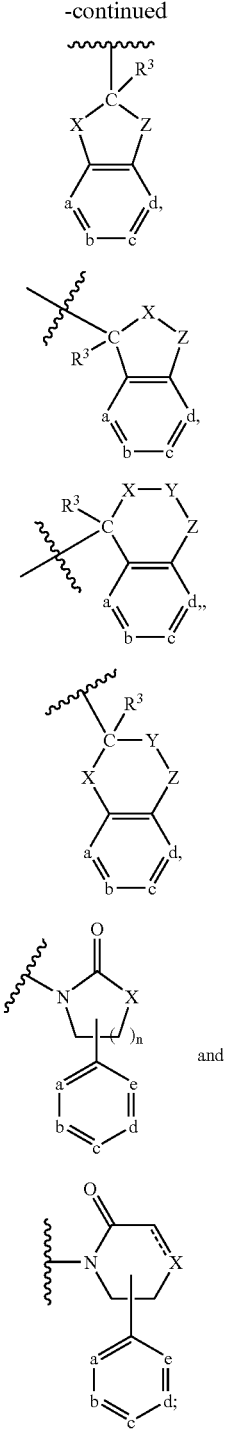

wherein in:

a) Formulae i and ii, the symbols X, Y and Z are each independently selected from the group consisting of —CH$_2$—, —CHR$^3$—, —C(R$^3$)$_2$—, —NR$^3$—, —NH—, —S—, —O—, —C(O)—, —S(O)— and —S(O)$_2$—; or optionally any two substituents on the adjacent atoms of X and Y$^1$, or Y$^1$ and Z may be absent and replaced with a bond to form a double bond between X and Y$^1$, or Y$^1$ and Z; and each of ring vertices a, b, c and d is independently selected from the group consisting of N, N$^+$—O$^-$, C(H) and C(R$^3$), and from 0-2 ring vertices is N or N$^+$—O$^-$;

b) Formulae iii and iv, X, Y and Z are each independently selected from the group consisting of —CH$_2$—, —CHR$^3$—, —C(R$^3$)$_2$—, —C(O)—, —NH— and —N(R$^3$), —O—, —S—, —S(O)— and —S(O)$_2$—; or optionally any two substituents on adjacent atoms of one of Y and Z may be absent and replaced with a bond to form a double bond between Y and Z; and each of ring vertices a, b, c and d is independently selected from the group consisting of N, N$^+$—O$^-$, C(H) and C(R$^3$), and from 0-2 ring vertices is N or N—O$^-$;

c) Formulae v, vi, vii and viii, X, Y and Z are each independently selected from the group consisting of —CH$_2$—, —CHR$^3$—, —C(R$^3$)$_2$, —C(O)—, —S(O)—, —S(O)$_2$—, —NH—, —N(R$^3$), —S— and —O—, wherein at least one of X, Y and Z is —NH— or —N(R$^3$)—; optionally any two substituents on adjacent atoms of X and C, C and Y, X and Y, X and Z, or Y and Z may be absent and replaced with a bond to form a double bond between X and C, C and Y, X and Y, X and Z, or Y and Z; each of ring vertices a, b, c and d is independently selected from the group consisting of N, N$^+$—O$^-$, —CH— and C(R$^3$), and from 0-2 ring vertices is N or N$^+$—O$^-$;

d) Formulae ix and x, X is selected from the group consisting of C, N, O and S; optionally any two R$^3$ substituents on -B$^1$ located on adjacent atoms are absent and replaced with a bond to form a double bond; the subscript o is 0-2 and the subscript n is from 1-2; and each of ring vertices a, b, c d and e is independently selected from the group consisting of N, N$^+$—O$^-$, —C(H)— and C(R$^3$), and from 0-2 ring vertices is N or N$^+$—O$^-$; and the bond, -----, represents a single or double bond;

The symbol L$^1$ is a linking group selected from the group consisting of C$_{1-3}$ alkylene, C$_{1-3}$ heteroalkylene. The symbol U is selected from the group consisting of N, C—R$^p$ and N$^+$—O$^-$, wherein R$^p$ is —OH, C$_{1-3}$ alkylene-OR$^q$, —NH$_2$, —NHC(O)R$^q$, NHR$^q$, —NHCONH$_2$, —NHC(=NH)NH$_2$, —NHC(=NH)R$^q$, C$_{1-3}$ alkylene-NH(R$^q$), —OR$^q$, —R$^q$, —CN, —NO$_2$, —CO$_2$H, or —CO$_2$R$^q$, wherein R$^q$ is each independently C$_{1-8}$ alkyl, C$_{1-8}$ haloalkyl, C$_{3-8}$ cycloalkyl wherein the aliphatic portions of R$^q$ is optionally further substituted with from one to three members selected from the group consisting of —OH, —OR$^r$, —OC(O)NHR$^r$, —OC(O)N(R$^r$)$_2$, —SH, —SR$^r$, —S(O)R$^r$, —S(O)$_2$R$^r$, —SO$_2$NH$_2$, —S(O)$_2$NHR$^r$, —S(O)$_2$N(R$^e$)$_2$, —NHS(O)$_2$R$^r$, —NR$^r$S(O)$_2$R$^r$, —C(O)NH$_2$, —C(O)NHR$^r$, —C(O)N(R$^r$)$_2$, —C(O)R$^r$, —NHC(O)R$^r$, —NR$^q$C(O)R$^r$, —NHC(O)NH$_2$, —NR$^r$C(O)NH$_2$, —NR$^r$C(O)NHR$^r$, —NHC(O)NHR$^r$, —NR$^r$C(O)N(R$^r$)$_2$, —NHC(O)N(R$^r$)$_2$, —CO$_2$H, —CO$_2$R$^r$, —NHCO$_2$R$^r$, —NR$^r$CO$_2$R$^r$, —CN, —NO$_2$, —NH$_2$, —NHR$^r$, —N(R$^r$)$_2$, NR$^r$S(O)NH$_2$ and —NR$^r$S(O)$_2$NHR$^r$, wherein each R$^r$ is independently an unsubstituted C$_{1-6}$ alkyl. The symbol L$^2$ is a linking group selected from the group consisting of a direct bond, C$_{1-3}$ alkylene, —O—, —NR$^s$—, —C(O)—, —C(R$^s$)$_2$—, —S(O)—, —S(O)$_2$—, —NR$^s$C(O)— and —NR$^s$S(O)$_2$—, wherein R$^s$ is at each occurrence is independently selected from the group consisting of hydrogen, C$_{1-8}$ alkyl, C$_{1-8}$ haloalkyl, C$_{3-6}$ cycloalkyl, C$_{2-8}$ alkenyl, C$_{2-8}$ alkynyl, C$_{6-10}$ aryl and C$_{5-10}$ heteroaryl wherein the aliphatic portion of R$^s$ are optionally further substituted with from one to three members selected from the group consisting of —OH, —OR$^t$, —OC(O)NHR$^t$, —OC(O)N(R$^t$)$_2$, —SH, —SR$^t$, —S(O)R$^t$, —S(O)$_2$R$^t$, —SO$_2$NH$_2$, —S(O)$_2$NHR$^t$, —S(O)₂N(Rᵗ)₂, —NHS(O)₂Rᵗ, —NRʹS(O)₂Rᵗ, —C(O)NH₂, —C(O)NHRᵗ, —C(O)N(Rᵗ)₂, —C(O)Rᵗ, —NHC(O)Rᵗ, —NRʹC(O)Rᵗ, —NHC(O)NH₂, —NRʹC(O)NH₂, —NRʹC(O)NHRᵗ, —NHC(O)NHRᵗ, —NRʹC(O)N(Rᵗ)₂, —NHC(O)N(Rᵗ)₂, —CO₂H, —CO₂Rᵗ, —NHCO₂Rᵗ, —NRʹCO₂Rᵗ, —CN, —NO₂, —NH₂, —NHRᵗ, —N(Rᵗ)₂, —NRʹS(O)NH₂ and —NRʹS(O)₂NHRᵗ, wherein each Rᵗ is independently an unsubstituted $C_{1-6}$ alkyl or $C_{1-6}$ haloalkyl.

A family of specific compound of particular interest having Formulae Ia and Ib consists of compounds, pharmaceutically acceptable salts, hydrates or N-oxides thereof, as set forth in Table 1.

TABLE 1

1. 5-chloro-1-{2-[4-(4-chloro-3-methoxy-phenyl)-piperazin-1-yl]-2-oxoethyl}-1,3-dihydro-indol-2-one
2. 6-chloro-3-{2-[4-(4-chloro-3-methoxy-phenyl)-piperazin-1-yl]-2-oxo-ethyl}-3H-benzooxazol-2-one
3. 6-Chloro-3-{2-[4-(4-chloro-2-fluoro-5-methoxy-phenyl)-piperazin-1-yl]-2-oxo-ethyl}-3H-benzooxazol-2-one
4. 6-Chloro-3-{2-[(S)-4-(4-chloro-2-fluoro-5-methoxy-phenyl)-2-methyl-piperazin-1-yl]-2-oxo-ethyl}-3H-benzooxazol-2-one
5. 6-Chloro-3-{2-[(S)-4-(4-chloro-3-methoxy-phenyl)-2-methylpiperazin-1-yl]-2-oxo-ethyl}-3H-benzooxazol-2-one
6. Synthesis of 5-Chloro-1-{2-[4-(4-chloro-3-methoxy-phenyl)-piperazin-1-yl]-2-oxo-ethyl}-1,3-dihydro-benzoimidazol-2-one
7. 6-Chloro-1-{2-[4-(4-chloro-3-methoxy-phenyl)-piperazin-1-yl]-2-oxo-ethyl}-1,3-dihydro-benzoimidazol-2-one.
8. (6-Chloro-3-{2-[4-(4-chloro-3-methoxy-phenyl)-piperazin-1-yl]-2-oxo-ethyl}-2-oxo-2,3-dihydro-benzoimidazol-1-yl)-acetic acid ethyl ester
9. (5-Chloro-3-{2-[4-(4-chloro-3-methoxy-phenyl)-piperazin-1-yl]-2-oxo-ethyl}-2-oxo-2,3-dihydro-benzoimidazol-1-yl)-acetic acid ethyl ester
10. (6-Chloro-3-{2-[4-(4-chloro-3-methoxy-phenyl)-piperazin-1-yl]-2-oxo-ethyl}-2-oxo-2,3-dihydro-benzoimidazol-1-yl)-acetic acid
11. (5-Chloro-3-{2-[4-(4-chloro-3-methoxy-phenyl)-piperazin-1-yl]-2-oxo-ethyl}-2-oxo-2,3-dihydrobenzoimidazol-1-yl)-acetic acid
12. 6-chloro-3-{2-[4-(4-fluoro-benzyl)-piperazin-1-yl]-2-oxo-ethyl}-3H-benzooxazol-2-one
13. 3-{2-[4-(4-chloro-3-methoxy-phenyl)-piperazin-1-yl]-2-oxo-ethyl}-3H-benzooxazol-2-one
14. 5-chloro-3-{2-[4-(4-chloro-3-methoxy-phenyl)-piperazin-1-yl]-2-oxo-ethyl}-3H-benzooxazol-2-one
15. 6-methoxy-3-{2-[4-(4-chloro-3-methoxy-phenyl)-piperazin-1-yl]-2-oxo-ethyl}-3H-benzooxazol-2-one
16. 6-fluoro-3-{2-[4-(4-chloro-3-methoxy-phenyl)-piperazin-1-yl]-2-oxo-ethyl}-3H-benzooxazol-2-one
17. 1-{2-[4-(4-chloro-3-methoxy-phenyl)-piperazin-1-yl]-2-oxo-ethyl}-3-methyl-1,3-dihydro-benzoimidazol-2-one
18. 1-{2-[4-(4-chloro-3-methoxy-phenyl)-piperazin-1-yl]-2-oxo-ethyl}-oxazolidin-2-one.
19. 1-{2-[4-(4-chloro-3-methoxy-phenyl)-piperazin-1-yl]-2-oxo-ethyl}-imidazolidin-2-one
20. 1-[4-(4-chloro-3-methoxy-phenyl)-piperazin-1-yl]-2-((2S,6R)-2,6-dimethyl-piperidin-1-yl)-ethanone
21. 1-[4-(4-chloro-3-methoxy-phenyl)-piperazin-1-yl]-2-morpholin-4-yl-ethanone
22. 1-[4-(4-chloro-3-methoxy-phenyl)-piperazin-1-yl]-2-(4-methyl-piperazin-1-yl)-ethanone
23. 1-[4-(4-chloro-3-methoxy-phenyl)-piperazin-1-yl]-2-piperazin-1-yl-ethanone
24. 7-Chloro-4-{2-[4-(4-chloro-3-methoxy-phenyl)-piperazin-1-yl]-2-oxo-ethyl}-4H-benzo[1,4]oxazin-3-one
25. 6-Chloro-4-{2-[4-(4-chloro-3-methoxy-phenyl)-piperazin-1-yl]-2-oxo-ethyl}-4H-benzo[1,4]oxazin-3-one
26. 4-{2-[4-(4-Chloro-3-methoxy-phenyl)-piperazin-1-yl]-2-oxo-ethyl}-4H-benzo[1,4]oxazin-3-one
27. 4-{2-[4-(4-Chloro-3-methoxy-phenyl)-piperazin-1-yl]-2-oxo-ethyl}-4H-oxazolo[4,5-b]pyridin-2-one
28. 4-{2-[4-(4-Chloro-2-fluoro-5-methoxy-phenyl)-piperazin-1-yl]-2-oxo-ethyl}-4H-oxazolo[4,5-b]pyridin-2-one
29. 3-{2-[4-(4-Chloro-2-fluoro-5-methoxy-phenyl)-piperazin-1-yl]-2-oxo-ethyl}-3H-oxazolo[4,5-b]pyridin-2-one
30. 6-Chloro-3-{2-[4-(4-chloro-2-fluoro-5-methoxy-phenyl)-piperazin-1-yl]-2-oxo-ethyl}-3H-oxazolo[4,5-b]pyridin-2-one
31. 7-Chloro-4-{2-[4-(4-chloro-2-fluoro-5-methoxy-phenyl)-piperazin-1-yl]-2-oxo-ethyl}-4H-pyrido[3,2-b][1,4]oxazin-3-one
32. 3-{2-[4-(4-Chloro-3-methoxy-phenyl)-piperazin-1-yl]-2-oxo-ethyl}-4-phenyl-oxazolidin-2-one
33. 3-{2-[4-(4-Chloro-3-methoxy-phenyl)-piperazin-1-yl]-2-oxo-ethyl}-5-phenyl-oxazolidin-2-one
34. (3-{2-[4-(4-Chloro-3-methoxy-phenyl)-piperazin-1-yl]-2-oxo-ethyl}-2-oxo-2,3-dihydro-benzooxazol-6-yloxy)-acetic acid
35. 3-{2-[4-(4-Chloro-3-methoxy-phenyl)-piperazin-1-yl]-2-oxo-ethyl}-6-[1,2,4]oxadiazol-3-yl-3H-benzooxazol-2-one
36. 3-{2-[4-(4-Chloro-3-methoxy-phenyl)-piperazin-1-yl]-2-oxo-ethyl}-6-(2-hydroxy-ethoxy)-3H-benzooxazol-2-one TABLE 1-continued 37. 6-(2-Amino-ethoxy)-3-{2-[4-(4-chloro-3-methoxy-phenyl)-piperazin-1-yl]-2-oxo-ethyl}-3H-benzooxazol-2-one
38. 5-Chloro-1-{2-[4-(4-chloro-3-methoxy-phenyl)-piperazin-1-yl]-2-oxo-ethyl}-3-methyl-1,3-dihydro-benzoimidazol-2-one
39. {1-(4-chloro-3-methoxy-phenyl)-4-[2-(6-chloro-2-oxo-2,3-dihydro-benzofuran-3-yl)-acetyl]-piperazin-2-yl}-acetic acid methyl ester
40. 5-chloro-3-{2-[4-(4-chloro-3-methoxy-phenyl)-piperazin-1-yl]-2-oxo-ethyl}-1-methyl-1,3-dihydro-benzoimidazol-2-one
41. 3-(2-(4-(4-Fluorobenzyl)-4-hydroxypiperidin-1-yl)-2-oxoethyl)-6-chlorobenzo[d]oxazol-2(3H)-one
42. 6-Chloro-3-{2-[4-(4-chloro-3-methoxy-phenyl)-4-hydroxy-piperidin-1-yl]-2-oxo-ethyl}-3H-benzooxazol-2-one
43. 6-Chloro-1-{2-[4-(4-chloro-3-methoxy-phenyl)-piperazin-1-yl]-2-oxo-ethyl}-1,4-dihydro-benzo[d][1,3]oxazin-2-one
44. 6-chloro-3-{2-[3-(3-chloro-2-methyl-phenyl)-4-oxo-imidazolidin-1-yl]-2-oxo-ethyl}-3H-benzooxazol-2-one
45. 5-Chloro-1-{2-[4-(4-fluoro-benzyl)-4-hydroxy-piperidin-1-yl]-2-oxo-ethyl}-1,3-dihydro-benzoimidazol-2-one
46. 6-Chloro-1-{2-[4-(4-fluoro-benzyl)-4-hydroxy-piperidin-1-yl]-2-oxo-ethyl}-1,3-dihydro-benzoimidazol-2-one Preparation of Compounds As provided in the examples below, the compounds and intermediates of the present invention can be prepared by one of skill in the art in a component assembly manner. Schemes 1A-1L illustrate a variety of methods for the preparation of a variety of monocyclic and bicyclic groups and derivatives. In each of these schemes, X is halogen; U is —NH—, —O—, —CR'''R'''—, or —NR'''—; the symbol Ⓝ within an aryl ring indicate the replacement of one to two carbon(s) of said aryl ring vertex (vertices) with nitrogen atom(s); L is a ligand; and non-interferring substituents are provided as —R, —R', —R", and —R'''.

Scheme 1A

Scheme 1A shows the synthesis of a bicyclic group of the invention.

Scheme 1B

Scheme 1B shows the synthesis of a bicyclic group of the invention.

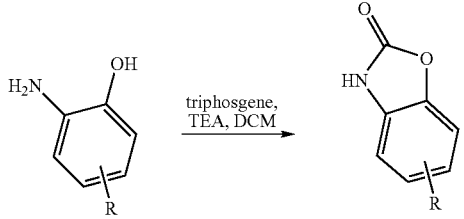

Scheme 1C

Scheme 1C shows the synthesis of a bicyclic group of the invention.

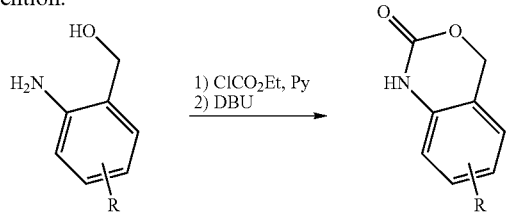

Scheme 1D

Scheme 1D shows a halogenation reaction of a bicyclic group of the invention

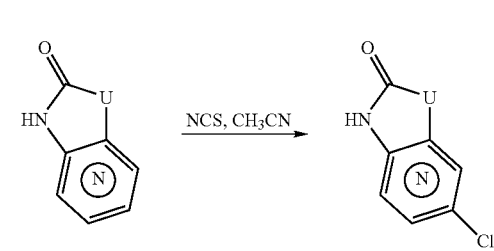

Scheme 1E

Scheme 1E shows a halogenation reaction of a bicyclic group of the invention

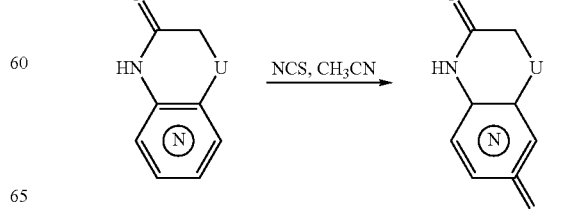

Scheme 1F

Scheme 1F shows the cyanation of a bicyclic group of the invention.

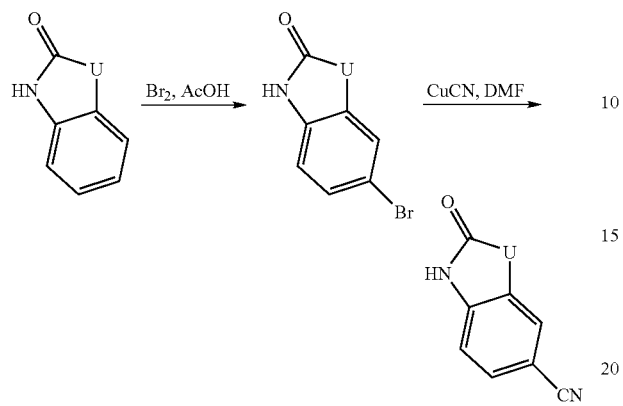

Scheme 1G

Scheme 1G shows the synthesis of a bicyclic compound of the invention.

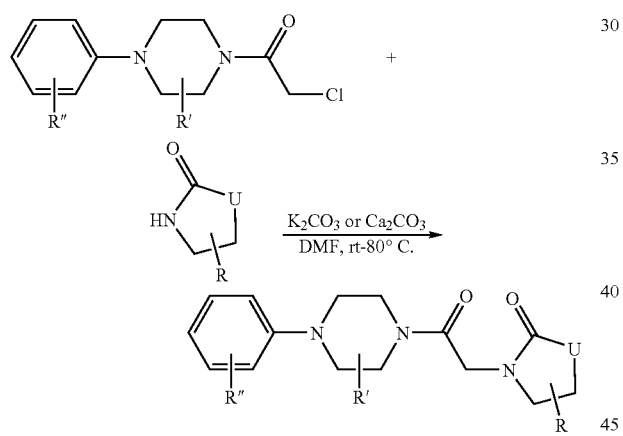

Scheme 1H

Scheme 1H shows the synthesis of a bicyclic compound of the invention.

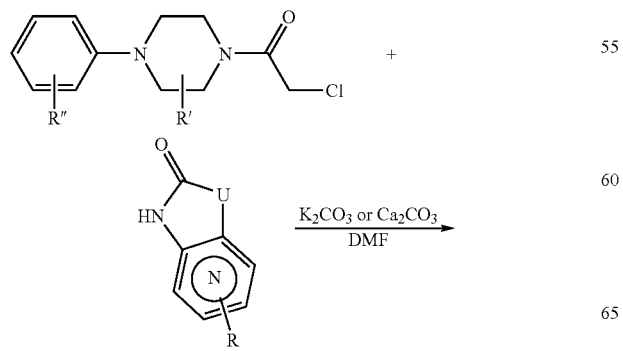

-continued

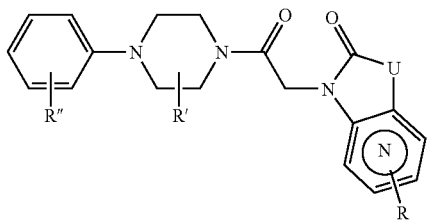

Scheme 1I

Scheme 1I shows the functionalization of a bicyclic compound of the invention.

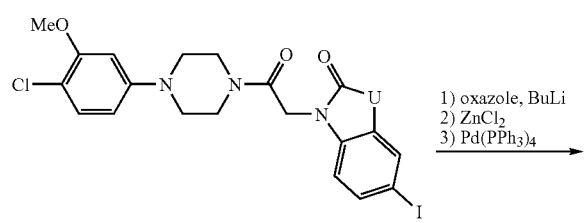

Scheme 1J

Scheme 1J shows the functionalization of a bicyclic compound of the invention.

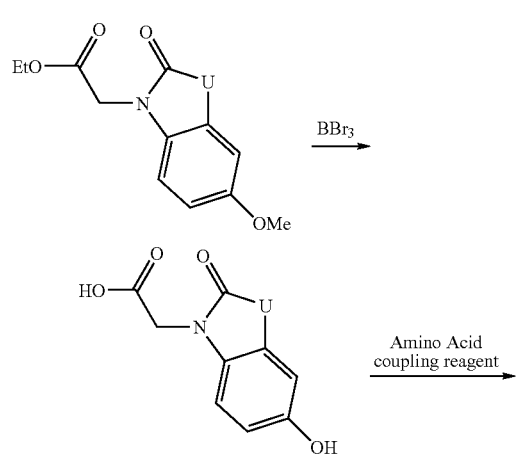

47

-continued

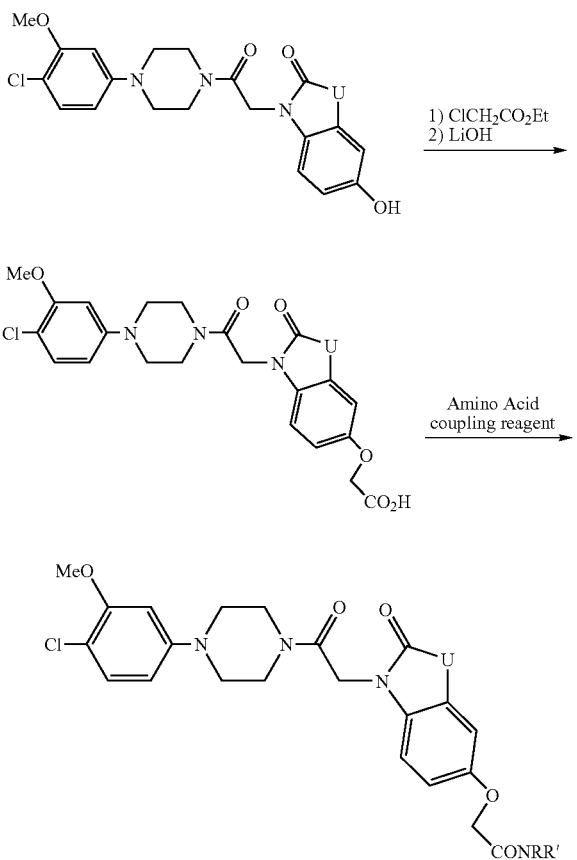

Scheme 1K

Scheme 1K shows the alkylation of a bicyclic compound of the invention.

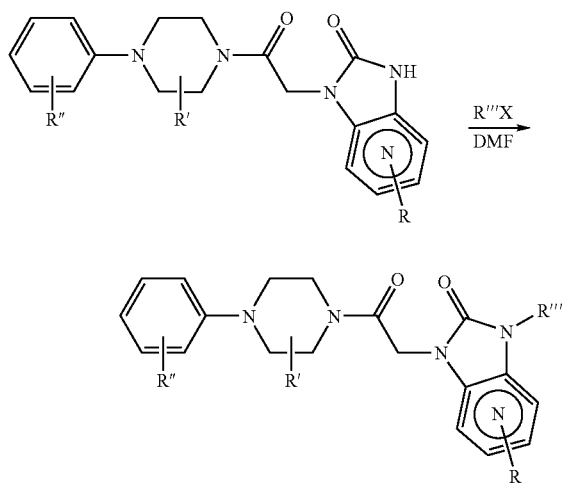

48

Scheme 1L

Scheme 1L shows the alkylation reaction of a bicyclic compound of the invention.

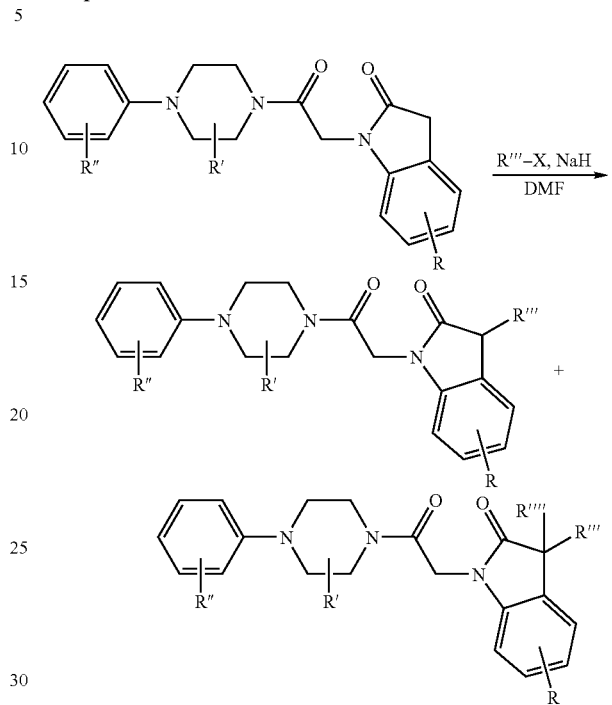

IV. Pharmaceutical Compositions

In addition to the compounds provided above, compositions for modulating CCR1 activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of this invention may also be coupled a carrier that is a suitable polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the invention may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like. In one embodiment of the invention, the compound of the invention is coupled to a polymer or semipermeable polymer matrix that is formed as a stent or stent-graft device.

V. Methods of Treating Diseases Modulated by CCR1

In yet another aspect, the present invention provides methods of treating CCR1-mediated conditions or diseases by administering to a subject having such a disease or condition, a therapeutically effective amount of a compound of Formula I above. The "subject" is defined herein to include animals such as mammals, including, but not limited to, primates (e.g., humans), cows, sheep, goats, horses, dogs, cats, rabbits, rats, mice and the like.

CCR1 provides a target for interfering with or promoting specific aspects of immune cell functions, or more generally, with functions associated with CCR1 expression on a wide range of cell types in a mammal, such as a human. Compounds that inhibit CCR1, are particularly useful for modulating monocyte, macrophage, lymphocyte, granulocyte, NK cell, mast cells, dendritic cell, neutrophils, and certain immune derived cell (for example, osteoclasts) function for therapeutic purposes. Accordingly, the present invention is directed to compounds which are useful in the prevention and/or treatment of a wide variety of inflammatory and immunoregulatory disorders and diseases (see Saeki, et al., *Current Pharmaceutical Design* 9:1201-1208 (2003)).

For example, an instant compound that inhibits one or more functions of CCR1 may be administered to inhibit (i.e., reduce or prevent) inflammation or cellular infiltration associated with an immune disorder. As a result, one or more inflammatory processes, such as leukocyte emigration or infiltration, chemotaxis, exocytosis (e.g., of enzymes, histamine) or inflammatory mediator release, can be inhibited. For example, monocyte infiltration to an inflammatory site (e.g., an affected joint in arthritis, or into the CNS in MS) can be inhibited according to the present method.

Similarly, an instant compound that promotes one or more functions of CCR1 is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, monocytes can be recruited to combat bacterial infections.

Diseases and conditions associated with inflammation, immune disorders and infection can be treated using the method of the present invention. In a preferred embodiment, the disease or condition is one in which the actions of immune cells such monocyte, macrophage, lymphocyte, granulocyte, NK cell, mast cell, dendritic cell, or certain immune derived cell (for example, osteoclasts) are to be inhibited or promoted, in order to modulate the inflammatory or autoimmune response.

In one group of embodiments, diseases or conditions, including chronic diseases, of humans or other species can treated with modulators of CCR1 function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as allergic asthma, allergic rhinitis, hypersensitivity lung diseases and the like, (9) autoimmune diseases, such as fibromyalgia, scleroderma, ankylosing spondylitis, juvenile RA, Still's disease, polyarticular juvenile RA, pauciarticular juvenile RA, polymyalgia rheumatica, rheumatoid arthritis, psoriatic arthritis, osteoarthritis, polyarticular arthritis, multiple sclerosis, systemic lupus erythematosus, type I diabetes, type II diabetes, glomerulonephritis, and the like, (10) graft rejection (including allograft rejection and graft-v-host disease), and (11) other diseases in which undesired inflammatory responses or immune disorders are to be inhibited, such as cardiovascular disease including atherosclerosis and restenosis, myositis, neurodegenerative diseases (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout and (12) immune mediated food allergies such as Celiac disease.

In another group of embodiments, diseases or conditions can be treated with modulators of CCR1 function. Examples of diseases to be treated with modulators of CCR1 function include cancers, cardiovascular diseases, diseases in which angiogenesis or neovascularization play a role (neoplastic diseases, retinopathy and macular degeneration), infectious diseases (viral infections, e.g., HIV infection, and bacterial infections) and immunosuppressive diseases such as organ transplant conditions and skin transplant conditions. The term "organ transplant conditions" is meant to include bone marrow transplant conditions and solid organ (e.g., kidney, liver, lung, heart, pancreas or combination thereof) transplant conditions.

The compounds of the present invention are accordingly useful in the prevention and treatment of a wide variety of inflammatory and immunoregulatory disorders and diseases.

Depending on the disease to be treated and the subject's condition, the compounds of the present invention may be administered by oral, parenteral (e.g., intramuscular, intraperitoneal, intravenous, ICV, intracisternal injection or infusion, subcutaneous injection, or implant), by implantation (e.g., as when the compound is coupled to a stent device), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

Diseases and conditions associated with inflammation, immune disorder, infection and cancer can be treated or prevented with the present compounds, compositions, and methods.

The compounds and compositions of the present invention can be combined with other compounds and compositions having related utilities to prevent and treat the condition or disease of interest, such as inflammatory or autoimmune disorders, conditions and diseases, including inflammatory bowel disease, rheumatoid arthritis, osteoarthritis, psoriatic arthritis, polyarticular arthritis, multiple sclerosis, allergic diseases, psoriasis, atopic dermatitis and asthma, and those pathologies noted above.

For example, in the treatment or prevention of inflammation or autoimmunity or for example arthritis associated bone loss, the present compounds and compositions may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds and compositions may be administered with an analgesic listed above; a potentiator such as caffeine, an H2 antagonist (e.g., ranitidine), simethicone, aluminum or magnesium hydroxide; a decongestant such as phenylephrine, phenylpropanolamine, pseudoephedrine, oxymetazoline, ephinephrine, naphazoline, xylometazoline, propylhexedrine, or levo desoxy ephedrine; an antitussive such as codeine, hydrocodone, caramiphen, carbetapentane, or dextromethorphan; a diuretic; and a sedating or non sedating antihistamine.

Likewise, compounds and compositions of the present invention may be used in combination with other drugs that are used in the treatment, prevention, suppression or amelioration of the diseases or conditions for which compounds and compositions of the present invention are useful. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, dexamethasone, fluticasone, hydrocortisone, budesonide, triamcinolone, salmeterol, salmeterol, salbutamol, formeterol; (c) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchloipheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non steroidal anti asthmatics (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafmlukast, montelukast, pranlukast, iralukast, pobilukast and SKB-106,203), leukotriene biosynthesis inhibitors (zileuton, BAY-1005); (f) non steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE IV); (i) gold compounds such as auranofin and aurothioglucose, (j) etanercept (Enbrel®), (k) antibody therapies such as orthoclone (OKT3), daclizumab (Zenapax®), basiliximab (Simulect®) and infliximab (Remicade®), (l) other antagonists of the chemokine receptors, especially CCR5, CXCR2, CXCR3, CCR2, CCR3, CCR4, CCR7, $CX_3CR1$ and CXCR6; (m) lubricants or emollients such as petrolatum and lanolin, (n) keratolytic agents (e.g., tazarotene), (o) vitamin $D_3$ derivatives, e.g., calcipotriene or calcipotriol (Dovonex®), (p) PUVA, (q) anthralin (Drithrocreme®), (r) etretinate (Tegison®) and isotretinoin and (s) multiple sclerosis therapeutic agents such as interferon β-1β (Betaseron®), interferon (β-1α (Avonex®), azathioprine (Imurek®, Imuran®), glatiramer acetate (Capoxone®), a glucocorticoid (e.g., prednisolone) and cyclophosphamide (t) DMARDS such as methotrexate (u) other compounds such as 5-aminosalicylic acid and prodrugs thereof; hydroxychloroquine; D-penicillamine; antimetabolites such as azathioprine, 6-mercaptopurine and methotrexate; DNA synthesis inhibitors such as hydroxyurea and microtubule disrupters such as colchicine. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

VI. Examples

The following examples are offered to illustrate, but not to limit the claimed invention.

Reagents and solvents used below can be obtained from commercial sources such as Aldrich Chemical Co. (Milwaukee, Wis., USA). $^1$H-NMR spectra were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In the examples, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol at 0.1 mg/mL and 1 microlitre was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM NH$_4$OAc in acetonitrile/water as delivery system.

The following abbreviations are used in the Examples set forth herein:
NMP: N-methyl-2-pyrrolidinone
HPLC: High Pressure Liquid Chromatography
DMF: Dimethyl formamide
TFA: Trifluoroacetic Acid
THF: Tetrahydrofuran
NCS: N-Chlorosuccinimide
EtOAc: Ethyl acetate
DCM: Dichloromethane
HATU: N,N,N',N'-Tetramethyl-O-(7-azabenzotriazol-1-yl) uronium hexafluorophosphate
DMA: Dimethylacetamide
DIPEA: Diisopropylethylamine
BOP: (Benzotriazol-1-yloxy)tris(dimethylamino)phosphonium hexafluorophosphate
DBU: 1,8-diazabicyclo(5.4.0)undec-7-ene Compounds within the scope of this invention can be synthesized as described below, using a variety of reactions known to the skilled artisan. A sample of useful routes to the azaindazole derivatives and certain compounds of the invention are provided below or elsewhere within the present application. In the descriptions of the syntheses that follow, some of the arylpiperazine and heteroaromatic subunit precursors were obtained from commercial sources. These commercial sources include Aldrich Chemical Co., Acros Organics, Ryan Scientific Incorporated, Oakwood Products Incorporated, Lancaster Chemicals, Sigma Chemical Co., Lancaster Chemical Co., TCI-America, Alfa Aesar, Davos Chemicals, and GFS Chemicals. Certain relevant arylpiperazine compounds can be commercially obtained. Others could be prepared as described in U.S. patent application Ser. No. 11/008, 774, the contents of which is hereby incorporated in its entirety for all purposes. Also, standard chemistries have been employed to link the arylpiperazine and heteroaromatic subunits (whether commercially obtained or prepared by the methods below) using a suitably optimized linker, such as the acetyl unit described in the body of this invention.

One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

Regioisomerism is a common property in organic chemistry, and is especially common with regards to certain structural types provided herein. Those skilled in the art will recognize, with respect to the compounds described herein, that the coupling reactions with the heteroaromatic ring systems can lead to either one of or a mixture of detectable regioisomers.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1

Synthesis of 5-chloro-1-{2-[4-(4-chloro-3-methoxy-phenyl)-piperazin-1-yl]-2-oxoethyl}-1,3-dihydro-indol-2-one (2)

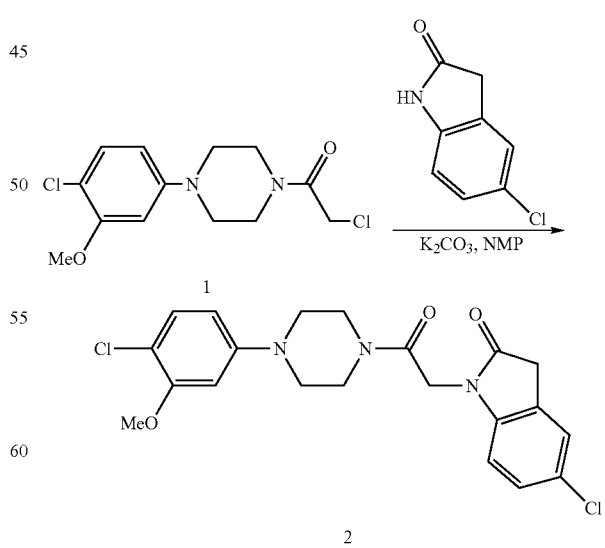

In a 4 mL vial was added 2-chloro-1-[4-(4-chloro-3-methoxy-phenyl)-piperazin-1-yl]-ethanone (1) (200 mg, 0.66 mmol, 1.0 equiv), 5-chloro-1,3-dihydro-indol-2-one (116 mg, 0.69 mmol, 1.05 equiv), $K_2CO_3$ (365 mg, 2.64 mmol, 4.0 equiv) and 2.5 mL N-methylpyrrolidinone (NMP). A stir bar was placed in the vial and the vial was then capped. The resultant mixture stirred at 60° C. overnight. The crude product was purified by reversed phase HPLC (acetonitrile —$H_2O$ with 0.1% TFA as the eluent) to yield 5-chloro-1-{2-[4-(4-chloro-3-methoxy-phenyl)-piperazin-1-yl]-2-oxoethyl}-1,3-dihydro-indol-2-one (2): HPLC retention time, 2.47 minutes, (Agilent Zorbax SB-C18, 2.1×50 mm, 5μ, 35° C.) using 1 ml/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expected, 434.3, found, 434.4.

Example 2

Synthesis of 6-chloro-3-{2-[4-(4-chloro-3-methoxy-phenyl)-piperazin-1-yl]-2-oxo-ethyl}-3H-benzooxazol-2-one (3)

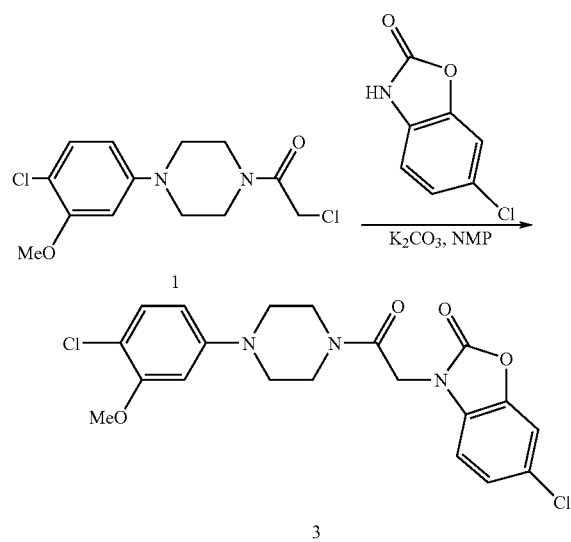

In a 4 mL vial was added 2-chloro-1-[4-(4-chloro-3-methoxy-phenyl)-piperazin-1-yl]-ethanone (1) (200 mg, 0.66 mmol, 1.0 equiv), 6-chloro-3H-benzooxazol-2-one (105 mg, 0.69 mmol, 1.05 equiv), $K_2CO_3$ (365 mg, 2.64 mmol, 4.0 equiv) and 2.5 mL of NMP. A stir bar was placed in the vial and the vial was then capped. The resultant mixture stirred at 60° C. overnight. The crude product was purified by reversed phase HPLC (acetonitrile —$H_2O$ with 0.1% TFA as the eluent) to yield 6-chloro-3-{2-[4-(4-chloro-3-methoxy-phenyl)-piperazin-1-yl]-2-oxo-ethyl}-3H-benzooxazol-2-one (3): HPLC retention time, 2.62 minutes (Agilent Zorbax SB-C18, 2.1×50 mm, 5μ, 35° C.) using 1 ml/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expected, 436.3, found, 436.4.

Example 3

Synthesis of 6-Chloro-3-{2-[4-(4-chloro-2-fluoro-5-methoxy-phenyl)-piperazin-1-yl]-2-oxo-ethyl}-3H-benzooxazol-2-one (5)

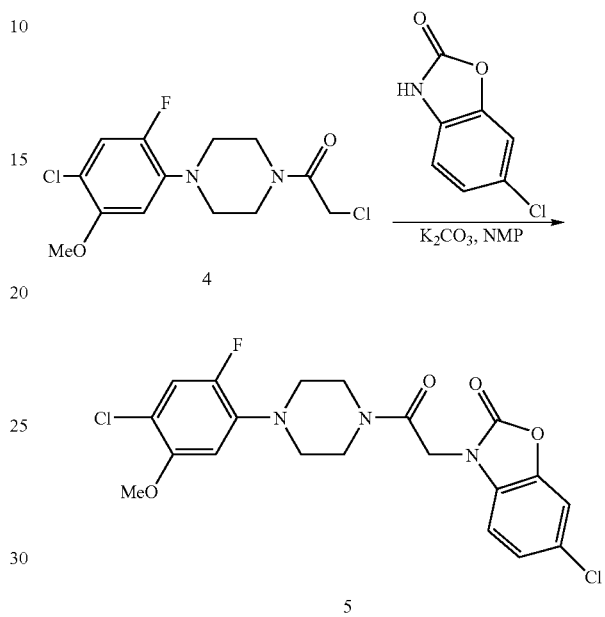

Compound 5 was prepared according to the procedure described in Example 2 using 2-chloro-1-[4-(4-chloro-2-fluoro-5-methoxy-phenyl)-piperazin-1-yl]-ethanone (4), 6-chloro-3H-benzooxazol-2-one and $K_2CO_3$ in DMF: HPLC retention time, 2.70 minutes, (Agilent Zorbax SB-C18, 2.1× 50 mm, 5μ, 35° C.) using 1 ml/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expected, 454.3, found, 454.4.

Example 4

Synthesis of 6-Chloro-3-{2-[(S)-4-(4-chloro-2-fluoro-5-methoxy-phenyl)-2-methyl-piperazin-1-yl]-2-oxo-ethyl}-3H-benzooxazol-2-one (7)

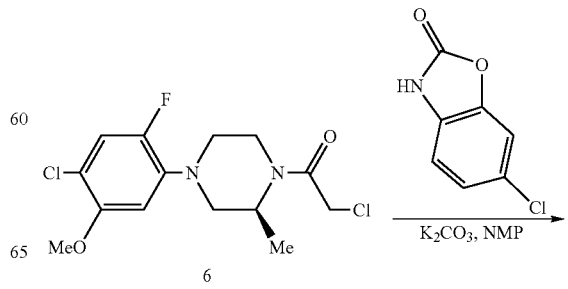

-continued

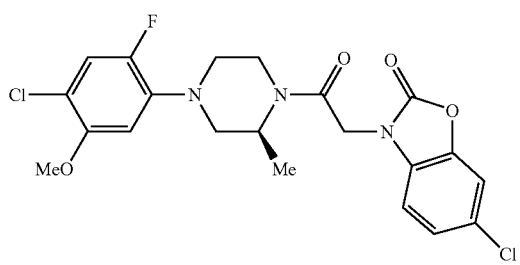

7

Compound 7 was prepared according to the procedure described in Example 2 using 2-chloro-1-[(S)-4-(4-chloro-2-fluoro-5-methoxy-phenyl)-2-methyl-piperazin-1-yl]-ethanone (6), 6-chloro-3H-benzooxazol-2-one and K₂CO₃ in DMF: HPLC retention time, 2.87 minutes (Agilent Zorbax SB-C18, 2.1×50 mm, 5µ, 35° C.) using 1 ml/min flow rate, a 2.5 minute gradient of 20% to 100% B with a 1.1 minute wash at 100% B (A, 0.1% formic acid/5% acetonitrile/94.9% water, B, 0.1% formic acid/5% water/94.9% acetonitrile); MS (ES) M+H expected, 468.3, found, 468.4.

Example 5

Synthesis of 6-Chloro-3-{2-[(S)-4-(4-chloro-3-methoxy-phenyl)-2methylpiperazin-1-yl]-2-oxo-ethyl}-3H-benzooxazol-2-one (9)

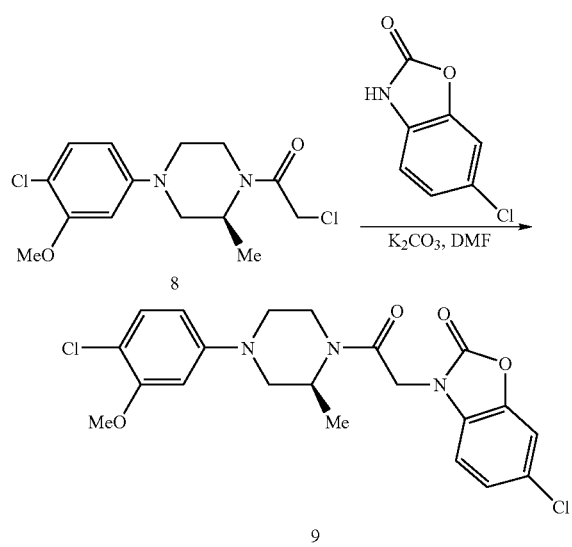

Compound 9 was prepared according to the procedure described in Example 2 using 2-chloro-1-[(S)-4-(4-chloro-5-methoxy-phenyl)-2-methyl-piperazin-1-yl]-ethanone (8), 6-chloro-3H-benzooxazol-2-one and K₂CO₃ in DMF: HPLC retention time, 2.75 minutes (Agilent Zorbax SB-C18, 2.1× 50 mm, 5µ, 35° C.) using 1 ml/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expected, 450.4, found, 450.4.

Example 6

Synthesis of 5-Chloro-1-{2-[4-(4-chloro-3-methoxy-phenyl)-piperazin-1-yl]-2-oxo-ethyl}-1,3-dihydro-benzoimidazol-2-one (10a) and 6-Chloro-1-{2-[4-(4-chloro-3-methoxy-phenyl)-piperazin-1-yl]-2-oxo-ethyl}-1,3-dihydro-benzoimidazol-2-one (10b)

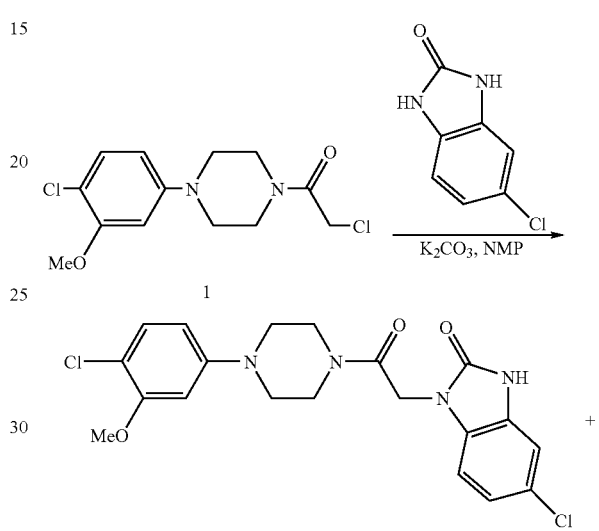

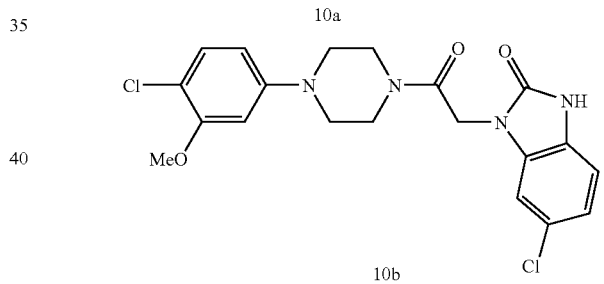

In a 4 mL vial was added 2-chloro-1-[4-(4-chloro-3-methoxy-phenyl)-piperazin-1-yl]-ethanone (1) (200 mg, 0.66 mmol, 1.0 equiv), 5-Chloro-1,3-dihydro-benzoimidazol-2-one (117 mg, 0.69 mmol, 1.05 equiv), K₂CO₃ (365 mg, 2.64 mmol, 4.0 equiv) and 2.5 mL of NMP. A stir bar was placed in the vial and the vial was then capped. The resultant mixture stirred at 60° C. overnight. The crude product was purified by reversed phase HPLC (acetonitrile—H₂O with 0.1% TFA as the eluent) to yield 5-chloro-1-{2-[4-(4-chloro-3-methoxy-phenyl)-piperazin-1-yl]-2-oxo-ethyl}-1,3-dihydro-benzoimidazol-2-one (10a) and 6-chloro-1-{2-[4-(4-chloro-3-methoxy-phenyl)-piperazin-1-yl]-2-oxo-ethyl}-1,3-dihydro-benzoimidazol-2-one (10b) as a 1:1 mixture:HPLC retention time, 2.29 minutes (Agilent Zorbax SB-C18, 2.1× 50 mm, 5µ, 35° C.) using 1 ml/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expected, 435.3, found, 435.4.

Example 7

Synthesis of (6-Chloro-3-{2-[4-(4-chloro-3-methoxy-phenyl)-piperazin-1-yl]-2-oxo-ethyl}-2-oxo-2,3-dihydro-benzoimidazol-1-yl)-acetic acid ethyl ester (11a) and (5-Chloro-3-{2-[4-(4-chloro-3-methoxy-phenyl)-piperazin-1-yl]-2-oxo-ethyl}-2-oxo-2,3-dihydro-benzoimidazol-1-yl)-acetic acid ethyl ester (11b)

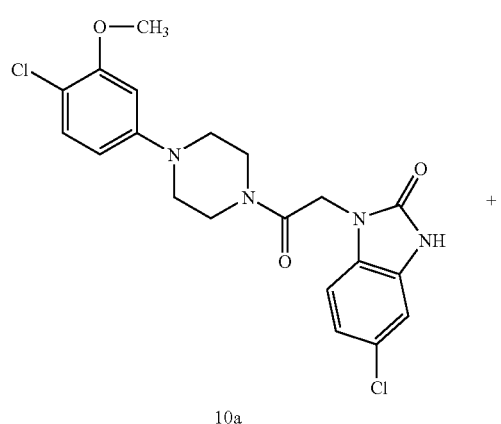

10a

+

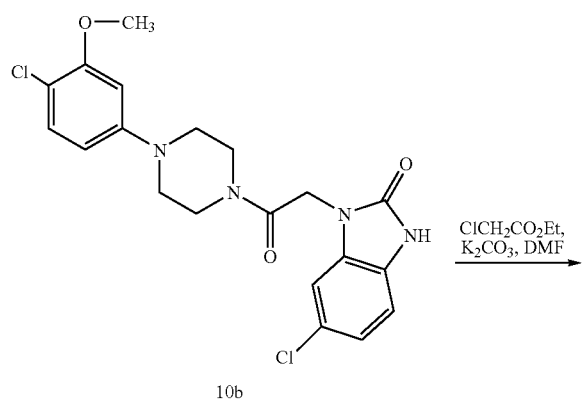

10b

ClCH₂CO₂Et, K₂CO₃, DMF

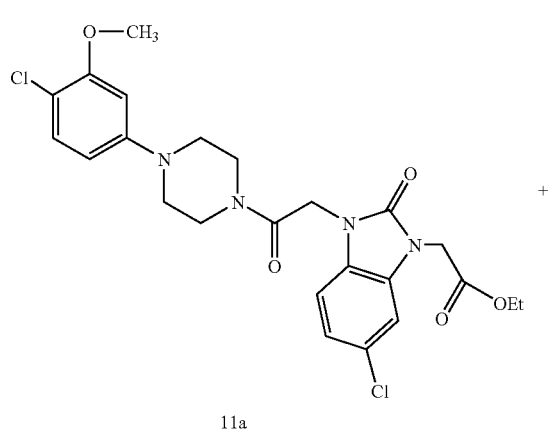

11a

+

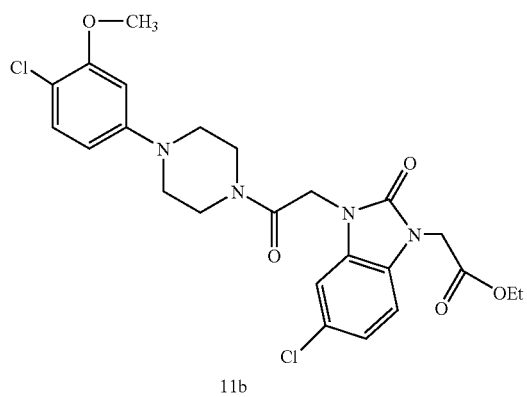

11b

Compounds 10a and 10b (87 mg) were combined with ClCH₂CO₂Et (1 equiv) and K₂CO₃ (2 equiv) in 1 mL DMF and heated at 60° C. overnight. The crude product was purified by reversed phase HPLC (acetonitrile —H₂O with 0.1% TFA as the eluent) to yield compounds 11a and 11b as a 1:1 mixture:HPLC retention time, 2.55 minutes (Agilent Zorbax SB-C18, 2.1×50 mm, 5μ, 35° C.) using 1 ml/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expected, 521.4, found, 521.4.

Example 8

Synthesis of (6-Chloro-3-{2-[4-(4-chloro-3-methoxy-phenyl)-piperazin-1-yl]-2-oxo-ethyl}-2-oxo-2,3-dihydro-benzoimidazol-1-yl)-acetic acid (12a) and (5-Chloro-3-{2-[4-(4-chloro-3-methoxy-phenyl)-piperazin-1-yl]-2-oxo-ethyl}-2-oxo-2,3-dihydrobenzoimidazol-1-yl)-acetic acid (12b).

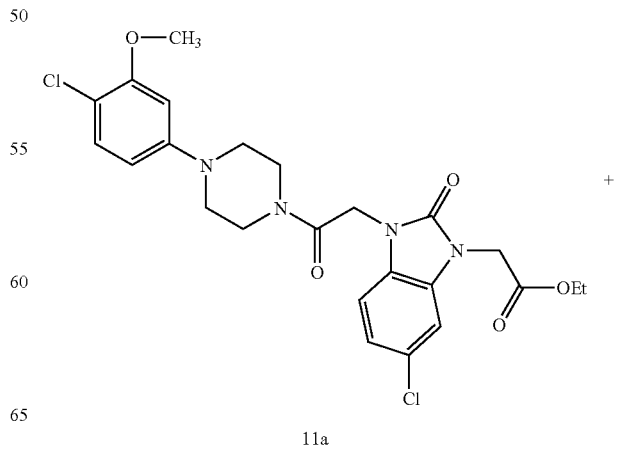

11a

63

-continued

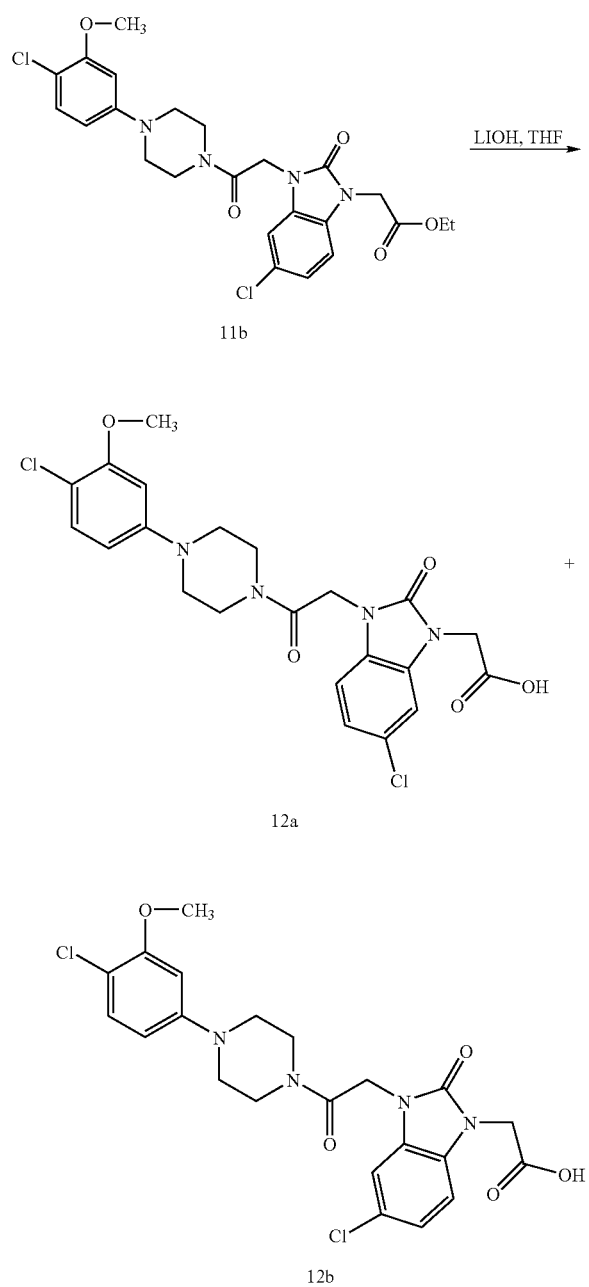

11b

12a

12b

Compounds 11a and 11b (52 mg) were stirred with 1N LiOH (2 equiv) and in 1 mL of THF at room temperature overnight. The crude product was purified by reversed phase HPLC (acetonitrile —H$_2$O with 0.1% TFA as the eluent) to yield compounds 12a and 12b as a 1:1 mixture: HPLC retention time, 2.27 minutes (Agilent Zorbax SB-C18, 2.1×50 mm, 5μ, 35° C.) using 1 ml/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expected, 493.4, found, 493.4.

64

Example 9

Synthesis of 6-chloro-3-{2-[4-(4-fluoro-benzyl)-piperazin-1-yl]-2-oxo-ethyl}-3H-benzooxazol-2-one (14)

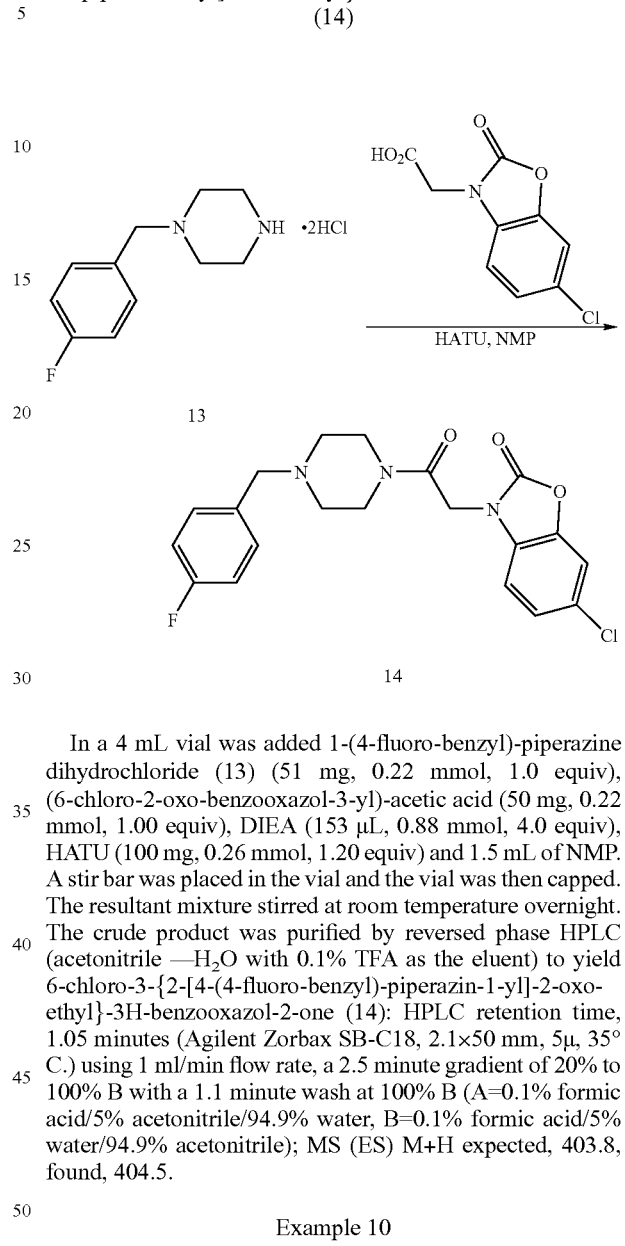

13

14

In a 4 mL vial was added 1-(4-fluoro-benzyl)-piperazine dihydrochloride (13) (51 mg, 0.22 mmol, 1.0 equiv), (6-chloro-2-oxo-benzooxazol-3-yl)-acetic acid (50 mg, 0.22 mmol, 1.00 equiv), DIEA (153 μL, 0.88 mmol, 4.0 equiv), HATU (100 mg, 0.26 mmol, 1.20 equiv) and 1.5 mL of NMP. A stir bar was placed in the vial and the vial was then capped. The resultant mixture stirred at room temperature overnight. The crude product was purified by reversed phase HPLC (acetonitrile —H$_2$O with 0.1% TFA as the eluent) to yield 6-chloro-3-{2-[4-(4-fluoro-benzyl)-piperazin-1-yl]-2-oxo-ethyl}-3H-benzooxazol-2-one (14): HPLC retention time, 1.05 minutes (Agilent Zorbax SB-C18, 2.1×50 mm, 5μ, 35° C.) using 1 ml/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expected, 403.8, found, 404.5.

Example 10

Synthesis of 3-{2-[4-(4-chloro-3-methoxy-phenyl)-piperazin-1-yl]-2-oxo-ethyl}-3H-benzooxazol-2-one (15)

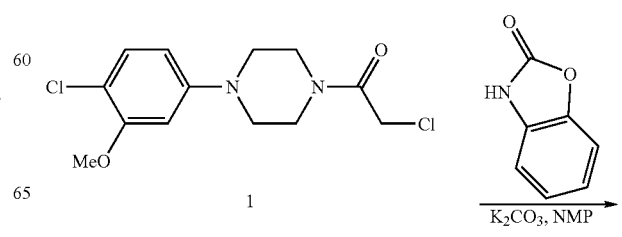

1

-continued

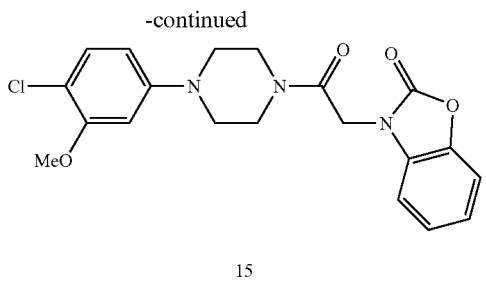

15

In a 4 mL vial was added 2-chloro-1-[4-(4-chloro-3-methoxy-phenyl)-piperazin-1-yl]-ethanone (1) (200 mg, 0.66 mmol, 1.0 equiv), 3H-benzooxazol-2-one (94 mg, 0.69 mmol, 1.05 equiv), $K_2CO_3$ (365 mg, 2.64 mmol, 4.0 equiv) and 2.5 mL of NMP. A stir bar was placed in the vial and the vial was then capped. The resultant mixture stirred at 60° C. overnight. The crude product was purified by reversed phase HPLC (acetonitrile —$H_2O$ with 0.1% TFA as the eluent) to yield 3-{2-[4-(4-chloro-3-methoxy-phenyl)-piperazin-1-yl]-2-oxo-ethyl}-3H-benzooxazol-2-one (15): HPLC retention time, 2.29 minutes (Agilent Zorbax SB-C18, 2.1×50 mm, 5μ, 35° C.) using 1 mL/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expected, 401.9, found, 402.5.

Example 11

Synthesis of 5-chloro-3-{2-[4-(4-chloro-3-methoxy-phenyl)-piperazin-1-yl]-2-oxo-ethyl}-3H-benzooxazol-2-one (16)

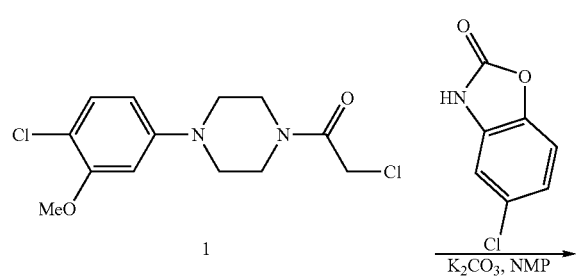

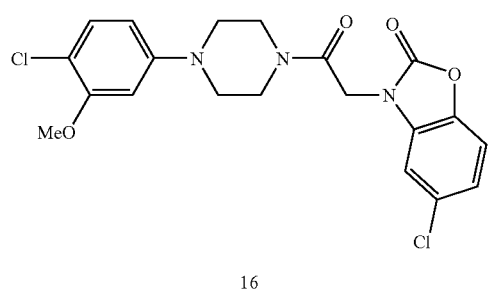

In a 4 mL vial was added 2-chloro-1-[4-(4-chloro-3-methoxy-phenyl)-piperazin-1-yl]-ethanone (1) (200 mg, 0.66 mmol, 1.0 equiv), 5-chloro-3H-benzooxazol-2-one (105 mg, 0.69 mmol, 1.05 equiv), $K_2CO_3$ (365 mg, 2.64 mmol, 4.0 equiv) and 2.5 mL of NMP. A stir bar was placed in the vial and the vial was then capped. The mixture stirred at 60° C. overnight. The crude product was purified by reversed phase HPLC (acetonitrile —$H_2O$ with 0.1% TFA as the eluent) to yield 5-chloro-3-{2-[4-(4-chloro-3-methoxy-phenyl)-piperazin-1-yl]-2-oxo-ethyl}-3H-benzooxazol-2-one (16): HPLC retention time, 2.50 minutes (Agilent Zorbax SB-C18, 2.1×50 mm, 5μ, 35° C.) using 1 mL/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expected, 436.3, found, 436.4.

Example 12

Synthesis of 6-methoxy-3-{2-[4-(4-chloro-3-methoxy-phenyl)-piperazin-1-yl]-2-oxo-ethyl}-3H-benzooxazol-2-one (17)

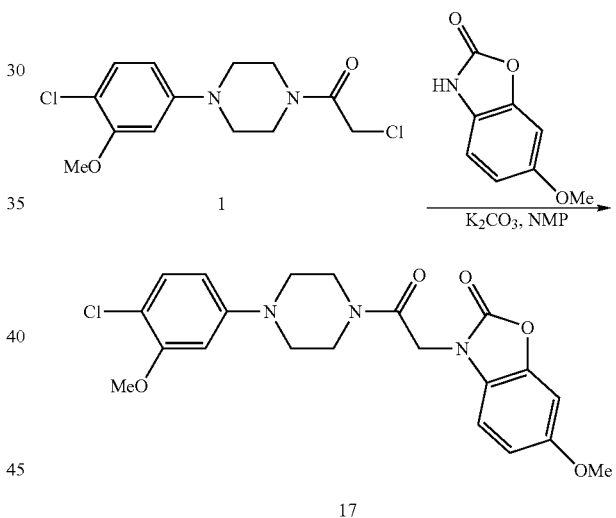

In a 4 mL vial was added 2-chloro-1-[4-(4-chloro-3-methoxy-phenyl)-piperazin-1-yl]-ethanone (1) (200 mg, 0.66 mmol, 1.0 equiv), 6-methoxy-3H-benzooxazol-2-one (114 mg, 0.69 mmol, 1.05 equiv), $K_2CO_3$ (365 mg, 2.64 mmol, 4.0 equiv) and 2.5 mL of NMP. A stir bar was placed in the vial and the vial was then capped. The resultant mixture stirred at 60° C. overnight. The crude product was purified by reversed phase HPLC (acetonitrile —$H_2O$ with 0.1% TFA as the eluent) to yield 6-methoxy-3-{2-[4-(4-chloro-3-methoxy-phenyl)-piperazin-1-yl]-2-oxo-ethyl}-3H-benzooxazol-2-one (17): HPLC retention time, 2.33 minutes (Agilent Zorbax SB-C18, 2.1×50 mm, 5μ, 35° C.) using 1 ml/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expected, 431.9, found, 431.9.

Example 13

Synthesis of 6-fluoro-3-{2-[4-(4-chloro-3-methoxy-phenyl)-piperazin-1-yl]-2-oxo-ethyl}-3H-benzooxazol-2-one (18)

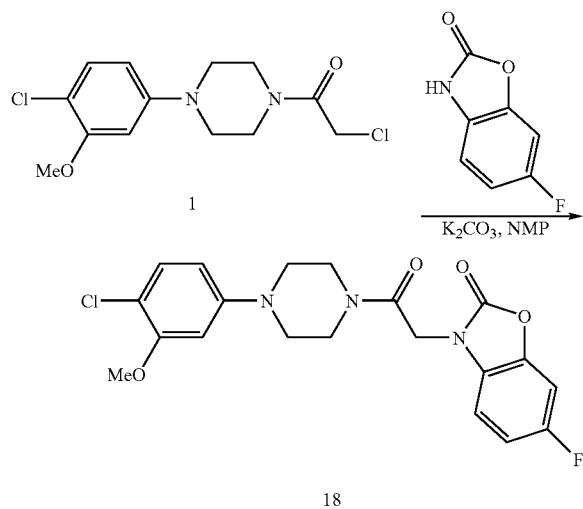

In a 4 mL vial was added 2-chloro-1-[4-(4-chloro-3-methoxy-phenyl)-piperazin-1-yl]-ethanone (1) (59 mg, 0.20 mmol, 1.0 equiv), 6-fluoro-3H-benzooxazol-2-one (30 mg, 0.20 mmol, 1.00 equiv), $K_2CO_3$ (110 mg, 0.80 mmol, 4.0 equiv) and 800 µL of NMP. A stir bar was placed in the vial and the vial was then capped. The resultant mixture stirred at 60° C. overnight. The crude product was purified by reversed phase HPLC (acetonitrile —$H_2O$ with 0.1% TFA as the eluent) to yield 6-fluoro-3-{2-[4-(4-chloro-3-methoxy-phenyl)-piperazin-1-yl]-2-oxo-ethyl}-3H-benzooxazol-2-one (18): HPLC retention time, 2.35 minutes (Agilent Zorbax SB-C18, 2.1×50 mm, 5µ, 35° C.) using 1 ml/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expected, 419.8, found, 419.9.

Example 14

Synthesis of 1-{2-[4-(4-chloro-3-methoxy-phenyl)-piperazin-1-yl]-2-oxo-ethyl}-3-methyl-1,3-dihydro-benzoimidazol-2-one (20)

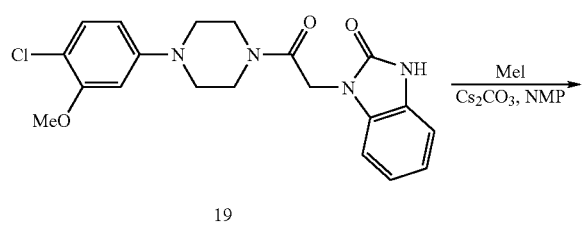

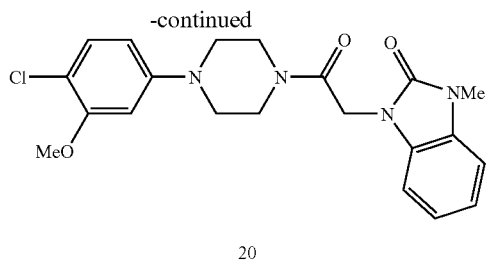

In a 4 mL vial was added 1-{2-[4-(4-chloro-3-methoxy-phenyl)-piperazin-1-yl]-2-oxo-ethyl}-1,3-dihydro-benzoimidazol-2-one (19) (10 mg, 0.025 mmol, 1.0 equiv), 5 µL of iodomethane (0.081 mmol, 3.26 equiv), 25 mg $Cs_2CO_3$ (0.075 mmol, 3.00 equiv) and 150 µL of NMP. A stir bar was placed in the vial and the vial was then capped. The resultant mixture stirred at 60° C. overnight. The crude product was purified by reversed phase HPLC (acetonitrile —$H_2O$ with 0.1% TFA as the eluent) to yield 1-{2-[4-(4-chloro-3-methoxy-phenyl)-piperazin-1-yl]-2-oxo-ethyl}-3-methyl-1,3-dihydro-benzoimidazol-2-one (20): HPLC retention time, 2.14 minutes (Agilent Zorbax SB-C18, 2.1×50 mm, 5µ, 35° C.) using 1 ml/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expected, 414.9, found, 415.5.

Example 15

Synthesis of 1-{2-[4-(4-chloro-3-methoxy-phenyl)-piperazin-1-yl]-2-oxo-ethyl}-oxazolidin-2-one (21)

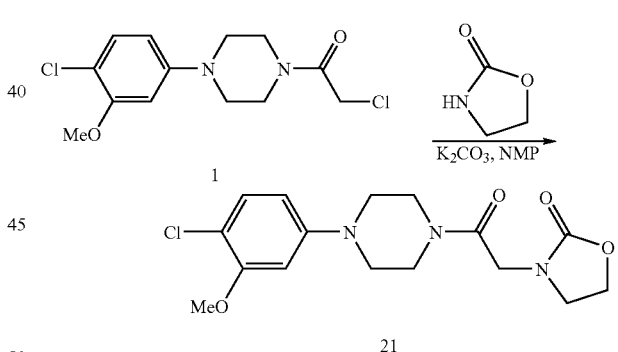

In a 4 mL vial was added 2-chloro-1-[4-(4-chloro-3-methoxy-phenyl)-piperazin-1-yl]-ethanone (1) (200 mg, 0.66 mmol, 1.0 equiv), oxazolidin-2-one (64 mg, 0.73 mmol, 1.10 equiv), $K_2CO_3$ (365 mg, 2.64 mmol, 4.0 equiv) and 2.4 mL of NMP. A stir bar was placed in the vial and the vial was then capped. The resultant mixture stirred at 60° C. overnight. The crude product was purified by reversed phase HPLC (acetonitrile —$H_2O$ with 0.1% TFA as the eluent) to yield 1-{2-[4-(4-chloro-3-methoxy-phenyl)-piperazin-1-yl]-2-oxo-ethyl}-oxazolidin-2-one (21): HPLC retention time, 1.50 minutes (Agilent Zorbax SB-C18, 2.1×50 mm, 5µ, 35° C.) using 1 ml/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expected, 353.8, found, 353.9.

Example 16

Synthesis of 1-{2-[4-(4-chloro-3-methoxy-phenyl)-piperazin-1-yl]-2-oxo-ethyl}-imidazolidin-2-one (22)

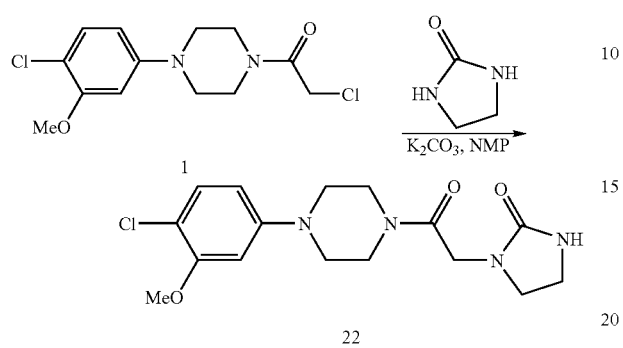

In a 4 mL vial was added 2-chloro-1-[4-(4-chloro-3-methoxy-phenyl)-piperazin-1-yl]-ethanone (1) (200 mg, 0.66 mmol, 1.0 equiv), imidazolidin-2-one (64 mg, 0.73 mmol, 1.10 equiv), $K_2CO_3$ (365 mg, 2.64 mmol, 4.0 equiv) and 2.4 mL of NMP. A stir bar was placed in the vial and the vial was then capped. The mixture stirred at 60° C. overnight. The crude product was purified by reversed phase HPLC (acetonitrile —$H_2O$ with 0.1% TFA as the eluent) to yield 1-{2-[4-(4-chloro-3-methoxy-phenyl)-piperazin-1-yl]-2-oxo-ethyl}-imidazolidin-2-one (22): HPLC retention time, 1.33 minutes (Agilent Zorbax SB-C18, 2.1×50 mm, 5µ, 35° C.) using 1 ml/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expected, 352.8, found, 353.5.

Example 17

Synthesis of 1-[4-(4-chloro-3-methoxy-phenyl)-piperazin-1-yl]-2-((2S,6R)-2,6-dimethyl-piperidin-1-yl)-ethanone (23)

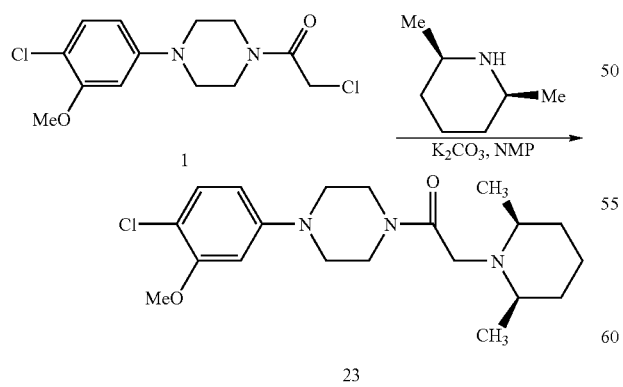

In a 4 mL vial was added 2-chloro-1-[4-(4-chloro-3-methoxy-phenyl)-piperazin-1-yl]-ethanone (1) (200 mg, 0.66 mmol, 1.0 equiv), (2S,6R)-2,6-dimethyl-piperidine (100 µL, 0.72 mmol, 1.10 equiv), $K_2CO_3$ (365 mg, 2.64 mmol, 4.0 equiv) and 2.4 mL of NMP. A stir bar was placed in the vial and the vial was then capped. The resultant mixture stirred at 60° C. overnight. The crude product was purified by reversed phase HPLC (acetonitrile —$H_2O$ with 0.1% TFA as the eluent) to yield 1-[4-(4-chloro-3-methoxy-phenyl)-piperazin-1-yl]-2-((2S,6R)-2,6-dimethyl-piperidin-1-yl)-ethanone (23): HPLC retention time=1.31 minutes (Agilent Zorbax SB-C18, 2.1×50 mm, 5µ, 35° C.) using 1 ml/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expected, 379.9, found, 380.0.

Example 18

Synthesis of 1-[4-(4-chloro-3-methoxy-phenyl)-piperazin-1-yl]-2-morpholin-4-yl-ethanone (24)

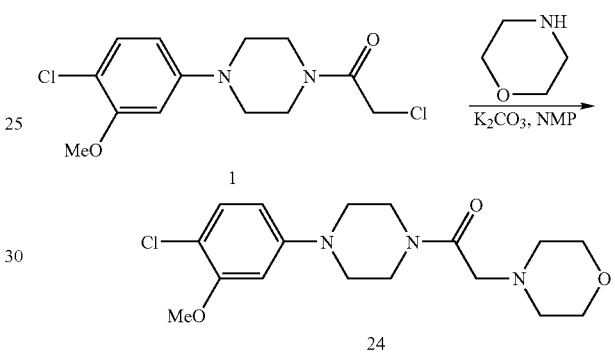

In a 4 mL vial was added 2-chloro-1-[4-(4-chloro-3-methoxy-phenyl)-piperazin-1-yl]-ethanone (1) (200 mg, 0.66 mmol, 1.0 equiv), and morpholine (575 µL, 6.60 mmol, 10.00 equiv). A stir bar was placed in the vial and the vial was then capped. The resultant mixture stirred at 60° C. overnight. The crude product was purified by reversed phase HPLC (acetonitrile —$H_2O$ with 0.1% TFA as the eluent) to yield 1-[4-(4-chloro-3-methoxy-phenyl)-piperazin-1-yl]-2-morpholin-4-yl-ethanone (24): HPLC retention time, 0.32 minutes (Agilent Zorbax SB-C18, 2.1×50 mm, 5µ, 35° C.) using 1 ml/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expected, 353.9, found, 354.5.

Example 19

Synthesis of 1-[4-(4-chloro-3-methoxy-phenyl)-piperazin-1-yl]-2-(4-methyl-piperazin-1-yl)-ethanone (25)

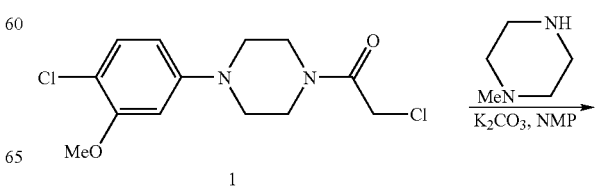

-continued

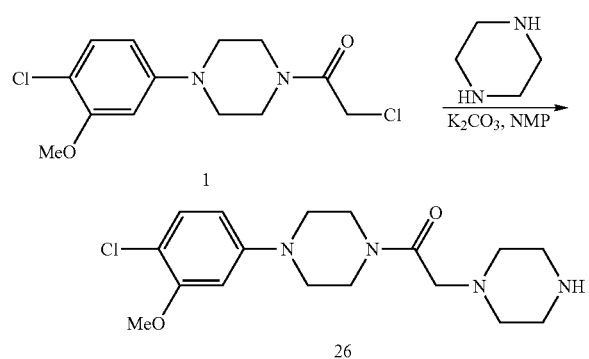

25

In a 4 mL vial was added 2-chloro-1-[4-(4-chloro-3-methoxy-phenyl)-piperazin-1-yl]-ethanone (1) (200 mg, 0.66 mmol, 1.0 equiv) and 1-methylpiperazine (725 µL, 6.60 mmol, 10.00 equiv). A stir bar was placed in the vial and the vial was then capped. The resultant mixture stirred at 60° C. overnight. The crude product was purified by reversed phase HPLC (acetonitrile —H₂O with 0.1% TFA as the eluent) to yield 1-[4-(4-chloro-3-methoxy-phenyl)-piperazin-1-yl]-2-(4-methyl-piperazin-1-yl)-ethanone (25): HPLC retention time, 0.32 minutes (Agilent Zorbax SB-C18, 2.1×50 mm, 5µ, 35°C.) using 1 ml/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expected, 367.5, found, 367.9.

Example 20

Synthesis of 1-[4-(4-chloro-3-methoxy-phenyl)-piperazin-1-yl]-2-piperazin-1-yl-ethanone (26)

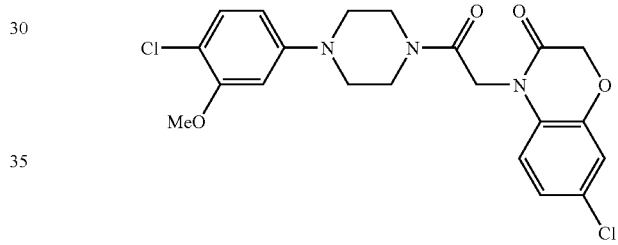

In a 4 mL vial was added 2-chloro-1-[4-(4-chloro-3-methoxy-phenyl)-piperazin-1-yl]-ethanone (1) (200 mg, 0.66 mmol, 1.0 equiv), piperazine (413 mg, 6.60 mmol, 10.00 equiv), and 2.4 mL of NMP. A stir bar was placed in the vial and the vial was then capped. The resultant mixture stirred at 60° C. overnight. The crude product was purified by reversed phase HPLC (acetonitrile —H₂O with 0.1% TFA as the eluent) to yield 1-[4-(4-chloro-3-methoxy-phenyl)-piperazin-1-yl]-2-piperazin-1-yl-ethanone (26): HPLC retention time, 0.30 minutes (Agilent Zorbax SB-C18, 2.1×50 mm, 5µ, 35° C.) using 1 ml/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expected, 352.9, found, 353.5.

Example 21

Synthesis of 7-Chloro-4-{2-[4-(4-chloro-3-methoxy-phenyl)-piperazin-1-yl]-2-oxo-ethyl}-4H-benzo[1,4]oxazin-3-one (29)

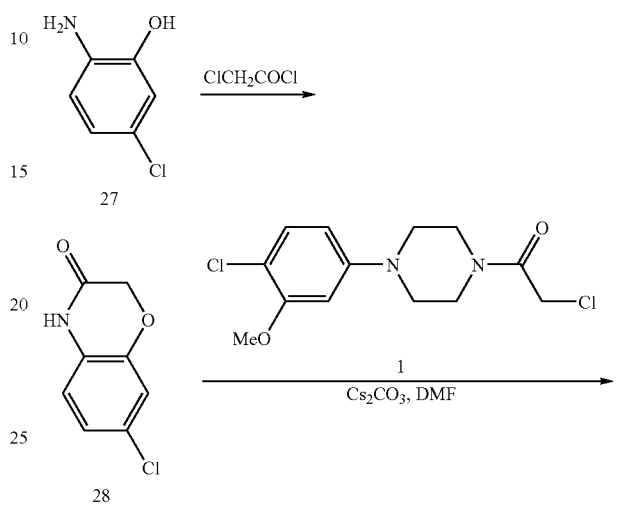

7-Chloro-4H-benzo[1,4]oxazin-3-one (28): A mixture of 2-amino-5-chloro-phenol (27) (2.0 g, 14 mmol, 1 equiv) in 30 ml of THF, chloroacetyl chloride (1.26 ml, 16.8 mmol, 1.2 equiv), and saturated aqueous NaHCO₃ 50 mL was stirred at RT for 2 hrs and then heated at 80° C. overnight. The reaction mixture was diluted with EtOAc, and washed with water. Purification of the crude product by flash chromatography provided 7-chloro-4H-benzo[1,4]oxazin-3-one (28): LCMS Retention time: 1.48 min.; LCMS observed (M+H)⁺: 184.

7-Chloro-4-{2-[4-(4-chloro-3-methoxy-phenyl)-piperazin-1-yl]-2-oxo-ethyl}-4H-benzo[1,4]oxazin-3-one (29): A mixture of 2-chloro-1-[4-(4-chloro-3-methoxy-phenyl)-piperazin-1-yl]-ethanone (1) (331 mg, 1.1 mmol, 1 equiv) in 5 ml of DMF, 4H-Benzo[1,4]oxazin-3-one (28) (200 mg, 1.1 mmol, 1.0 equiv) and cesium carbonate (710 mg, 2.2 mmol, 2 equiv) was stirred at RT overnight. The reaction solution was diluted with EtOAc, and the organic solution was washed with water. Purification of the crude reaction mixture using flash chromatography provided 7-chloro-4-{2-[4-(4-chloro-3-methoxy-phenyl)-piperazin-1-yl]-2-oxo-ethyl}-4H-benzo[1,4]oxazin-3-one (29): LCMS Retention time, 2.58 min.; LCMS observed (M+H)⁺: 450.

Example 22

Synthesis of 6-Chloro-4-{2-[4-(4-chloro-3-methoxy-phenyl)-piperazin-1-yl]-2-oxo-ethyl}-4H-benzo[1,4]oxazin-3-one (32)

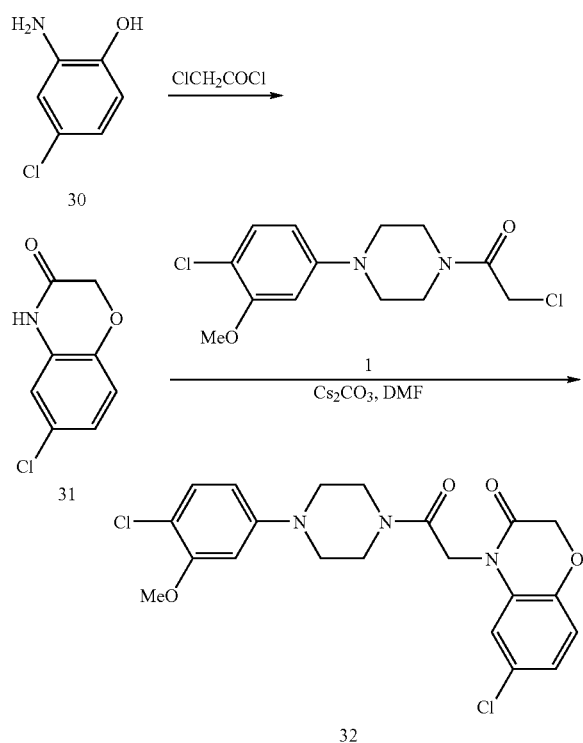

6-Chloro-4H-benzo[1,4]oxazin-3-one (31): 6-Chloro-4H-benzo[1,4]oxazin-3-one was synthesized by the same procedure used in the synthesis of 7-Chloro-4H-benzo[1,4]oxazin-3-one (28): LCMS Retention time, 1.38 min; LCMS observed (M+H)$^+$, 184.

6-Chloro-4-{2-[4-(4-chloro-3-methoxy-phenyl)-piperazin-1-yl]-2-oxo-ethyl}-4H-benzo[1,4]oxazin-3-one (32): 6-Chloro-4-{2-[4-(4-chloro-3-methoxy-phenyl)-piperazin-1-yl]-2-oxo-ethyl}-4H-benzo[1,4]oxazin-3-one (32) was synthesized by the same procedure used in the synthesis of Compound 29: LCMS Retention time, 2.59 min; LCMS observed (M+H)$^+$, 450.

Example 23

Synthesis of 4-{2-[4-(4-Chloro-3-methoxy-phenyl)-piperazin-1-yl]-2-oxo-ethyl}-4H-benzo[1,4]oxazin-3-one (33)

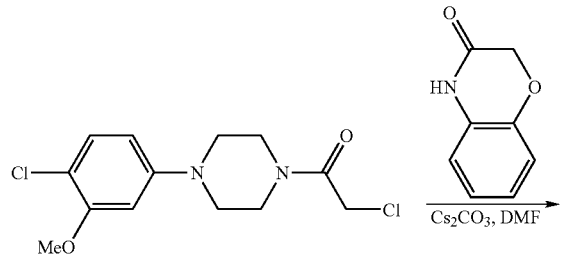

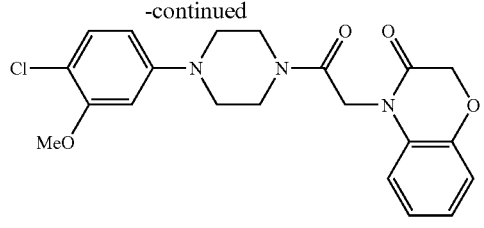

4-{2-[4-(4-Chloro-3-methoxy-phenyl)-piperazin-1-yl]-2-oxo-ethyl}-4H-benzo[1,4]oxazin-3-one (33) was synthesized by the same procedure used in the synthesis of Compound 29. LCMS Retention time, 2.35 min; LCMS observed (M+H)$^+$, 416.

Example 24

Synthesis of 4-{2-[4-(4-Chloro-3-methoxy-phenyl)-piperazin-1-yl]-2-oxo-ethyl}-4H-oxazolo[4,5-b]pyridin-2-one (34)

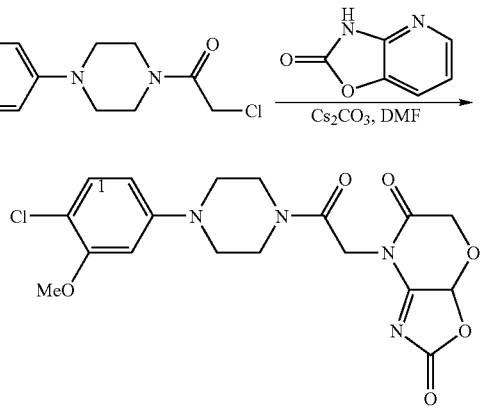

4-{2-[4-(4-Chloro-3-methoxy-phenyl)-piperazin-1-yl]-2-oxo-ethyl}-4H-oxazolo[4,5-b]pyridin-2-one (34) was synthesized by the same procedure used in the synthesis of Compound 29: LCMS Retention time, 1.62 min; LCMS observed (M+H)$^+$, 403.

Example 25

Synthesis of 4-{2-[4-(4-Chloro-2-fluoro-5-methoxy-phenyl)-piperazin-1-yl]-2-oxo-ethyl}-4H-oxazolo[4,5-b]pyridin-2-one (35a) and 3-{2-[4-(4-Chloro-2-fluoro-5-methoxy-phenyl)-piperazin-1-yl]-2-oxo-ethyl}-3H-oxazolo[4,5-b]pyridin-2-one (35b)

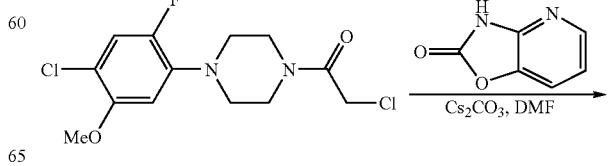

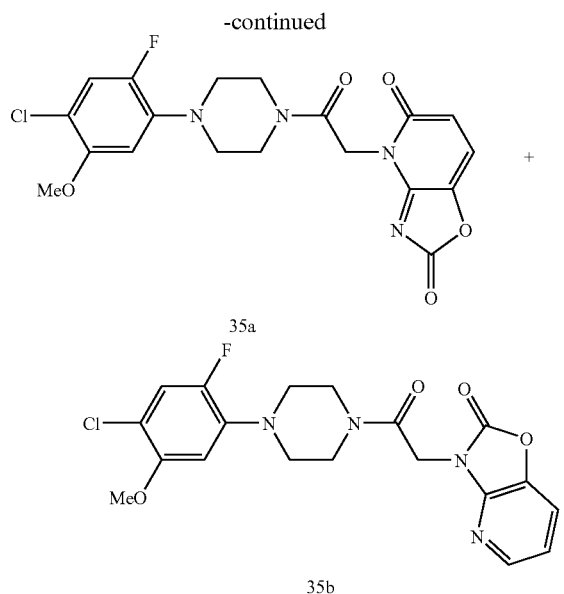

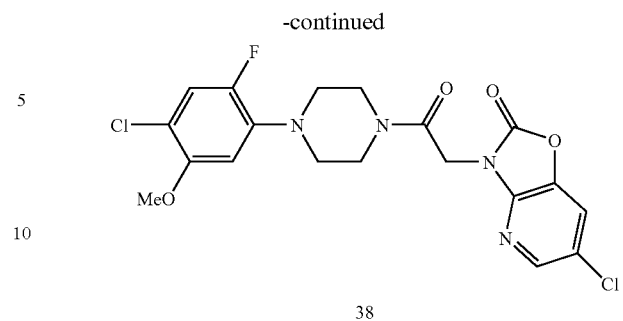

6-Chloro-3H-oxazolo[4,5-b]pyridin-2-one (37): A mixture of 3H-oxazolo[4,5-b]pyridin-2-one (36) (300 mg, 2.2 mmol, 1 equiv) and NCS (352 mg, 2.65 mmol, 1.2 equiv) in 5 mL of acetonitrile was heated at 85° C. overnight. The reaction solution was diluted with ethyl acetate (EtOAc), and washed with water. The organic solution was concentrated and purified by flash chromatography, to provide 6-Chloro-3H-oxazolo[4,5-b]pyridin-2-one (37): LCMS Retention time, 0.69 min; LCMS observed (M+H)$^+$: 171.

6-Chloro-3-{2-[4-(4-chloro-2-fluoro-5-methoxy-phenyl)-piperazin-1-yl]-2-oxo-ethyl}-3H-oxazolo[4,5-b]pyridin-2-one (38): 6-Chloro-3-{2-[4-(4-chloro-2-fluoro-5-methoxy-phenyl)-piperazin-1-yl]-2-oxo-ethyl}-3H-oxazolo[4,5-b]pyridin-2-one (38) was synthesized by the same procedure used in the synthesis of Compound 29: LCMS Retention time, 2.74 min; LCMS observed for (M+H)$^+$: 455.

Compounds 35a and 35b were synthesized according to the procedure outlined for the synthesis of Compound 29.

4-{2-[4-(4-Chloro-2-fluoro-5-methoxy-phenyl)-piperazin-1-yl]-2-oxo-ethyl}-4H-oxazolo[4,5-b]pyridin-2-one (35a): LCMS Retention time, 1.83 min.; LCMS observed for (M+H)$^+$, 421.

3-{2-[4-(4-Chloro-2-fluoro-5-methoxy-phenyl)-piperazin-1-yl]-2-oxo-ethyl}-3H-oxazolo[4,5-b]pyridin-2-one (35b): LCMS Retention time, 2.33 min.; LCMS observed (M+H)$^+$: 421.

Example 26

Synthesis 6-Chloro-3-{2-[4-(4-chloro-2-fluoro-5-methoxy-phenyl)-piperazin-1-yl]-2-oxo-ethyl}-3H-oxazolo[4,5-b]pyridin-2-one (38)

Example 27

Synthesis of 7-Chloro-4-{2-[4-(4-chloro-2-fluoro-5-methoxy-phenyl)-piperazin-1-yl]-2-oxo-ethyl}-4H-pyrido[3,2-b][1,4]oxazin-3-one (41)

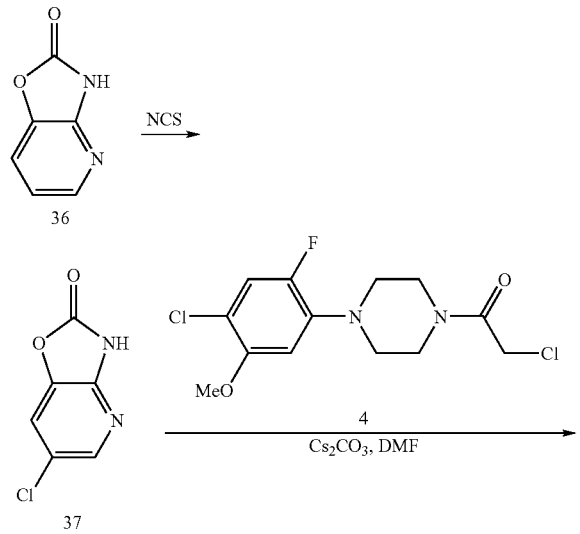

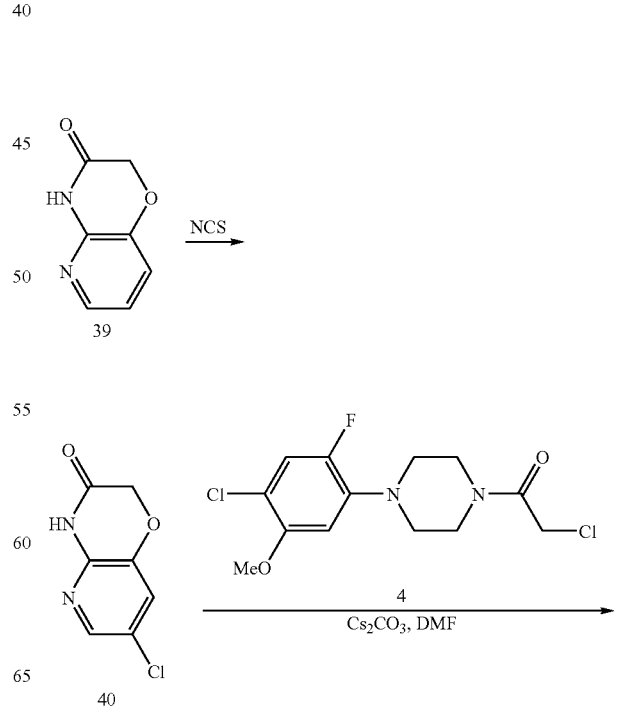

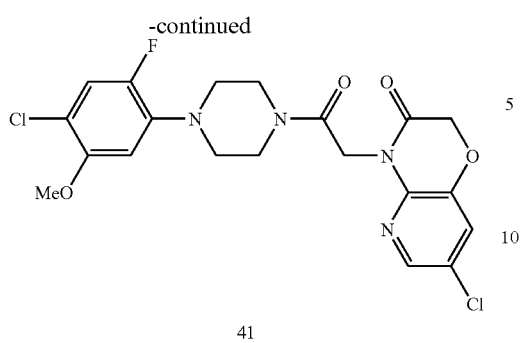

41

7-Chloro-4H-pyrido[3,2-b][1,4]oxazin-3-one (40): 7-Chloro-4H-pyrido[3,2-b][1,4]oxazin-3-one (40) was synthesized by the same procedure used in the synthesis of Compound 37: LCMS Retention time, 0.60 min.; LCMS observed (M+H)+: 185.

7-Chloro-4-{2-[4-(4-chloro-2-fluoro-5-methoxy-phenyl)-piperazin-1-yl]-2-oxo-ethyl}-4H-pyrido[3,2-b][1,4]oxazin-3-one (41): Compound 41 was synthesized by the same procedure used in the synthesis of Compound 32: LCMS Retention time, 2.64 min.; LCMS observed (M+H)+: 469.

Example 28

Synthesis of 3-{2-[4-(4-Chloro-3-methoxy-phenyl)-piperazin-1-yl]-2-oxo-ethyl}-4-phenyl-oxazolidin-2-one (42)

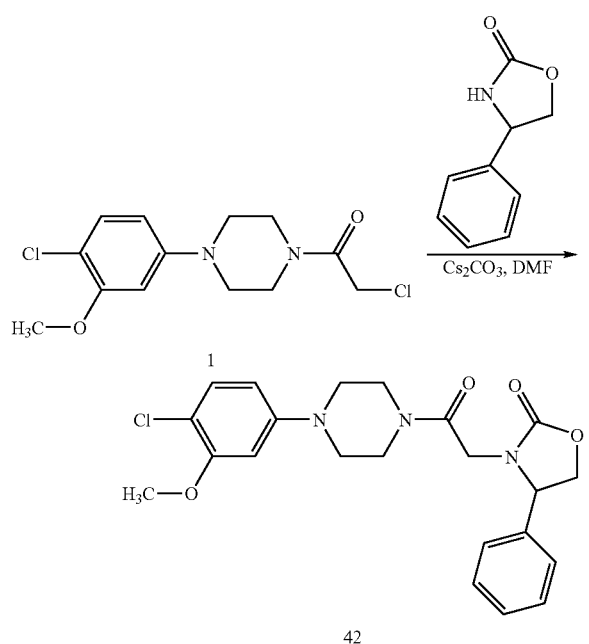

Compound 42 was prepared according to the procedure described in Example 2 using 2-Chloro-1-[4-(4-chloro-3-methoxy-phenyl)-piperazin-1-yl]-ethanone (1) (0.1 mmol), 4-phenyl-oxazolidin-2-one and Cs2CO3 in DMF: HPLC retention time, 2.30 minutes (Agilent Zorbax SB-C18, 2.1× 50 mm, 5μ, 35° C.) using 1 ml/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expected, 430.2, found, 430.3.

Example 29

Synthesis of 3-{2-[4-(4-Chloro-3-methoxy-phenyl)-piperazin-1-yl]-2-oxo-ethyl}-5-phenyl-oxazolidin-2-one (43)

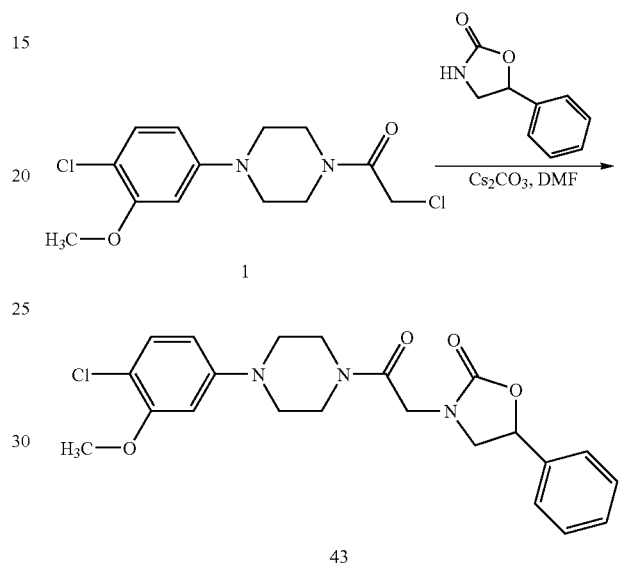

Compound 43 was prepared according to the procedure described Example 2 using 2-Chloro-1-[4-(4-chloro-3-methoxy-phenyl)-piperazin-1-yl]-ethanone (1) (0.1 mmol), 3-phenyl-oxazolidin-2-one and Cs2CO3 in DMF: HPLC retention time, 2.32 minutes (Agilent Zorbax SB-C18, 2.1× 50 mm, 5μ, 35° C.) using 1 ml/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expected, 430.2, found, 430.2.

Example 30

Synthesis of (3-{2-[4-(4-Chloro-3-methoxy-phenyl)-piperazin-1-yl]-2-oxo-ethyl}-2-oxo-2,3-dihydro-benzooxazol-6-yloxy)-acetic acid (46)

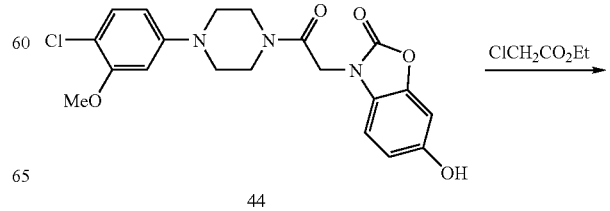

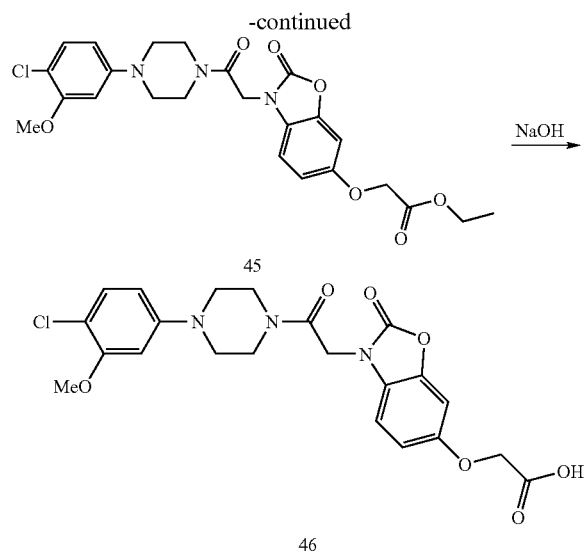

(3-{2-[4-(4-Chloro-3-methoxy-phenyl)-piperazin-1-yl]-2-oxo-ethyl}-2-oxo-2,3-dihydro-benzooxazol-6-yloxy)-acetic acid ethyl ester (45): A mixture of 3-{2-[4-(4-chloro-3-methoxy-phenyl)-piperazin-1-yl]-2-oxo-ethyl}-6-hydroxy-3H-benzooxazol-2-one (44) (300 mg, 0.72 mmol, 1 eq), ethyl chloroacetate (132 mg, 1.08 mmol, 1.5 eq), cesium carbonate (467 mg, 1.43 mmol, 2 eq) in DMF (2 ml) was stirred at rt overnight. The reaction mixture was diluted with ethyl acetate, washed with water, and purified by flash chromatography to provide (3-{2-[4-(4-chloro-3-methoxy-phenyl)-piperazin-1-yl]-2-oxo-ethyl}-2-oxo-2,3-dihydro-benzooxazol-6-yloxy)-acetic acid ethyl ester (45).

(3-{2-[4-(4-Chloro-3-methoxy-phenyl)-piperazin-1-yl]-2-oxo-ethyl}-2-oxo-2,3-dihydro-benzooxazol-6-yloxy)-acetic acid (46): A mixture of (3-{2-[4-(4-chloro-3-methoxy-phenyl)-piperazin-1-yl]-2-oxo-ethyl}-2-oxo-2,3-dihydro-benzooxazol-6-yloxy)-acetic acid ethyl ester (45) in THF (3 ml) and NaOH (2N, 3 ml) was stirred at rt for 2 hours. The reaction mixture was neutralized with HCl (1 N), extracted with ethyl acetate, washed with water, and purified by flash chromatography to provide (3-{2-[4-(4-chloro-3-methoxy-phenyl)-piperazin-1-yl]-2-oxo-ethyl}-2-oxo-2,3-dihydro-benzooxazol-6-yloxy)-acetic acid (46): LCMS observed for $(M+H)^+$: 476.5

Example 31

Synthesis of 3-{2-[4-(4-Chloro-3-methoxy-phenyl)-piperazin-1-yl]-2-oxo-ethyl}-6-[1,2,4]oxadiazol-3-yl-3H-benzooxazol-2-one (51)

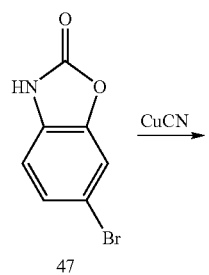

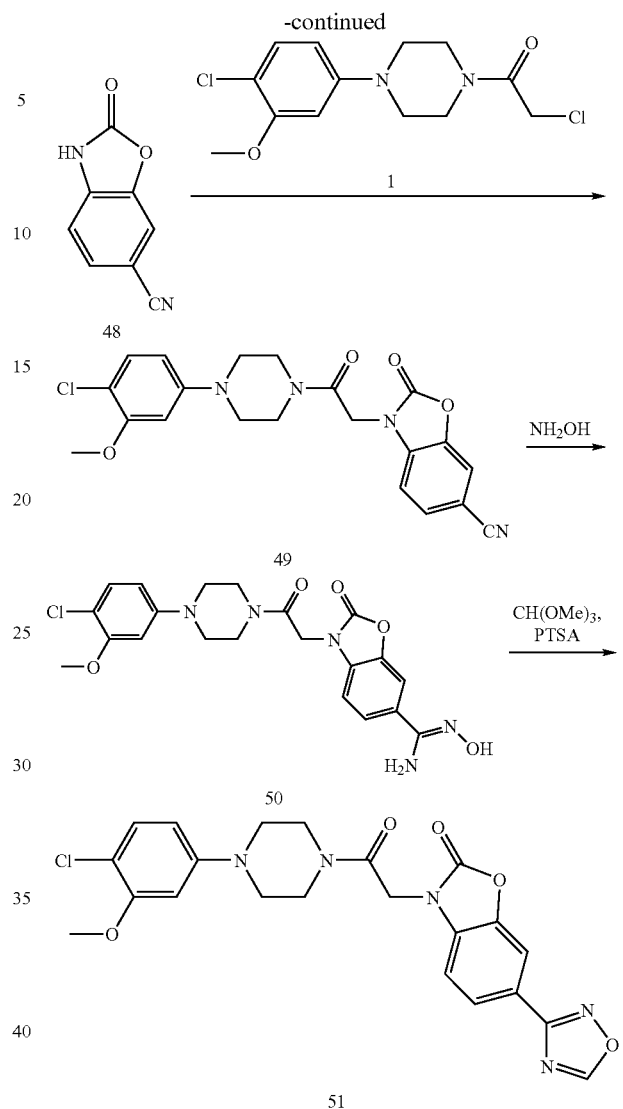

2-Oxo-2,3-dihydro-benzooxazole-6-carbonitrile (48): A mixture of 6-bromo-3H-benzooxazol-2-one (47) (400 mg, 1.87 mmol, 1 eq), copper cyanide (3.3 g, 37 mmol, 20 eq), in DMF (10 ml) was stirred at 175° C. for 3 hours. The reaction mixture was diluted with ethyl acetate, filtered to remove the precipitated solid material, and the organic phase was washed with water, purified by flash chromatography to give 2-oxo-2,3-dihydro-benzooxazole-6-carbonitrile (48).

3-{2-[4-(4-Chloro-3-methoxy-phenyl)-piperazin-1-yl]-2-oxo-ethyl}-2-oxo-2,3-dihydro-benzooxazole-6-carbonitrile (49): A mixture of 2-chloro-1-[4-(4-chloro-3-methoxy-phenyl)-piperazin-1-yl]-ethanone (1) (190 mg, 0.625 mmol, 1 eq), 2-oxo-2,3-dihydro-benzooxazole-6-carbonitrile (48) (100 mg, 0.625 mmol, 1 eq), cesium carbonate (400 mg, 1.23 mmol, 2 eq) in DMF (2 ml) was stirred at rt overnight. The reaction mixture was diluted with ethyl acetate, washed with water and purified with flash chromatography to give 3-{2-[4-(4-chloro-3-methoxy-phenyl)-piperazin-1-yl]-2-oxo-ethyl}-2-oxo-2,3-dihydro-benzooxazole-6-carbonitrile (49).

3-{2-[4-(4-Chloro-3-methoxy-phenyl)-piperazin-1-yl]-2-oxo-ethyl}-N-hydroxy-2-oxo-2,3-dihydro-benzooxazole-6-carboxamidine (50): A mixture of 3-{2-[4-(4-chloro-3-methoxy-phenyl)-piperazin-1-yl]-2-oxo-ethyl}-2-oxo-2,3-dihydro-benzooxazole-6-carbonitrile (49) (150 mg, 0.35 mmol, 1 eq), NH₂OH.HCl (73 mg, 1.05 mmol, 3 eq), TEA (270 ml), in ethanol (2 ml) was stirred at 60° C. overnight. The resultant mixture was cooled and precipitated material was removed by filtration. The reaction solution was washed with ethyl acetate to provide 3-{2-[4-(4-chloro-3-methoxy-phenyl)-piperazin-1-yl]-2-oxo-ethyl}-N-hydroxy-2-oxo-2,3-dihydro-benzooxazole-6-carboxamidine (50).

3-{2-[4-(4-Chloro-3-methoxy-phenyl)-piperazin-1-yl]-2-oxo-ethyl}-6-[1,2,4]oxadiazol-3-yl-3H-benzooxazol-2-one (51): A mixture 3-{2-[4-(4-chloro-3-methoxy-phenyl)-piperazin-1-yl]-2-oxo-ethyl}-N-hydroxy-2-oxo-2,3-dihydro-benzooxazole-6-carboxamidine (65 mg), trimethyl orthoformate (3 ml) and p-toluenesulfonic acid (PTSA) (23 mg) was stirred at 103° C. overnight. The resultant solution was evaporated to dryness and then purified by flash chromatography to provide 3-{2-[4-(4-chloro-3-methoxy-phenyl)-piperazin-1-yl]-2-oxo-ethyl}-6-[1,2,4]oxadiazol-3-yl-3H-benzooxazol-2-one (51): LCMS observed for (M+H)⁺: 470.5.

Example 32

Synthesis of 3-{2-[4-(4-Chloro-3-methoxy-phenyl)-piperazin-1-yl]-2-oxo-ethyl}-6-(2-hydroxy-ethoxy)-3H-benzooxazol-2-one (56)

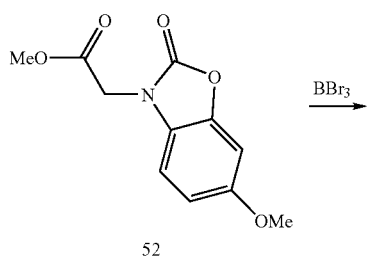

52

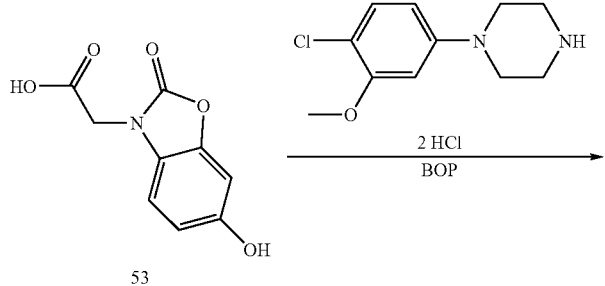

53

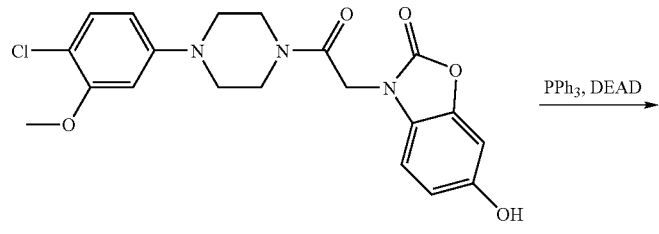

54

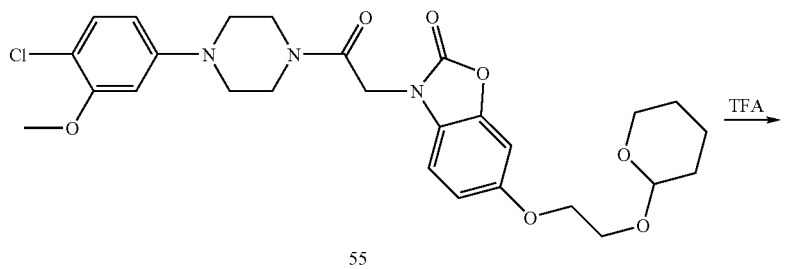

55

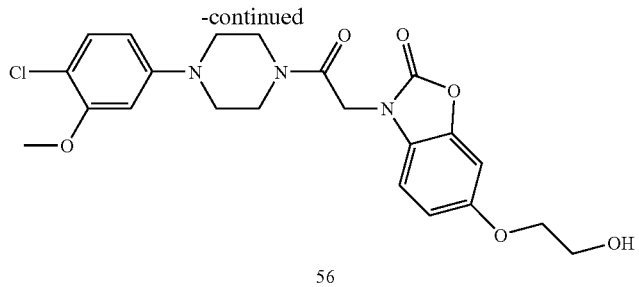

56

(6-Hydroxy-2-oxo-benzooxazol-3-yl)-acetic acid (53): To a solution of (6-methoxy-2-oxo-benzooxazol-3-yl)-acetic acid ethyl ester (52) (251 mg, 1 mmol, 1 equiv) in 3 mL of DCM was added BBr$_3$ (0.3 mL, 3 equiv) and the reaction solution was stirred for 1 h. The reaction mixture was quenched by slow addition of water, followed by the addition of EtOAc. The organic layer was isolated and dried over sodium sulfate, filtered, evaporated in vacuo to provide (6-hydroxy-2-oxo-benzooxazol-3-yl)-acetic acid (53).

3-{2-[4-(4-Chloro-3-methoxy-phenyl)-piperazin-1-yl]-2-oxo-ethyl}-6-hydroxy-3H-benzooxazol-2-one (54): A mixture of (6-hydroxy-2-oxo-benzooxazol-3-yl)-acetic acid (53) (800 mg, 1 equiv), 1-(4-chloro-3-methoxy-phenyl)-piperazine dihydrochloride (1.16 g, 1 equiv), BOP (1.7 g, 1 equiv), triethylamine (5 mL, 5 equiv) in 10 ml of DMF was stirred at room temperature for overnight. The resultant solution was then diluted with EtOAc (50 mL) and washed with water. The organic layer was dried over sodium sulfate and concentrated in vacuo to provide a crude residue which was purified by flash chromatography to provide 3-{2-[4-(4-chloro-3-methoxy-phenyl)-piperazin-1-yl]-2-oxo-ethyl}-6-hydroxy-3H-benzooxazol-2-one (54).

3-{2-[4-(4-Chloro-3-methoxy-phenyl)-piperazin-1-yl]-2-oxo-ethyl}-6-[2-(tetrahydro-pyran-2-yloxy)-ethoxy]-3H-benzooxazol-2-one (55): To a mixture of PPh$_3$ (70 mg, 0.27 mmol, 1.1 eq), and DEAD (40 mg, 0.23 mmol, 1 eq) in THF (0.5 ml), was added 3-{2-[4-(4-chloro-3-methoxy-phenyl)-piperazin-1-yl]-2-oxo-ethyl}-6-hydroxy-3H-benzooxazol-2-one (54) (100 mg, 0.24 mmol, 1 eq) in THF (1 ml). The reaction mixture immediately turned clear and was heated to 85° C. 2-(Tetrahydro-pyran-2-yloxy)-ethanol (38.5 mg, 0.27 mmol, 1.1 eq), was then added to the reaction solution, and stirred for 3 hours at rt. The isolated crude product was purified with HPLC to provide 3-{2-[4-(4-chloro-3-methoxy-phenyl)-piperazin-1-yl]-2-oxo-ethyl}-6-[2-(tetrahydro-pyran-2-yloxy)-ethoxy]-3H-benzooxazol-2-one (55).

3-{2-[4-(4-Chloro-3-methoxy-phenyl)-piperazin-1-yl]-2-oxo-ethyl}-6-(2-hydroxy-ethoxy)-3H-benzooxazol-2-one (56): To a solution of 3-{2-[4-(4-chloro-3-methoxy-phenyl)-piperazin-1-yl]-2-oxo-ethyl}-6-[2-(tetrahydro-pyran-2-yloxy)-ethoxy]-3H-benzooxazol-2-one (55) (50 mg) in THF was added 1 mL of TFA and the resultant solution was stirred for 1 hour. The reaction mixture was purified by HPLC to provide 3-{2-[4-(4-chloro-3-methoxy-phenyl)-piperazin-1-yl]-2-oxo-ethyl}-6-(2-hydroxy-ethoxy)-3H-benzooxazol-2-one (56): LCMS observed for (M+H)$^+$: 462.5.

Example 33

Synthesis of 6-(2-Amino-ethoxy)-3-{2-[4-(4-chloro-3-methoxy-phenyl)-piperazin-1-yl]-2-oxo-ethyl}-3H-benzooxazol-2-one (58)

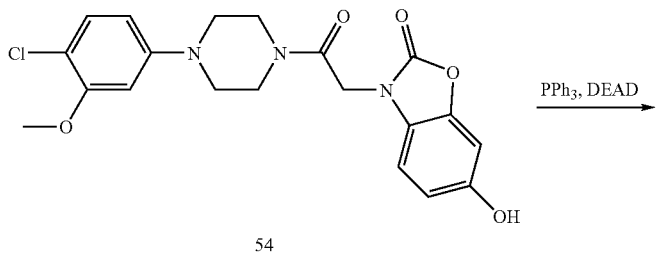

54

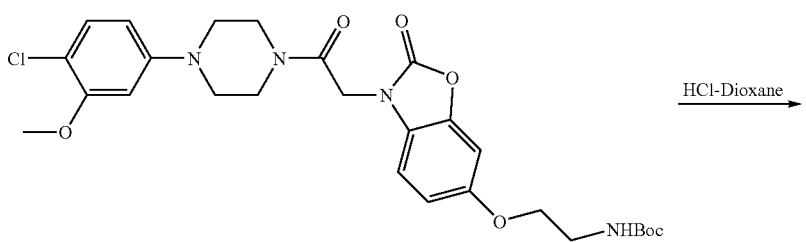

57

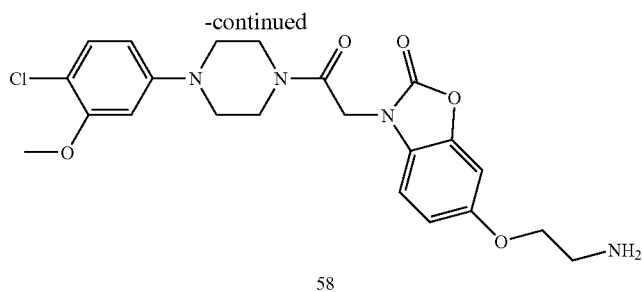

58

[2-(3-{2-[4-(4-Chloro-3-methoxy-phenyl)-piperazin-1-yl]-2-oxo-ethyl}-2-oxo-2,3-dihydro-benzooxazol-6-yloxy)-ethyl]-carbamic acid tert-butyl ester (57): [2-(3-{2-[4-(4-chloro-3-methoxy-phenyl)-piperazin-1-yl]-2-oxo-ethyl}-2-oxo-2,3-dihydro-benzooxazol-6-yloxy)-ethyl]-carbamic acid tert-butyl ester (57) was prepared by the analogous procedure as described in Example 32 using (2-hydroxy-ethyl)-carbamic acid tert-butyl ester.

6-(2-Amino-ethoxy)-3-{2-[4-(4-chloro-3-methoxy-phenyl)-piperazin-1-yl]-2-oxo-ethyl}-3H-benzooxazol-2-one (58): [2-(3-{2-[4-(4-chloro-3-methoxy-phenyl)-piperazin-1-yl]-2-oxo-ethyl}-2-oxo-2,3-dihydro-benzooxazol-6-yloxy)-ethyl]-carbamic acid tert-butyl ester (58) (50 mg) was dissolved in HCl-dioxane (2 ml) and the resultant solution was stirred for 1 hour and concentrated to dryness. The crude residue was purified by HPLC to provide 6-(2-amino-ethoxy)-3-{2-[4-(4-chloro-3-methoxy-phenyl)-piperazin-1-yl]-2-oxo-ethyl}-3H-benzooxazol-2-one: LCMS observed for (M+H)$^+$: 461.5.

Example 34

Synthesis of 5-Chloro-1-{2-[4-(4-chloro-3-methoxy-phenyl)-piperazin-1-yl]-2-oxo-ethyl}-3-methyl-1,3-dihydro-benzoimidazol-2-one (62)

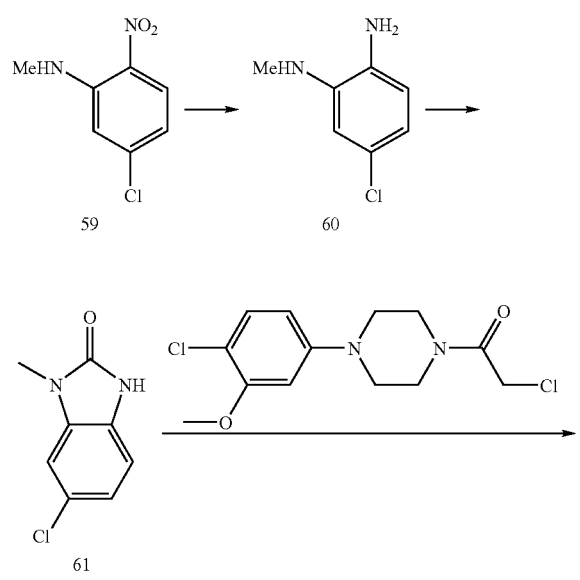

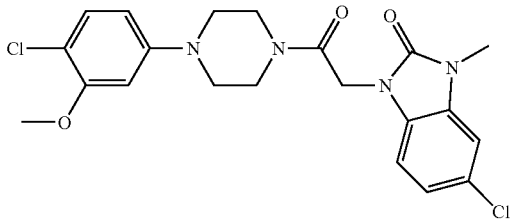

62

4-Chloro-N2-methyl-benzene-1,2-diamine (60): A mixture of (5-chloro-2-nitro-phenyl)-methyl-amine (59) (500 mg, 2.7 mmol, 1 eq), SnCl$_2$.2H$_2$O (3.0 g, 13.3 mmol, 5 eq) in ethyl acetate (25 ml) was refluxed overnight. The reaction mixture was diluted with ethyl acetate, washed with saturated potassium carbonate solution. The organic phase was concentrated and the crude residue was purified with flash chromatography to give 4-chloro-N2-methyl-benzene-1,2-diamine (60).

6-Chloro-1-methyl-1,3-dihydro-benzoimidazol-2-one (61): A mixture of 4-chloro-N2-methyl-benzene-1,2-diamine (60) (100 mg, 0.64 mmol, 1 eq), triphosgene (95 mg, 0.32 mmol, 0.5 eq), TEA (0.26 ml) in THF (2 ml) was stirred at rt for 4 hours. The reaction solution was washed with ethyl acetate and concentrated to provide 6-chloro-1-methyl-1,3-dihydro-benzoimidazol-2-one (61).

5-Chloro-1-{2-[4-(4-chloro-3-methoxy-phenyl)-piperazin-1-yl]-2-oxo-ethyl}-3-methyl-1,3-dihydro-benzoimidazol-2-one (62): A mixture of 6-chloro-1-methyl-1,3-dihydro-benzoimidazol-2-one (61) (75 mg, 0.41 mmol, 1 eq), 2-Chloro-1-[4-(4-chloro-3-methoxy-phenyl)-piperazin-1-yl]-ethanone (125 mg, 0.41 mmol, 1 eq), cesium carbonate (401 mg, 1.23 mmol, 3 eq) in DMF (2 ml) was stirred at rt overnight. The reaction solution was diluted with ethyl acetate, washed with water. The organic layer was evaporated to dryness and the crude residue was purified by flash chromatography to provide the desired product 5-chloro-1-{2-[4-(4-chloro-3-methoxy-phenyl)-piperazin-1-yl]-2-oxo-ethyl}-3-methyl-1,3-dihydro-benzoimidazol-2-one (62): LCMS observed for (M+H)$^+$: 449.2.

Example 35

Synthesis of {1-(4-chloro-3-methoxy-phenyl)-4-[2-(6-chloro-2-oxo-2,3-dihydro-benzofuran-3-yl)-acetyl]-piperazin-2-yl}-acetic acid methyl ester (65)

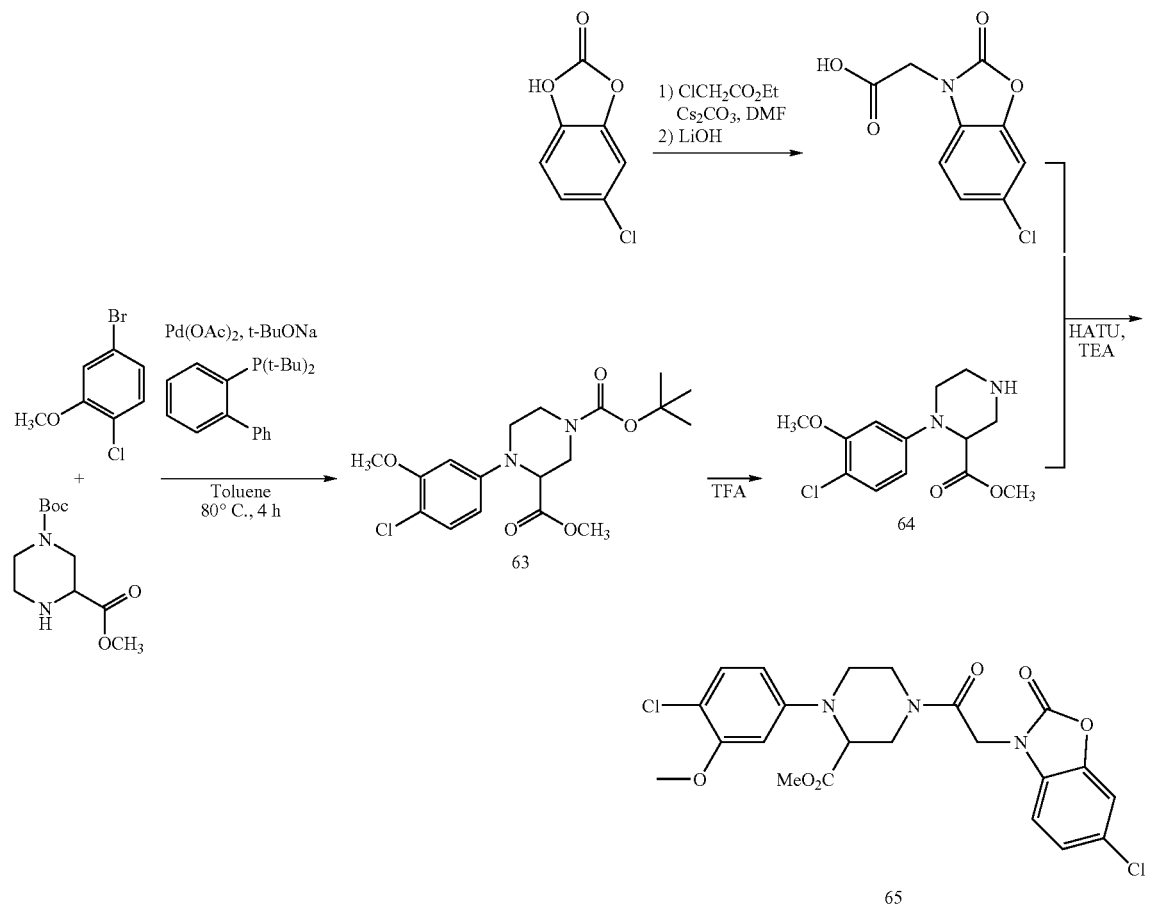

(6-Chloro-2-oxo-benzooxazol-3-yl)-acetic acid: (6-Chloro-2-oxo-benzooxazol-3-yl)-acetic acid was prepared by heating 6-chloro-3H-benzooxazol-2-one and ethyl chloroacetate in the presence of cesium carbonate in DMF at 60° C. The crude residue was dissolved followed in 1N LiOH in THF and stirred at rt. The resultant mixture was acidified with 1N HCl to pH ~1. The desired product precipitated out of solution and was isolated by filtration, and used directly in subsequent reactions without further purification.

4-(4-Chloro-3-methoxyphenyl)piperazine-1,3-dicarboxylic acid 1-tert-butyl ester 3-methyl ester (63): To a vial containing piperazine-1,3-dicarboxylic acid 1-tert-butyl ester 3-methyl ester (907 mg, 4.04 mmol), was added 4-bromo-1-chloro-2-methoxybenzene (913 mg, 4.12 mmol), palladium acetate (33 mg, 0.14 mmol) and 2-(di-tert-butylphosphino) biphenyl (88 mg, 0.29 mmol). The vial was evacuated and back-filled with nitrogen and to it was added toluene (2 mL). The reaction mixture was heated to 80° C. for 5 min to give a homogeneous solution. Upon cooling to room temperature, sodium tert-butoxide (557 mg, 5.80 mmol) was added to the reaction solution. The resultant mixture was again heated to 80° C. After 4 h, the reaction mixture was cooled to room temperature, then diluted with EtOAc (10 mL) and hexanes (10 mL). The resultant solution was filtered through celite, and the filtrate concentrated in vacuo and purified by silica gel flash chromatography (30 g) (20% EtOAc/Hexanes) to afford 4-(4-chloro-3-methoxyphenyl)piperazine-1,3-dicarboxylic acid 1-tert-butyl ester 3-methyl ester (63) (239 mg, 15% yield): HPLC retention time=2.72 minutes. MS (ES) [M+H]+ expected 385.2, found 385.1.

{1-(4-Chloro-3-methoxy-phenyl)-4-[2-(6-chloro-2-oxo-2,3-dihydro-benzofuran-3-yl)-acetyl]-piperazin-2-yl}-acetic acid methyl ester (64): To a vial containing 4-(4-Chloro-3-methoxyphenyl)piperazine-1,3-dicarboxylic acid 1-tert-butyl ester 3-methyl ester (63) (239 mg, 0.62 mmol) in DCM (10 mL) at 0° C. was added trifluoroacetic acid (5 mL) and the reaction mixture was stirred for 5 min and then warmed to room temperature. After 2 h, the reaction solution was diluted with EtOAc (25 mL), and the organic phase was washed with sat. aq. NaHCO₃ (3×10 mL). The pH of the combined aqueous phase was adjusted to 10 using a 10% solution of NaOH. The aqueous phase was then extracted with EtOAc (2×25 mL). The combined organic phase was then dried over MgSO₄ and concentrated in vacuo to afford 1-(4-chloro-3-methoxyphenyl)piperazine-2-carboxylic acid methyl ester (64) (168 mg, 95% yield). HPLC retention time=0.37 minutes. MS (ES) [M+H]+ expected=285.1, found 285.1.

{1-(4-Chloro-3-methoxy-phenyl)-4-[2-(6-chloro-2-oxo-2,3-dihydro-benzofuran-3-yl)-acetyl]-piperazin-2-yl}-acetic acid methyl ester (65): In a 4 mL vial was added 150 mg of [1-(4-chloro-3-methoxy-phenyl)-piperazin-2-yl]-acetic acid methyl ester hydrochloride (64) (0.47 mmol, 1.0 equiv), 107 mg of (6-chloro-2-oxo-benzooxazol-3-yl)-acetic acid (0.47 mmol, 1.0 equiv), 260 µL TEA (1.87 mmol, 4.0 equiv), 266 mg HATU (0.70 mmol, 1.5 equiv), and 3.2 mL NMP. The resultant mixture was stirred at room temperature overnight, and the crude product purified by reversed phase HPLC (acetonitrile—H₂O with 0.1% TFA as the eluent) to yield {1-(4-chloro-3-methoxy-phenyl)-4-[2-(6-chloro-2-oxo-2,3-dihydro-benzofuran-3-yl)-acetyl]-piperazin-2-yl}-acetic acid methyl ester (65): HPLC retention time=2.71 minutes (Agilent Zorbax SB-C18, 2.1×50 mm, 5µ, 35° C.) using 1 ml/min flow rate, a 2.5 minute gradient of 20% to 100% B with a 1.1 minute wash at 100% B (A=0.1% formic acid/5% acetonitrile/94.9% water, B=0.08% formic acid/5% water/94.9% acetonitrile); MS (ES) M+H expected=494.0, found=494.1.

Example 36

Synthesis of 5-chloro-3-{2-[4-(4-chloro-3-methoxy-phenyl)-piperazin-1-yl]-2-oxo-ethyl}-1-methyl-1,3-dihydro-benzoimidazol-2-one (66)

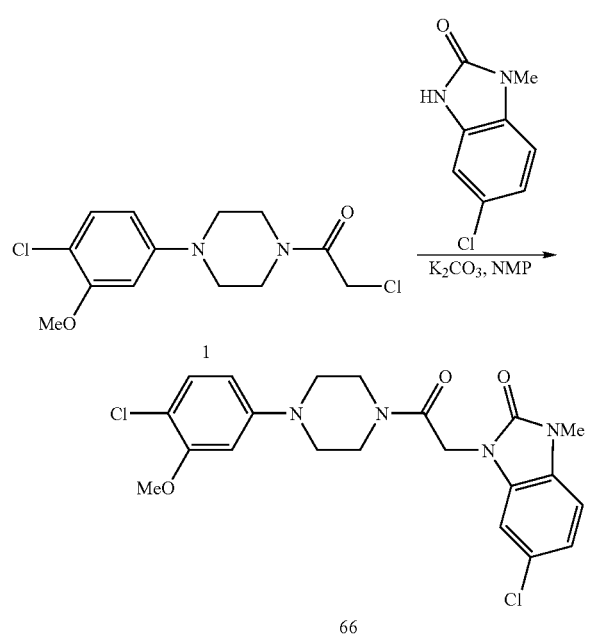

5-Chloro-3-{2-[4-(4-chloro-3-methoxy-phenyl)-piperazin-1-yl]-2-oxo-ethyl}-1-methyl-1,3-dihydro-benzoimidazol-2-one (66): 33 mg of 2-chloro-1-[4-(4-chloro-3-methoxy-phenyl)-piperazin-1-yl]-ethanone (1) (0.18 mmol, 1.00 equiv), 58 mg of 5-chloro-1-methyl-1,3-dihydro-benzoimidazol-2-one (0.19 mmol, 1.05 equiv), 100 mg of K₂CO₃ (0.72 mmol, 4.0 equiv), and 0.8 mL of NMP were combined in a 4 mL vial. The resultant mixture was heated at 60° C. in an oil bath overnight. The crude product was purified by reversed phase HPLC (acetonitrile—H₂O with 0.1% TFA as the eluent) to yield 5-chloro-3-{2-[4-(4-chloro-3-methoxy-phenyl)-piperazin-1-yl]-2-oxo-ethyl}-1-methyl-1,3-dihydro-benzoimidazol-2-one (66): HPLC retention time=2.40 minutes (Agilent Zorbax SB-C18, 2.1×50 mm, 5µ, 35° C.) using 1 ml/min flow rate, a 2.5 minute gradient of 20% to 100% B with a 1.1 minute wash at 100% B (A=0.1% formic acid/5% acetonitrile/94.9% water, B=0.08% formic acid/5% water/94.9% acetonitrile); MS (ES) M+H expected=449.0, found=449.1.

Example 37

Synthesis of 3-(2-(4-(4-Fluorobenzyl)-4-hydroxypiperidin-1-yl)-2-oxoethyl)-6-chlorobenzo[d]oxazol-2(3H)-one (68)

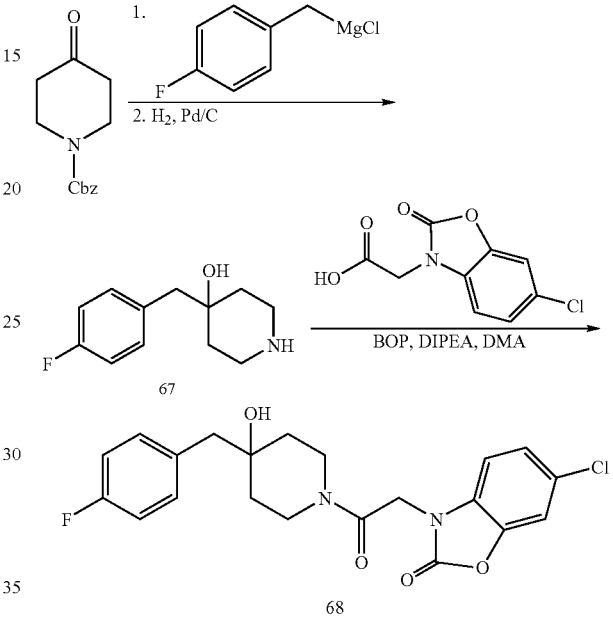

4-(4-Fluoro-benzyl)-piperidin-4-ol (67): To a round bottom flask equipped with a magnetic stirring bar was added 2.94 g of 4-oxo-piperidine-1-carboxylic acid benzyl ester (12.6 mmol, 1.0 equiv) and 25 mL of ether. The flask was fitted with a septum and a nitrogen inlet and cooled to −40° C. A 0.25 M solution of (4-fluoro)benzylmagnesium chloride (50 mL, 12.5 mmol, 1.0 equiv.) was added via syringe over 10 minutes to the reaction solution. After 1 h, the mixture was warmed to room temperature and stirred for 20 h. Then the solution was cooled to 0° C. and quenched with 30 mL of saturated aqueous ammonium-chloride. The aqueous layer was extracted with 100 mL of EtOAc. The combined organic layers were washed with saturated aqueous NaCl (3×25) and dried over MgSO₄. The resultant yellow oil was purified by flash chromatography to afford 1.058 g of 4-(4-Fluoro-benzyl)-4-hydroxy-piperidine-1-carboxylic acid benzyl ester (3.08 mmol, 25% yield). The crude product was diluted in methanol (12 mL) and added to a round bottom flask containing a magnetic stirring bar and 200 mg of 10% Pd/C. The flask was evacuated, and back-filled with hydrogen (1 atm). After 24 h of vigorous stirring under nitrogen atmosphere, the solution was filtered through celite and concentrated in vacuo to afford 4-(4-fluoro-benzyl)-piperidin-4-ol (67) in quantitative yield (644 mg): HPLC retention time=0.26 minutes (Agilent Zorbax SB-C18, 2.1×50 mm, 5µ, 35° C.) using 1 mL/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expected=210.1, found 210.1.

3-(2-(4-(4-Fluorobenzyl)-4-hydroxypiperidin-1-yl)-2-oxoethyl)-6-chlorobenzo[d]oxazol-2(3H)-one (68): To a vial containing 2-(6-chloro-2-oxobenzo[d]oxazol-3(2H)-yl)acetic acid (67) (60 mg, 0.3 mmol) was added DMA (0.6 mL), BOP (133 mg, 0.3 mmol), 4-(4-fluorobenzyl)piperidin-4-ol (63 mg, 0.3 mmol) and DIPEA (180 µL, 1.0 mmol). The resultant solution was stirred at room temperature for 18 h. The reaction solution was then diluted with EtOAc (50 mL) and washed with 0.1 N HCl (2×10 mL) and 10% aq. NaHCO$_3$ (2×10 mL). The organic layer was dried over MgSO$_4$ and concentrated in vacuo. The crude residue was purified by preparative HPLC (20→95% gradient of MeCN—H$_2$O with 0.1% TFA) and the pure fractions were lyophilized to afford the title compound (68) (54 mg, 50% yield): HPLC retention time=2.33 minutes. MS (ES) [M+H]$^+$ expected 419.1, found 419.1.

Example 38

Synthesis of 6-Chloro-3-{2-[4-(4-chloro-3-methoxy-phenyl)-4-hydroxy-piperidin-1-yl]-2-oxo-ethyl}-3H-benzooxazol-2-one (70)

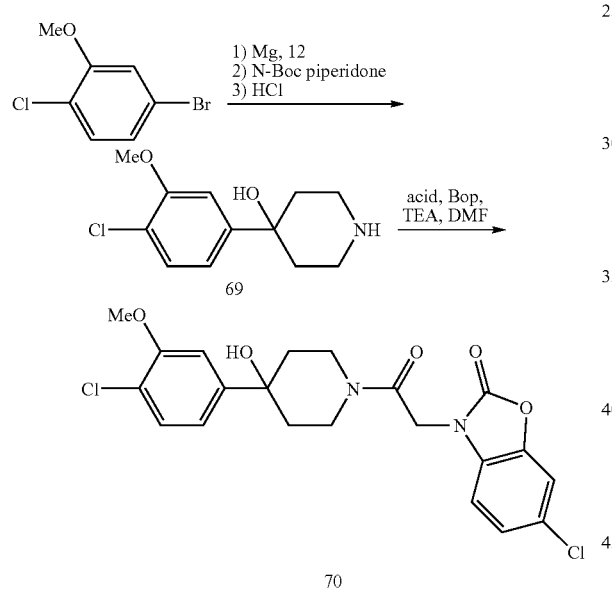

4-(4-Chloro-3-methoxy-phenyl)-4-hydroxy-piperidine-1-carboxylic acid tert-butyl ester: Magnesium turnings (2.60 g) in a flask were stirred vigorously under vacuum at room temperature for 12 h and then the flask was filled with nitrogen gas. THF (20 mL) was added followed by the addition of one crystal of 12. The mixture was cooled to 0° C. and a solution of 5-bromo-2-chloroanisole (6.64 g) in THF (100 mL) was added in a period of 10 min. The mixture was warmed up to room temperature and stirred at room temperature for 15 min before it was heated to 45° C. for 2 h to provide a solution of the Grignard solution. To 24 mL of the Grignard solution obtained from above (at −40° C.) was added N-Boc-piperidone (1.0 g) in one portion. The resultant mixture was warmed up to room temperature, stirred for 1 h and quenched by the addition of sat. aqueous NH$_4$Cl solution (20 mL). The organic layer was separated and the aqueous layer was extracted by EtOAc (3×20 mL). The combined organic layers were dried (Na$_2$SO$_4$), filtered and evaporated in vacuo. The crude residue was purified by flash chromatography to provide 4-(4-Chloro-3-methoxy-phenyl)-4-hydroxy-piperidine-1-carboxylic acid tert-butyl ester as a colorless oil (502 mg).

4-(4-Chloro-3-methoxy-phenyl)-piperidin-4-ol (69): To a solution of 4-(4-Chloro-3-methoxy-phenyl)-4-hydroxy-piperidine-1-carboxylic acid tert-butyl ester (502 mg) in MeOH (5 mL) was added a solution of HCl in ether (2 M, 9.5 mL). The resultant mixture was stirred at room temperature for 1 h followed by the addition of ether (50 mL). The reaction mixture was stirred at 0° C. for an additional 30 min, then filtered and concentrated to provide 4-(4-Chloro-3-methoxy-phenyl)-piperidin-4-ol (69) in the form of HCl salt as a white solid.

6-Chloro-3-{2-[4-(4-chloro-3-methoxy-phenyl)-4-hydroxy-piperidin-1-yl]-2-oxo-ethyl}-3H-benzooxazol-2-one (70): A mixture of 2-(6-chloro-2-oxobenzo[d]oxazol-3(2H)-yl)acetic acid (22.7 mg, 0.1 mmol, 1 equiv), 4-(4-chloro-3-methoxy-phenyl)-piperidin-4-ol hydrochloride (69) (27.7 mg, 1 equiv), BOP (58 mg, 1.3 equiv), triethylamine (56 µL, 4 equiv) in 1 ml of DMF was stirred at room temperature for overnight. The solution was then diluted with EtOAc (50 mL) and washed with water. The organic layer was dried over sodium sulfate and concentrated in vacuo. The crude residue was purified by flash chromatography to provide 6-chloro-3-{2-[4-(4-chloro-3-methoxy-phenyl)-4-hydroxy-piperidin-1-yl]-2-oxo-ethyl}-3H-benzooxazol-2-one (70): MS (ES) [M+H]$^+$ expected 451.1, found 451.1.

Example 39

Synthesis of 6-Chloro-1-{2-[4-(4-chloro-3-methoxy-phenyl)-piperazin-1-yl]-2-oxo-ethyl}-1,4-dihydro-benzo[d][1,3]oxazin-2-one (73)

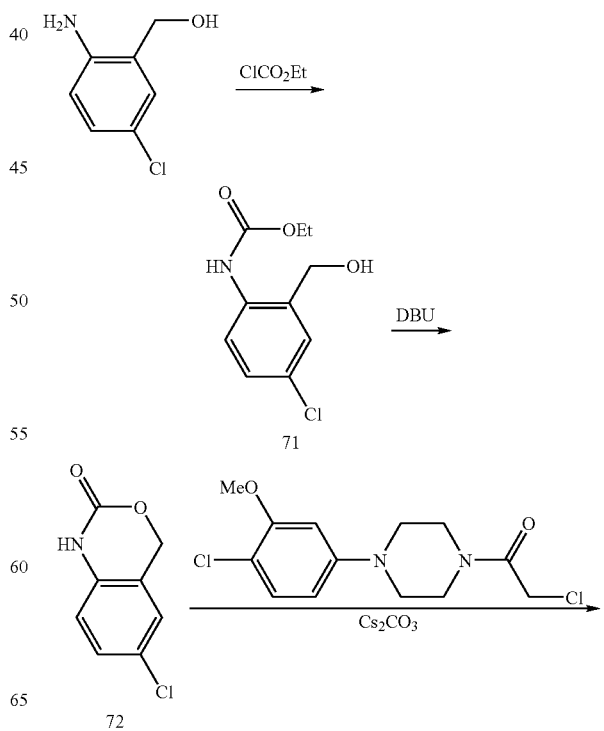

-continued

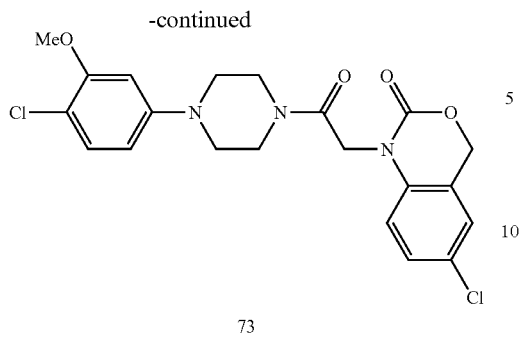

73

(4-Chloro-2-hydroxymethyl-phenyl)-carbamic acid ethyl ester (71): To a solution of (2-amino-5-chloro-phenyl)-methanol (1.58 g, 10 mmol, 1 equiv) in 15 mL of DCM was slowly added ethyl chloroformate (1.05 mL, 1.1 equiv) and pyridine (1.2 mL, 1.5 equiv). After stirring for 1 h, the resultant mixture was diluted with EtOAc and washed with water. The organic layer was dried over sodium sulfate, filtered and concentrated in vacuo to provide the crude product, (4-Chloro-2-hydroxymethyl-phenyl)-carbamic acid ethyl ester (71), which was used in subsequent reactions without further purification.

6-Chloro-1,4-dihydro-benzo[d][1,3]oxazin-2-one (72): To a solution of (4-chloro-2-hydroxymethyl-phenyl)-carbamic acid ethyl ester (71) obtained from the previous step in 5 mL of toluene was added 3 mL of DBU (2 equiv) and the resultant solution was heated at 110° C. overnight. After cooling to rt, the mixture was diluted with EtOAc and washed with water. The organic layer was dried over sodium sulfate, filtered and dried in vacuo to give 6-chloro-1,4-dihydro-benzo[d][1,3]oxazin-2-one (72).

6-Chloro-1-{2-[4-(4-chloro-3-methoxy-phenyl)-piperazin-1-yl]-2-oxo-ethyl}-1,4-dihydro-benzo[d][1,3]oxazin-2-one (73): A mixture of 2-chloro-1-[4-(4-chloro-3-methoxy-phenyl)-piperazin-1-yl]-ethanone (303 mg, 1 mmol, 1 equiv), 6-chloro-1,4-dihydro-benzo[d][1,3]oxazin-2-one (72) (183 mg, 1 equiv), and Cs$_2$CO$_3$ (56 µL, 4 equiv) in 2 ml of DMF was stirred at 60° C. overnight. The reaction solution was then diluted with EtOAc (50 mL) and washed with water. The organic layer was dried over sodium sulfate and concentrated in vacuo. The resultant crude residue was purified by flash chromatography to give 6-chloro-1-{2-[4-(4-chloro-3-methoxy-phenyl)-piperazin-1-yl]-2-oxo-ethyl}-1,4-dihydro-benzo[d][1,3]oxazin-2-one (73): MS (ES) [M+H]$^+$ expected 450.1, found 450.1.

Example 40

Synthesis of 6-chloro-3-{2-[3-(3-chloro-2-methyl-phenyl)-4-oxo-imidazolidin-1-yl]-2-oxo-ethyl}-3H-benzooxazol-2-one (77)

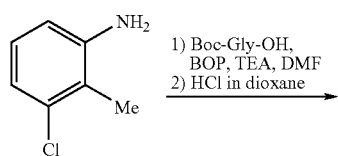

-continued

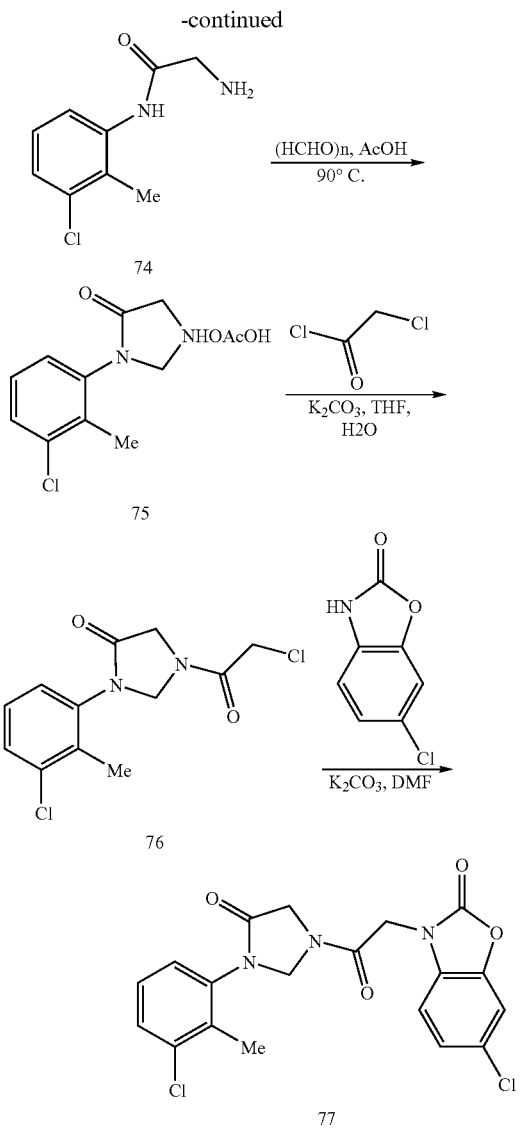

2-Amino-N-(3-chloro-2-methyl-phenyl)-acetamide (74): To a mixture of 2-methyl-3-chloroaniline (14.16 g, 100 mmol, 1 equiv), Boc-glycine (17.52 g, 1 equiv), BOP reagent (48.6 g, 1.1 equiv) in 50 mL of DMF was added TEA (42 mL, 3 equiv). After overnight, standard aqueous workup followed by flash chromatography gave 20 g of [(3-chloro-2-methyl-phenylcarbamoyl)-methyl]-carbamic acid tert-butyl ester, which was treated with ~300 mL of 4N HCl in dioxane overnight to afford 2-amino-N-(3-chloro-2-methyl-phenyl)-acetamide (74).

3-(3-Chloro-2-methyl-phenyl)-imidazolidin-4-one (75): A mixture of 2-amino-N-(3-chloro-2-methyl-phenyl)-acetamide (74) (1.18 g, 1 equiv), paraformaldehyde (HCHO)$_n$ (0.77 g, 1.5 equiv) and 3 mL of acetic acid was heated at 90° C. for 3 h and evaporated to dryness to afford 3-(3-chloro-2-methyl-phenyl)-imidazolidin-4-one (75) as acetic acid salt.

1-(2-Chloro-acetyl)-3-(3-chloro-2-methyl-phenyl)-imidazolidin-4-one (76): To a mixture of 3-(3-chloro-2-methyl-phenyl)-imidazolidin-4-one acetic acid salt (75) (422 mg, 1 equiv) and K$_2$CO$_3$ (552 mg) in 5 mL of DCM/water (1:1 v/v) was added chloroacetyl chloride (240 µL, 1.5 equiv). One hour later, the organic layer was separated and dried over sodium sulfate to give 1-(2-chloro-acetyl)-3-(3-chloro-2-methyl-phenyl)-imidazolidin-4-one (76).

6-Chloro-3-{2-[3-(3-chloro-2-methyl-phenyl)-4-oxo-imidazolidin-1-yl]-2-oxo-ethyl}-3H-benzooxazol-2-one (77): A mixture of (2-chloro-acetyl)-3-(3-chloro-2-methyl-phenyl)-imidazolidin-4-one (76) (28.6 mg, 1 equiv), 6-Chloro-3H-benzooxazol-2-one (16.9 mg, 1 equiv) and potassium carbonate (27 mg, 2 equiv) in DMF (2 ml) was stirred at 60° C. overnight, diluted with ethyl acetate, washed with water, purified with HPLC to give 6-chloro-3-{2-[3-(3-chloro-2-methyl-phenyl)-4-oxo-imidazolidin-1-yl]-2-oxo-ethyl}-3H-benzooxazol-2-one (77): LCMS observed for (M+H)$^+$: 421.2.

Example 41

Synthesis of 5-Chloro-1-{2-[4-(4-fluoro-benzyl)-4-hydroxy-piperidin-1-yl]-2-oxo-ethyl}-1,3-dihydro-benzoimidazol-2-one (79) and 6-Chloro-1-{2-[4-(4-fluoro-benzyl)-4-hydroxy-piperidin-1-yl]-2-oxo-ethyl}-1,3-dihydro-benzoimidazol-2-one (80)

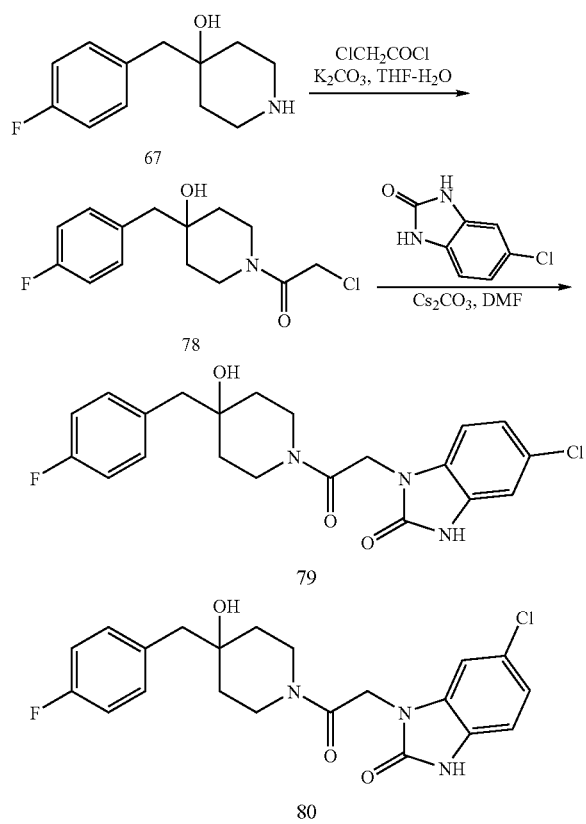

2-Chloro-1-[4-(4-fluoro-benzyl)-4-hydroxy-piperidin-1-yl]-ethanone (78): 2-Chloro-1-[4-(4-fluoro-benzyl)-4-hydroxy-piperidin-1-yl]-ethanone was prepared from 4-(4-fluorobenzyl)piperidin-4-ol according to the procedure described for Compound 76 in Example 40.

5-Chloro-1-{2-[4-(4-fluoro-benzyl)-4-hydroxy-piperidin-1-yl]-2-oxo-ethyl}-1,3-dihydro-benzoimidazol-2-one (79) and 6-chloro-1-{2-[4-(4-fluoro-benzyl)-4-hydroxy-piperidin-1-yl]-2-oxo-ethyl}-1,3-dihydro-benzoimidazol-2-one (80): A mixture of 2-chloro-1-[4-(4-fluoro-benzyl)-4-hydroxy-piperidin-1-yl]-ethanone (78) (57 mg, 1 equiv), 6-Chloro-3H-benzooxazol-2-one (34 mg, 1 equiv) and potassium carbonate (54 mg, 2 equiv) in DMF (2 ml) was stirred at 60° C. overnight, diluted with ethyl acetate, washed with water, purified with HPLC to give 5-chloro-1-{2-[4-(4-fluoro-benzyl)-4-hydroxy-piperidin-1-yl]-2-oxo-ethyl}-1,3-dihydro-benzoimidazol-2-one (79) (LCMS observed for (M+H)$^+$: 418.0) and 6-chloro-1-{2-[4-(4-fluoro-benzyl)-4-hydroxy-piperidin-1-yl]-2-oxo-ethyl}-1,3-dihydro-benzoimidazol-2-one (80) (LCMS observed for (M+H)$^+$: 418.0).

Example 42

This example illustrates the evaluation of the biological activity associated with compounds of interest (candidate compounds) of the invention.

Materials and Methods
  A. Cells
    1. CCR1 Expressing Cells
    a) THP-1 Cells
    THP-1 cells were obtained from ATCC (TIB-202) and cultured as a suspension in RPMI-1640 medium supplemented with 2 mM L-glutamine, 1.5 g/L sodium bicarbonate, 4.5 g/L glucose, 10 mM HEPES, 1 mM sodium pyruvate, 0.05% 2-mercaptoethanol and 10% FBS. Cells were grown under 5% $CO_2$/95% air, 100% humidity at 37° C. and sub-cultured twice weekly at 1:5 (cells were cultured at a density range of $2 \times 10^5$ to $2 \times 10^6$ cells/mL) and harvested at $1 \times 10^6$ cells/mL. THP-1 cells express CCR1 and can be used in CCR1 binding and functional assays.
    b) Isolated Human Monocytes
    Monocytes were isolated from human buffy coats using the Miltenyi bead isolation system (Miltenyi, Auburn, Calif.). Briefly, following a Ficoll gradient separation to isolate peripheral blood mononuclear cells, cells were washed with PBS and the red blood cells lysed using standard procedures. Remaining cells were labeled with anti-CD14 antibodies coupled to magnetic beads (Miltenyi Biotech, Auburn, Calif.). Labeled cells were passed through AutoMACS (Miltenyi, Auburn, Calif.) and positive fraction collected. Monocytes express CCR1 and can be used in CCR1 binding and functional assays.
  B. Assays
    1. Inhibition of CCR1 Lipand Binding
    CCR1 expressing cells were centrifuged and resuspended in assay buffer (20 mM HEPES pH 7.1, 140 mM NaCl, 1 mM $CaCl_2$, 5 mM $MgCl_2$, and with 0.2% bovine serum albumin) to a concentration of $5 \times 10^6$ cells/mL for THP-1 cells and $5 \times 10^5$ for monocytes. Binding assays were set up as follows. 0.1 mL of cells ($5 \times 10^5$ THP-1 cells/well or $5 \times 10^4$ monocytes) was added to the assay plates containing the compounds, giving a final concentration of ~2-10 μM each compound for screening (or part of a dose response for compound $IC_{50}$ determinations). Then 0.1 mL of $^{125}$I labeled MIP-1α (obtained from Perkin Elmer Life Sciences, Boston, Mass.) or 0.1 mL of 125, labeled CCL15/leukotactin (obtained as a custom radiolabeling by Perkin Elmer Life Sciences, Boston, Mass.) diluted in assay buffer to a final concentration of ~50 μM, yielding ~30,000 cpm per well, was added (using $^{125}$I labeled MIP-1α with THP-1 cells and $^{125}$I labeled CCL15/leukotactin with monocytes), the plates sealed and incubated for approximately 3 hours at 4° C. on a shaker platform. Reactions were aspirated onto GF/B glass filters pre-soaked in 0.3% polyethyleneimine (PEI) solution, on a vacuum cell harvester (Packard Instruments; Meriden, Conn.). Scintillation fluid (40 μl; Microscint 20, Packard Instruments) was added to each well, the plates were sealed and radioactivity measured in a Topcount scintillation counter (Packard Instruments). Control wells containing either diluent only (for total counts) or excess MIP-1α or MIP-1β (1 µg/mL, for non-specific binding) were used to calculate the percent of total inhibition for compound. The computer program Prism from GraphPad, Inc. (San Diego, Calif.) was used to calculate $IC_{50}$ values. $IC_{50}$ values are those concentrations required to reduce the binding of labeled MIP-1α to the receptor by 50%. (For further descriptions of ligand binding and other functional assays, see Dairaghi, et al., *J. Biol. Chem.* 274:21569-21574 (1999), Penfold, et al., Proc. Natl. Acad. Sci. USA. 96:9839-9844 (1999), and Dairaghi, et al., *J. Biol. Chem.* 272:28206-28209 (1997)).

2. Calcium Mobilization

To detect the release of intracellular stores of calcium, cells (THP-1 or monocytes) were incubated with 3 µM of INDO-1AM dye (Molecular Probes; Eugene, Oreg.) in cell media for 45 minutes at room temperature and washed with phosphate buffered saline (PBS). After INDO-1AM loading, the cells were resuspended in flux buffer (Hank's balanced salt solution (HBSS) and 1% FBS). Calcium mobilization was measured using a Photon Technology International spectrophotometer (Photon Technology International; New Jersey) with excitation at 350 nm and dual simultaneous recording of fluorescence emission at 400 nm and 490 nm. Relative intracellular calcium levels were expressed as the 400 nm/490 rn emission ratio. Experiments were performed at 37° C. with constant mixing in cuvettes each containing $10^6$ cells in 2 mL of flux buffer. The chemokine ligands may be used over a range from 1 to 100 nM. The emission ratio was plotted over time (typically 2-3 minutes). Candidate ligand blocking compounds (up to 10 µM) were added at 10 seconds, followed by chemokines at 60 seconds (i.e., MIP-1α; R&D Systems; Minneapolis, Minn.) and control chemokine (i.e., SDF-1α; R&D Systems; Minneapolis, Minn.) at 150 seconds.

3. Chemotaxis Assays

Chemotaxis assays were performed using 5 fm pore polycarbonate, polyvinylpyrrolidone-coated filters in 96-well chemotaxis chambers (Neuroprobe; Gaithersburg, Md.) using chemotaxis buffer (Hank's balanced salt solution (HBSS) and 1% FBS). CCR1 chemokine ligands (i.e., MIP-1α, CCL15/Leukotactin; R&D Systems; Minneapolis, Minn.) are use to evaluate compound mediated inhibition of CCR1 mediated migration. Other chemokines (i.e., SDF-1α; R&D Systems; Minneapolis, Minn.) are used as specificity controls. The lower chamber was loaded with 29 µl of chemokine (i.e., 0.1 nM CCL15/Leukotactin) and varying amounts of compound; the top chamber contained 100,000 THP-1 or monocyte cells in 20 µl. The chambers were incubated 1-2 hours at 37° C., and the number of cells in the lower chamber quantified either by direct cell counts in five high powered fields per well or by the CyQuant assay (Molecular Probes), a fluorescent dye method that measures nucleic acid content and microscopic observation.

C. Identification of Inhibitors of CCR1

1. Assay

To evaluate small organic molecules that prevent the receptor CCR1 from binding ligand, an assay was employed that detected radioactive ligand (i.e, MIP-1α or CCL15/Leukotactin) binding to cells expressing CCR1 on the cell surface (for example, THP-1 cells or isolated human monocytes). For compounds that inhibited binding, whether competitive or not, fewer radioactive counts are observed when compared to uninhibited controls.

THP-1 cells and monocytes lack other chemokine receptors that bind the same set of chemokine ligands as CCR1 (i.e., MIP-1α, MPIF-1, Leukotactin, etc.). Equal numbers of cells were added to each well in the plate. The cells were then incubated with radiolabeled MIP-1α. Unbound ligand was removed by washing the cells, and bound ligand was determined by quantifying radioactive counts. Cells that were incubated without any organic compound gave total counts; non-specific binding was determined by incubating the cells with unlabeled ligand and labeled ligand. Percent inhibition was determined by the equation:

$$\% \text{ inhibition} = (1 - [(\text{sample cpm}) - (\text{nonspecific cpm})] / [(\text{total cpm}) - (\text{nonspecific cpm})]) \times 100.$$

2. Dose Response Curves

To ascertain a candidate compound's affinity for CCR1 as well as confirm its ability to inhibit ligand binding, inhibitory activity was titered over a $1 \times 10^{-10}$ to $1 \times 10^{-4}$ M range of compound concentrations. In the assay, the amount of compound was varied; while cell number and ligand concentration were held constant.

3. CCR1 Functional Assays

CCR1 is a seven transmembrane, G-protein linked receptor. A hallmark of signaling cascades induced by the ligation of some such receptors is the pulse-like release of calcium ions from intracellular stores. Calcium mobilization assays were performed to determine if the candidate CCR1 inhibitory compounds were able to also block aspects of CCR1 signaling. Candidate compounds able to inhibit ligand binding and signaling with an enhanced specificity over other chemokine and non-chemokine receptors were desired.

Calcium ion release in response to CCR1 chemokine ligands (i.e., MIP-1α, MPIF-1, Leukotactin, etc.) was measured using the calcium indicator INDO-1. THP-1 cells or monocytes were loaded with INDO-1/AM and assayed for calcium release in response to CCR1 chemokine ligand (i.e., MIP-1α) addition. To control for specificity, non-CCR1 ligands, specifically bradykinin, was added, which also signals via a seven transmembrane receptor. Without compound, a pulse of fluorescent signal will be seen upon MIP-1α addition. If a compound specifically inhibits CCR1-MIP-1α signaling, then little or no signal pulse will be seen upon MIP-1α addition, but a pulse will be observed upon bradykinin addition. However, if a compound non-specifically inhibits signaling, then no pulse will be seen upon both MIP-1α and bradykinin addition.

One of the primary functions of chemokines is their ability to mediate the migration of chemokine receptor-expressing cells, such as white blood cells. To confirm that a candidate compound inhibited not only CCR1 specific binding and signaling (at least as determined by calcium mobilization assays), but also CCR1 mediated migration, a chemotaxis assay was employed. THP-1 myelomonocytic leukemia cells, which resemble monocytes, as wells as freshly isolated monocytes, were used as targets for chemoattraction by CCR1 chemokine ligands (i.e., MIP-1α, CCL15/leukotactin). Cells were place in the top compartment of a microwell migration chamber, while MIP-1α (or other potent CCR1 chemokine ligand) and increasing concentrations of a candidate compound was loaded in the lower chamber. In the absence of inhibitor, cells will migrate to the lower chamber in response to the chemokine agonist; if a compound inhibited CCR1 function, then the majority of cells will remain in the upper chamber. To ascertain a candidate compound's affinity for CCR1 as well as to confirm its ability to inhibit CCR1 mediated cell migration, inhibitory activity was titered over a 1×10$^{-10}$ to 1×10$^{-4}$ M range of compound concentrations in this chemotaxis assay. In this assay, the amount of compound was varied; while cell number and chemokine agonist concentrations were held constant. After the chemotaxis chambers were incubated 1-2 hours at 37° C., the responding cells in the lower chamber were quantified by labeling with the CyQuant assay (Molecular Probes), a fluorescent dye method that measures nucleic acid content, and by measuring with a Spectrafluor Plus (Tecan). The computer program Prism from GraphPad, Inc. (San Diego, Calif.) was used to calculate IC$_{50}$ values. IC$_{50}$ values are those compound concentrations required to inhibit the number of cells responding to a CCR1 agonist by 50%.

4. In Vivo Efficacy a) Rabbit Model of Destructive Joint Inflammation

To study the effects of candidate compounds on inhibiting the inflammatory response of rabbits to an intra-articular injection of the bacterial membrane component lipopolysaccharide (LPS), a rabbit model of destructive joint inflammation is used. This study design mimics the destructive joint inflammation seen in arthritis. Intra-articular injection of LPS causes an acute inflammatory response characterized by the release of cytokines and chemokines, many of which have been identified in rheumatoid arthritic joints. Marked increases in leukocytes occur in synovial fluid and in synovium in response to elevation of these chemotactic mediators. Selective antagonists of chemokine receptors have shown efficacy in this model (see Podolin, et al., *J. Immunol.* 169(11):6435-6444 (2002)).

A rabbit LPS study is conducted essentially as described in Podolin, et al. ibid., female New Zealand rabbits (approximately 2 kilograms) are treated intra-articularly in one knee with LPS (10 ng) together with either vehicle only (phosphate buffered saline with 1% DMSO) or with addition of CCX-105 (dose 1=50 μM or dose 2=100 μM) in a total volume of 1.0 mL. Sixteen hours after the LPS injection, knees are lavaged and cells counts are performed. Beneficial effects of treatment were determined by histopathologic evaluation of synovial inflammation. Inflammation scores are used for the histopathologic evaluation: 1-minimal, 2-mild, 3-moderate, 4-moderate-marked.

b) Evaluation of a Candidate Compound in a Rat Model of Collagen Induced Arthritis A 17 day developing type II collagen arthritis study is conducted to evaluate the effects of a candidate compound on arthritis induced clinical ankle swelling. Rat collagen arthritis is an experimental model of polyarthritis that has been widely used for preclinical testing of numerous anti-arthritic agents (see Trentham, et al., *J. Exp. Med.* 146(3):857-868 (1977), Bendele, et al., *Toxicologic Pathol.* 27:134-142 (1999), Bendele, et al., *Arthritis Rheum.* 42:498-506 (1999)). The hallmarks of this model are reliable onset and progression of robust, easily measurable polyarticular inflammation, marked cartilage destruction in association with pannus formation and mild to moderate bone resorption and periosteal bone proliferation.

Female Lewis rats (approximately 0.2 kilograms) are anesthetized with isoflurane and injected with Freund's Incomplete Adjuvant containing 2 mg/mL bovine type II collagen at the base of the tail and two sites on the back on days 0 and 6 of this 17 day study. A candidate compound is dosed daily in a sub-cutaneous manner from day 0 till day 17 at a efficacious dose. Caliper measurements of the ankle joint diameter were taken, and reducing joint swelling is taken as a measure of efficacy.

In the table below, structures and activity are provided for representative compounds described herein. Activity is provided as follows for either the chemotaxis assay or binding assay as described above: +++, 1000 nM<IC$_{50}$<25000 nM; and ++++, IC$_{50}$<1000 nM.

TABLE 2

Structure

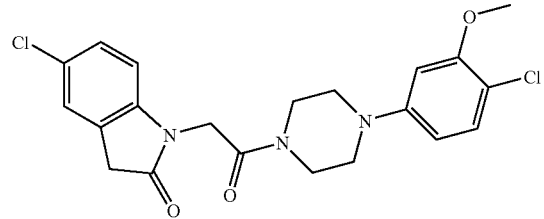

1.001/++++

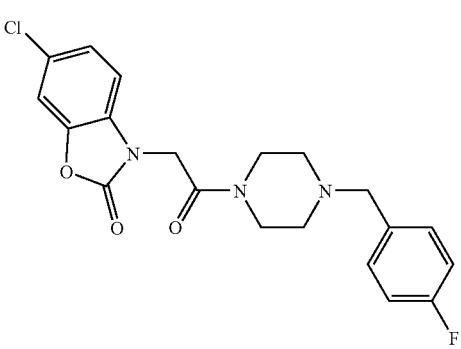

1.003/+++

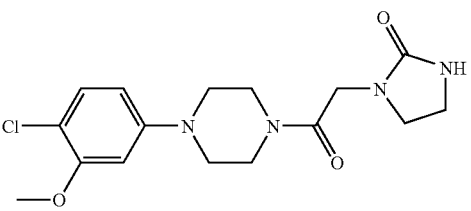

1.005/+++

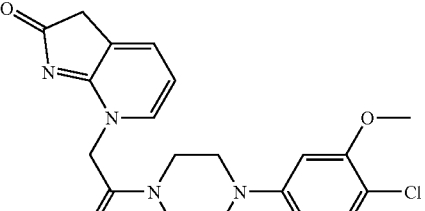

1.007/+++

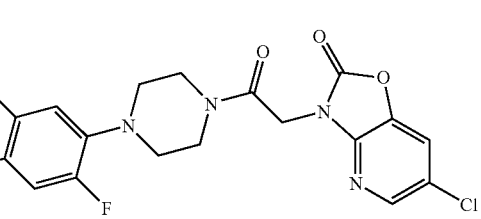

1.009/++++

TABLE 2-continued

Structure 1.011/++++

1.013/++++

1.015/++++

1.017/++++

1.019/++++

1.021/++++

TABLE 2-continued

Structure 1.023/++++

1.025/+++

1.027/+++

1.029/+++

1.031/++++

1.033/++++

TABLE 2-continued
Structure
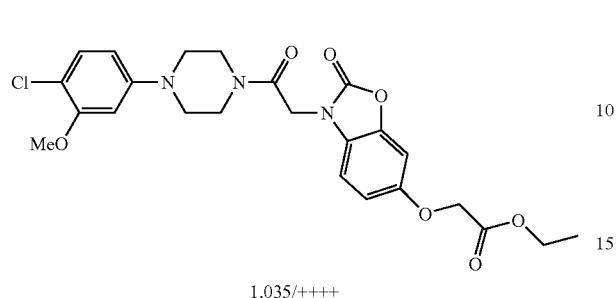
1.035/++++
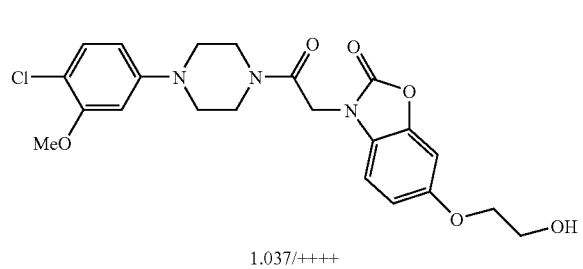
1.037/++++
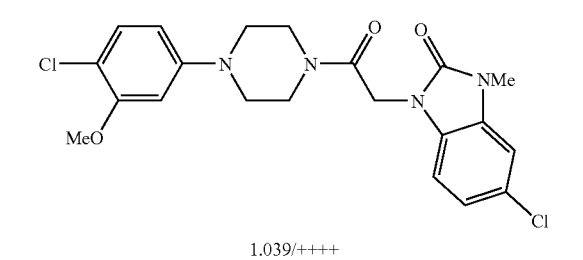
1.039/++++
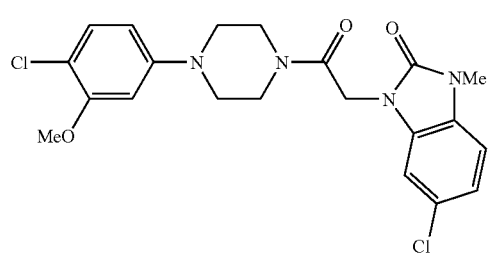
1.041/++++
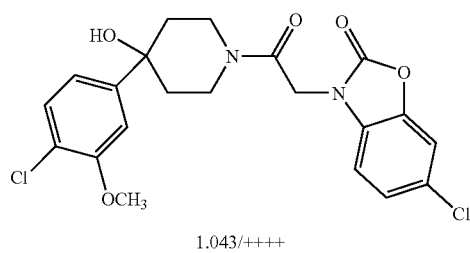
1.043/++++
TABLE 2-continued
Structure
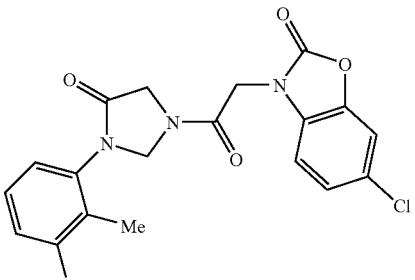
1.045/++++
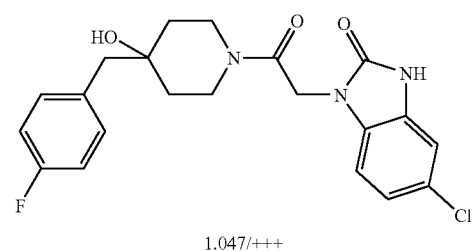
1.047/+++
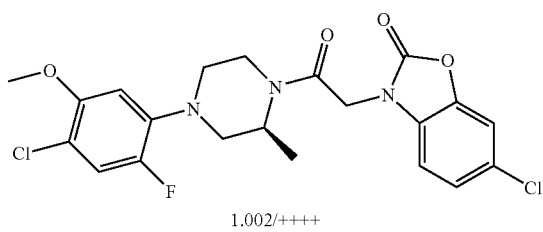
1.002/++++
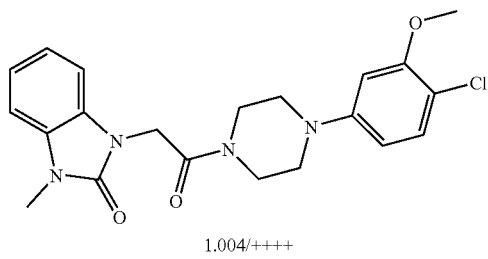
1.004/++++
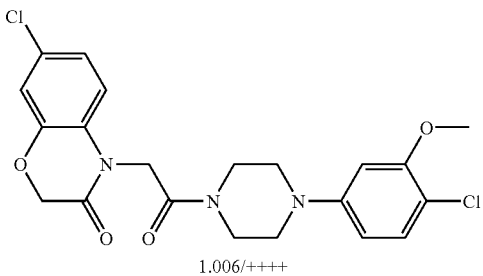
1.006/++++

TABLE 2-continued

| Structure |
|---|
| 1.008/++++ |
| 1.010/+++ |
| 1.012/++++ |
| 1.014/++++ |
| 1.016/++++ |
| 1.018/++++ |
| 1.020/++++ |
| 1.022/++++ |
| 1.024/++++ |
| 1.026/+++ |
| 1.028/+++ |
| 1.030/++++ |

What is claimed is:

1. A compound having Formula I:

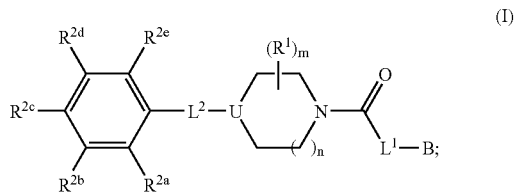

or pharmaceutically acceptable salts and N-oxides thereof; wherein each $R^1$ is independently selected from the group consisting of $-CO_2R^a$ and $C_{1-8}$ alkyl, wherein $R^a$ is selected from the group consisting of hydrogen, and $C_{1-8}$ alkyl;

the subscript m is 0 or 1;

$R^{2c}$ is halogen or $-OR^c$;

$R^{2d}$ is halogen or $-OR^c$;

$R^{2a}$, $R^{2b}$ and $R^{2e}$ at each occurrence are each independently selected from the group consisting of hydrogen, halogen, and $-OR^c$, wherein each $R^c$ is independently selected from hydrogen, and $C_{1-8}$ alkyl;

B represents a benzoxazoline ring system linked through its nitrogen atom to the remainder of the molecule, and is further substituted with 0 to 4 $R^3$ substitutents, and at each occurrence, $R^3$ is independently selected from the group consisting of hydrogen, halogen, $-OR^f$, $-CN$, unsubstituted $C_{1-6}$alkyl and an oxadiazole ring, or any two $R^3$ substituents attached to the same atom on B are taken together to form =O, wherein each $R^f$ is independently selected from hydrogen, and $C_{1-8}$ alkyl, wherein the aliphatic portions of $R^f$, are optionally further substituted with a member selected from the group consisting of —OH, —$CO_2$H, —$CO_2R^o$, and —$NH_2$, wherein $R^o$ is unsubstituted $C_{1-6}$ alkyl;

$L^1$ is $CH_2$;

the symbol U is N;

$L^2$ is a direct bond; and the subscript n is 1.

2. The compound of claim 1, wherein $R^1$, when present, is selected from the group consisting of —$CH_3$ and —$CO_2$Me.

3. The compound of claim 1, wherein $R^{2c}$ and $R^{2d}$ are each independently selected from the group consisting of halogen and —$OCH_3$; and $R^{2a}$, $R^{2b}$ and $R^{2e}$ are independently selected from the group consisting of hydrogen, halogen and —$OCH_3$.

4. The compound of claim 1, having a formula selected from the group consisting of

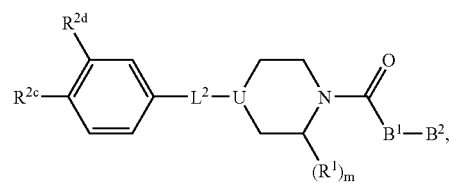

Ia

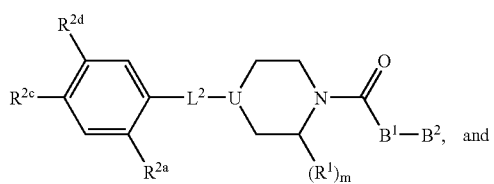

Ib

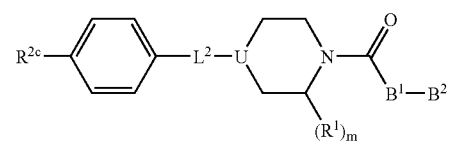

Ic wherein $R^{2c}$ is halogen; $R^{2d}$ is —$OCH_3$; $R^{2a}$ is halogen; the subscript m is 0-1; and $R^1$, when present, is —$CH_3$ or —$CO_2CH_3$.

5. The compound of claim 1, wherein said compound is a compound selected from the group consisting of:

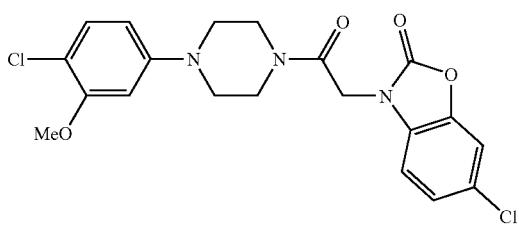

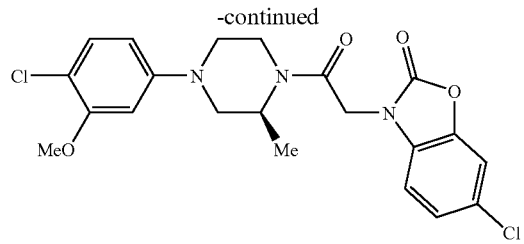

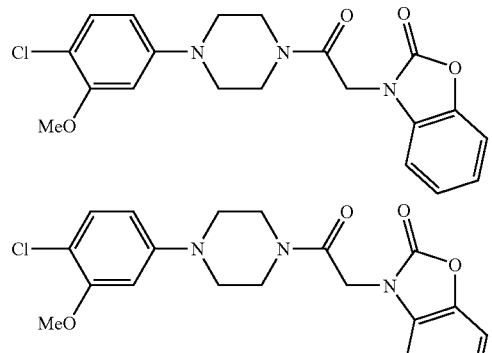

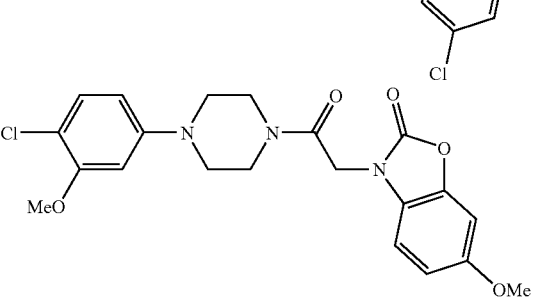

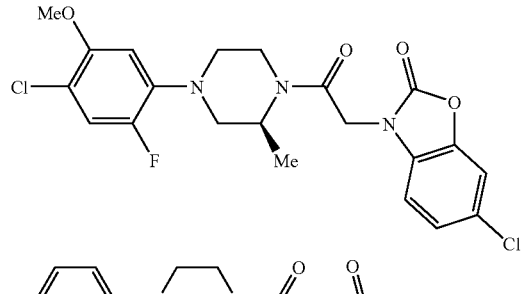

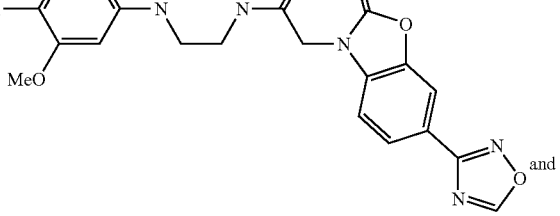

and

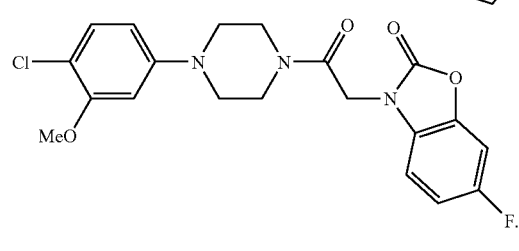

6. A pharmaceutical composition comprising a pharmaceutically acceptable excipient or carrier and a compound of claim 1.

7. The compound of claim 1, wherein said compound is a compound selected from the group consisting of:
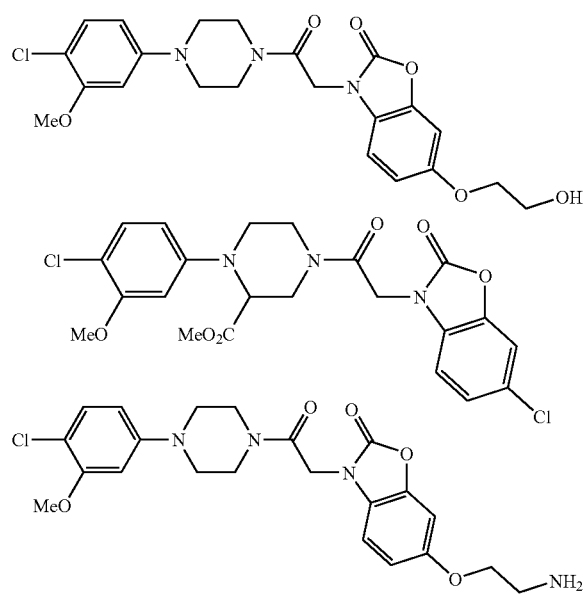
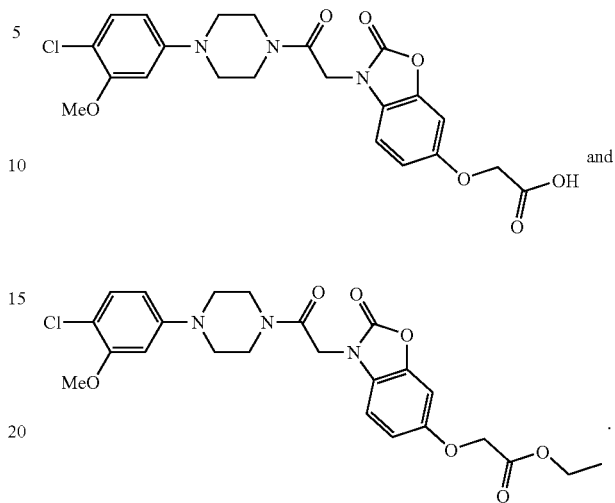
* * * * *